(12) United States Patent
Feinstein et al.

(10) Patent No.: US 7,872,119 B2
(45) Date of Patent: Jan. 18, 2011

(54) INHIBITORS OF RTP801 AND THEIR USE IN DISEASE TREATMENT

(75) Inventors: Elena Feinstein, Rehovot (IL); Rami Skaliter, Nes Ziona (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 12/072,392

(22) Filed: Feb. 26, 2008

(65) Prior Publication Data

US 2008/0269156 A1 Oct. 30, 2008

Related U.S. Application Data

(60) Provisional application No. 60/903,737, filed on Feb. 26, 2007.

(51) Int. Cl.
C07H 21/04 (2006.01)
C07H 21/02 (2006.01)
A61K 48/00 (2006.01)

(52) U.S. Cl. .................. 536/24.5; 536/23.1; 514/44

(58) Field of Classification Search .................. None
See application file for complete search history.

(56) References Cited

U.S. PATENT DOCUMENTS

| 5,898,031 | A | 4/1999 | Crooke |
|---|---|---|---|
| 6,107,094 | A | 8/2000 | Crooke |
| 6,372,249 | B1 | 4/2002 | Smith et al. |
| 6,455,674 | B1 | 9/2002 | Einat et al. |
| 7,452,987 | B2 | 11/2008 | Giese et al. |
| 7,626,015 | B2 | 12/2009 | Feinstein et al. |
| 7,655,788 | B2 | 2/2010 | Khvorova et al. |
| 2002/0119463 | A1 | 8/2002 | Faris et al. |
| 2002/0137077 | A1 | 9/2002 | Hopkins et al. |
| 2003/0104973 | A1 | 6/2003 | Einat et al. |
| 2003/0108871 | A1 | 6/2003 | Kaser |
| 2003/0165864 | A1 | 9/2003 | Lasek et al. |
| 2003/0207840 | A1 | 11/2003 | Riggins et al. |
| 2005/0080246 | A1 | 4/2005 | Allerson et al. |
| 2006/0217329 | A1 | 9/2006 | Feinstein |
| 2007/0281326 | A1 | 12/2007 | Wechsler et al. |
| 2008/0064650 | A1 | 3/2008 | Feinstein et al. |
| 2008/0188647 | A1 | 8/2008 | Khvorova |

FOREIGN PATENT DOCUMENTS

| DE | 19816395 | 10/1999 |
|---|---|---|
| EP | 1 394 274 A2 | 3/2004 |
| EP | 1009753 B1 | 4/2005 |
| JP | 2003-259877 | 9/2003 |
| WO | WO 99/09046 | 2/1999 |
| WO | WO 00/14283 | 3/2000 |
| WO | WO 00/44895 | 8/2000 |
| WO | WO 00/61620 | 10/2000 |
| WO | WO 00/77022 A1 | 12/2000 |
| WO | WO 01/12659 A2 | 2/2001 |
| WO | WO 01/36646 A1 | 5/2001 |
| WO | WO 01/70979 A2 | 9/2001 |
| WO | WO 01/75164 A2 | 10/2001 |
| WO | WO 01/77289 A2 | 10/2001 |
| WO | WO 02/31111 A2 | 4/2002 |
| WO | WO 02/44321 A2 | 6/2002 |
| WO | WO 02/46465 A2 | 6/2002 |
| WO | WO 02/055693 | 7/2002 |
| WO | WO 02/101075 A2 | 12/2002 |
| WO | WO 03/010205 A1 | 2/2003 |
| WO | WO 03/070918 A2 | 8/2003 |
| WO | WO 03/074654 A2 | 9/2003 |
| WO | WO 03/101283 | 12/2003 |
| WO | WO 2004/015107 A2 | 2/2004 |
| WO | WO 2004/018999 A2 | 3/2004 |
| WO | WO 2004/030615 A2 | 4/2004 |
| WO | WO 2004/035615 A2 | 4/2004 |
| WO | WO 2004/039956 A2 | 5/2004 |
| WO | WO 2004/042024 A2 | 5/2004 |
| WO | WO 2004/042024 A3 | 5/2004 |
| WO | WO 2004/045543 A2 | 6/2004 |
| WO | WO 2004/045543 A3 | 6/2004 |
| WO | WO 2004/045545 A2 | 6/2004 |
| WO | WO 2004/060270 A2 | 7/2004 |
| WO | WO 2004/076633 A2 | 9/2004 |
| WO | WO 2004/091383 A2 | 10/2004 |
| WO | WO 2005/016000 A1 | 2/2005 |
| WO | WO 2008/106102 | 9/2008 |
| WO | WO 2009/116037 A3 | 9/2009 |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Amarzguioui M, Holen T, Babaie E, Prydz H. (2003) Tolerance for mutations and chemical modifications in a siRNA. Nucleic Acids Res. 31(2) :589-95.
Barik, Sailen (2005). "Silence of the Transcripts; RNA Interference In Medicine," *J. Mol. Med.* 83:764-773.
Bartel, David P. et al. (2004). "MicroRNAs: Genomics Biogenesis, Mechanism, and Function," *Cell*, 116:281-297.
Bernstein Emily et al. (2001). "Role for a Bidentate Ribonuclease in the Initiation Step of RNA Interference," *Nature*, 409:363-366.
Bitko, Vira et al. (2004). "Inhibition of Respiratory Viruses by Nasally Administered siRNA," *Nature Medicine*, 11(1):50-55.
Brafman, A. et al., (2004) "Inhibition of Oxygen-Induced Retinopathy in RTP801-Deficient Mice," *Investigative Ophthalmology & Visual Science*, 45(10): 3796-3805.

(Continued)

*Primary Examiner*—Amy Bowman
(74) *Attorney, Agent, or Firm*—John P. White; Cooper & Dunham LLP

(57) ABSTRACT

The present invention provides novel molecules, compositions, methods and uses for treating microvascular disorders, eye diseases respiratory conditions and hearing disorders based upon inhibition of the RTP801 gene and/or protein.

13 Claims, 2 Drawing Sheets

OTHER PUBLICATIONS

Braasch Da, et al. (2003) "RNA interference in mammalian cells by chemically-modified RNA," *Biochemistry*, 42:7967-7975.

Brugarolas, J. et al., (2004) "Regulation of mTOR Function in Response to Hypoxia by REDD1 and the TSC1/TSC2 Tumor Suppressor Complex," *Genes & Development*, 18: 2893-2904.

Brummelkamp, Thijn R. et al. (2002). "A System for Stable Expression of Short Interfering RNAs in Mammalian Cells," *Science*, 296: 550-553.

Caplen, Natasha J. et al. (2001). "Specific Inhibition of Gene Expression by Small Double-Stranded RNAs in Invertebrate Vertebrate Systems," *PNAS*, 98(17):9742-9747.

Chakraborty, Chiranjib (2007) "Potentiality of Small Interfering RNAs (siRNA) as Recent Therapeutic Targets for Gene-Silencing," *Current Drug Targets*, 8:469-482.

Chalk, Alistair M. et al., (2004). "Improved and Automated Prediction of Effective siRNA," *Biochemical and Biophysical Research Communications*, 319:264-274.

Czauderna F, Fechtner M, Dames S, Aygün H, Klippel A, Pronk GJ, Giese K, Kaufmann J. (2003) "Structural variations and stabilising modifications of synthetic siRNAs in mammalian cells," *Nucleic Acids Res.* 31(11):2705-16.

Elbashir, Sayda M. et al. (2000). "RNA Interference is Mediated by 21- and 22-nucleotide RNAs," *Genes & Development*, 15:188-200.

Elbashir, Sayda M. et al. (2001). "Duplexes of 21-nucleotide RNAs mediated RNA interference in cultured mammalian cells," *Nature*, 411:494-498.

Elbashir SM, Martinez J, Patkaniowska A, Lendeckel W, Tuschl T. (2001) "Functional anatomy of siRNAs for mediating efficient RNAi in Drosophila melanogaster embryo lysate," *EMBO J.* 20(23):6877-88.

Fire, Andrew et al., (1998). "Potent and Specific Genetic Interference by Double-stranded RNA in Caenorhabditis Elegans," *Nature*, 391:806-811.

Ellisen, L. et al., (2002) "REDD1, A Developmentally Regulated Transcriptional Target of p63 and p53, Links p63 to Regulation of Reactive Oxygen Species," *Molecular Cell*, 10:995-1005.

Frolov, A. et al., (2003) "Response Markers and the Molecular Mechanisms of Action of Gleevec in Gastrointestinal Stromal Tumors," *Molecular Cancer Therapeutics*, 2: 699-709.

Kim, J. et al., (2003) "Identification of Amyloid β-peptide Responsive Genes by cDNA Microarray Technology: Involvement of *RTP801* in Amyloid β-peptide Toxicity," *Experimental and Molecular Medicine*, 35(5): 403-411.

Lal, A. et al., (2001) "Transcriptional Response to Hypoxia in Human Tumors," *Journal of the National Cancer Institute*, 93(17): 1337-1343.

Lee, Youngtae et al., (2003). "The nuclear RNase III Drosha initiates microRNA processing," Nature, 425:415-419.

Lee, M. et al., (2004) "Sp1-Dependant Regulation of the RTP801 Promoter and Its Application to Hypoxia-Inducible VEGF Plasmid for Ischemic Disease," *Pharmaceutical Research*, 21(5): 736-741.

Levenkova, Natasha et al., (2004). "Gene specific siRNA selector," *Bioinformatics*, 20(3)430-432.

Lewis MI, et al. (2002) Apoptosis as a potential mechanism of muscle cachexia in chronic obstructive pulmonary disease. *Am. J. Respir. Crit. Care Med.* 166:434-435.

McManus, Michael T. and Sharp, Phillip A., (2002). "Gene Silencing in Mammals by Small Interfering RNAs," Genetics, 3:737-747.

Prakash TP, Allerson CR, Dande P, Vickers TA, Sioufi N, Jarres R, Baker BF, Swayze EE, Griffey RH, Bhat B. (2005) "Positional effect of chemical modifications on short interference RNA activity in mammalian cells," *J Med Chem.* 48(13):4247-53.

Rangasamy, R. et al., (2004) "Genetic Ablation of Nrf2 Enhances Susceptibility to Cigarette Smoke-Induced Emphysema in Mice," *The Journal of Clinical Investigation*, 114(9): 1248-1259.

Reich, S. et al., (2003). "Small interfering RNA (siRNA) targeting VEGF effectively inhibits ocular neovascularization in a mouse model," *Molecular Vision*, 9:210-216.

Reiling, J. and Hafen, E., (2004) "The Hypoxia-Induced Paralogs Scylla and Charybdis Inhibit Growth by Down-Regulating S6K Activity Upstream of TSC in Drosophila," *Genes & Development*, 18:2879-2892.

Richard, E. et al., (2000) "Nonhypoxic Pathway Mediates the Induction of Hypoxia-Inducible Factor 1α in Vascular Smooth Muscle Cells," *The Journal of Biological Chemistry*, 275(35):26765-26771.

Schwarzer, R. et al., (2005) "REDD1 Integrates Hypoxia-Mediated Survival Signaling Downstream of Phosphatidylinositol 3-kinase," *Oncogene*, 24: 1138-1149.

Shoshani, T. et al., (2002) "Identification of a Novel Hypoxia-Inducible Factor 1-Responsive Gene, *RTP801*, Involved in Apoptosis," *Molecular and Cell Biology*, 22(7): 2283-2293.

Sioud, Moudly and Leirdal, Marianne, (2004) . "Potential Design Rules and Enzymatic Synthesis of siRNAs," *Methods in Molcular Biology*, 252:457-468.

Strausberg, R. et al., (2002) "Generation and Initial Analysis of More Than 15,000 Full-Length Human and Mouse cDNA Sequences," *Proceedings of the National Academy of Sciences of the United States of America*, 99(26): 16899-16903.

Suter M, et al. (2000) "Age-related macular degeneration," *J. Biol. Chem.* 275-(50):39625-39630.

Tolentino, Michael J. et al., (2004). "Intravitreal Injection of Vascular Endothelial Growth Factor Small Interfering RNA Inhibits Growth and Leakage in a Nonhuman Primate, Laser- induced Model of Choroidal Neovascularization," *Retina, The Journal of Retinal and Vitreous Diseases*, 24(1):132-138.

Tuder R, et al. (2003) "Apoptosis and Emphysema: The Missing Link," *Am. J. Respir. Cell. Mol. Biol.* 28:551-554.

Ui-Tei, Kumiko et al., (2004). "Guidelines for the selection of highly effective siRNA sequences for mammalian and chick RNA interference," *Nucleic Acids Research*, 32(3):936-948.

Vignola A, et al. (1999) "Evaluation of apoptosis of eosinophils, macrophages, and T lymphocytes in mucosal biopsy specimens of patients with asthma and chronic bronchitis," *J. Allergy Clin. Immunol.* 103:563-573.

Wang, J. and Ortiz de Montellano, P., (2003) "The Binding Sites on Human Heme Oxygenase-1 for Cytochrome P450 Reductase and Biliverdin Reductase," *The American Society for Biochemistry and Molecular Biology, Inc.*, p. 1-38.

Elena Feinstein and Rami Skaliter, U.S. Appl. No. 11/655,636, filed Jan. 18, 2007 and pending claims.

International Search Report issued by the International Searching Authority (ISA/US) on Apr. 18, 2007 in connection with International Application No. PCT/US05/29236.

Written Opinion of the International Searching Authority (ISA/US) issued on Apr. 18, 2007 in connection with International Application No. PCT/US05/29236.

International Preliminary Report on Patentability issued by the International Bureau of WIPO on May 8, 2007 in connection with International Application No. PCT/US05/29236.

Search Report issued by the Australian Patent Office on May 14, 2008 in connection with Singaporean Application/Patent No. 0702035-7.

Written Opinion issued by the Australian Patent Office on May 14, 2008 in connection with Singaporean Application/Patent No. 0702035-7.

Sep. 30, 2004 Non-Final Office Action issued in connection with U.S. Appl. No. 10/091,333.

Dec. 28, 2004 Non-Final Office Action issued in connection with U.S. Appl. No. 10/091,333.

Jun. 15, 2005 Final Office Action issued in connection with U.S. Appl. No. 10/091,333.

Mar. 8, 2006 Non-Final Office Action issued in connection with U.S. Appl. No. 10/091,333.

Nov. 14, 2006 Final Office Action issued in connection with U.S. Appl. No. 10/091,333.

Jul. 6, 2007 Non-Final Office Action issued in connection with U.S. Appl. No. 10/091,333.

Feb. 13, 2008 Non-Final Office Action issued in connection with U.S. Appl. No. 10/091,333.

May 1, 2008 Non-Final Office Action issued in connection with U.S. Appl. No. 11/655,610.

Oct. 2, 2008 Non-Final Office Action issued in connection with U.S. Appl. No. 11/655,610.
Jan. 29, 2009 Official Action in European Patent application No. 05786796.2.
Dec. 3, 2008 Office Action in connection with Eurasian Application No. 200700333/28.
Mar. 2, 2009 Official Action in connection with Ukrainian Patent Application No. 200701610.
Jun. 24, 2008 Official Action in connection with New Zealand Patent Application No. 553162.
Feb. 27, 2009 Search Report in connection with Georgian Patent Application No. 76400.
Holen et al., (2002). "Positional effects of short interfering RNAs targeting the human coagulation trigger Tissue Factor," *Nucleic Acids Research*, vol. 30, No. 8, p. 1757-1766.
Apr. 17, 2009 Notice of Allowability in connection with U.S. Appl. No. 11/655,610.
May 7, 2009 Office Action in connection with Japanese Patent Application No. 2007-527969.
Jan. 8, 2008 Notice of Preliminary Rejection in connection with Korean Patent Application No. 2007-7006061.
Mar. 18, 2009 Notice of Final Rejection in connection with Korean Patent Application No. 2007-7006061.
Mar. 18, 2009 Notice of Dismissal of Amendment in connection with Korean Patent Application No. 2007-7006061.
May 27, 2009 Office Action in connection with Uzbekistani Patent Application No. 2007-0060.
Jul. 9, 2009 Official Action in connection with Ukrainian Patent Application No. 200701610.
Jun. 5, 2009 Office Action in connection with Chinese Patent Application No. 200580034968.5.
May 20, 2009 Notification of Readiness to Grant Eurasian Patent issued in connection with Eurasian patent application No. 200700333.
Jun. 15, 2009 Examiner's Report issued in connection with Chilean patent application No. 141-07.
Sep. 21, 2009 Official Action issued in connection with European Patent Application No. 05786796.2.
Sep. 23, 2009 Official Action issued in connection with Georgian Patent Application No. AP2005009869.
Oct. 14, 2009 Official Action issued in connection with Uzbekistan Patent Application No. IAP 2007 0060.
Sep. 15, 2009 Office Action in connection with Japanese Patent Application No. 2007-527969.
Nov. 20, 2009 Notice of Allowance issued in connection with U.S. Appl. No. 11/207,119, and Allowed Claims.
Declaration of Non-Establishment of International Search Report issued by the International Searching Authority (ISA/US) on Jan. 30, 2009 in connection with International Application No. PCT/US08/02483.
Written Opinion of the International Searching Authority (ISA/US) issued on Jan. 30, 2009 in connection with International Application No. PCT/US08/02483.
International Preliminary Report on Patentability issued by the International Bureau of WIPO on Aug. 26, 2009 in connection with International Application No. PCT/US08/02483.
Apr. 17, 2009 Notice of Allowability in connection with U.S. Appl. No. 11/655,610.
May 7, 2009 Office Action in connection with Japanese Patent Application No. 2007-527969.
Jan. 8, 2008 Notice of Preliminary Rejection in connection with Korean Patent Application No. 2007-7006061.
Mar. 18, 2009 Notice of Final Rejection in connection with Korean Patent Application No. 2007-7006061.
Mar. 18, 2009 Notice of Dismissal of Amendment in connection with Korean Patent Application No. 2007-7006061.
May 27, 2009 Office Action in connection with Uzbekistani Patent Application No. 2007-0060.
Jul. 9, 2009 Official Action in connection with Ukrainian Patent Application No. 200701610.
Jun. 5, 2009 Office Action in connection with Chinese Patent Application No. 200580034968.5.
Apr. 22, 2010 Notice of Allowance in connection with U.S. Appl. No. 11/207,119 and claims allowed therein.
Office Action dated Sep. 21, 2009 issued in corresponding European Application No. 05786796.2.
Mar. 31, 2010 Response to Official Action dated Sep. 21, 2009, in corresponding European Application No. 05786796.2.

* cited by examiner

Figure 1
Human RTP801 polynucleotide (SEQ ID NO:1)

```
TTTGCCCTC  GAGGCCAAGA  ATTCGGCACG  AGGGGGGGAG  GTGCGAGCGT  GGACCTGGGA   60
CGGGTCTGGG  CGGCTCTCGG  TGGTTGGCAC  GGGTTCGCAC  ACCCATTCAA  GCGGCAGGAC  120
GCACTTGTCT  TAGCAGTTCT  CGCTGACCGC  GCTAGCTGCG  GCTTCTACGC  TCCGGCACTC  180
TGAGTTCATC  AGCAAACGCC  CTGGCGTCTG  TCCTCACCAT  GCCTAGCCTT  TGGGACCGCT  240
TCTCGTCGTC  GTCCACCTCC  TCTTCGCCCT  CGTCCTTGCC  CCGAACTCCC  ACCCCAGATC  300
GGCCGCCGCG  CTCAGCCTGG  GGGTCGGCGA  CCCGGGAGGA  GGGGTTTGAC  CGCTCCACGA  360
GCCTGGAGAG  CTCGGACTGC  GAGTCCCTGG  ACAGCAGCAA  CAGTGGCTTC  GGGCCGGAGG  420
AAGACACGGC  TTACCTGGAT  GGGGTGTCGT  TGCCCGACTT  CGAGCTGCTC  AGTGACCCTG  480
AGGATGAACA  CTTGTGTGCC  AACCTGATGC  AGCTGCTGCA  GGAGAGCCTG  GCCCAGGCGC  540
GGCTGGGCTC  TCGACGCCCT  GCGCGCCTGC  TGATGCCTAG  CCAGTTGGTA  AGCCAGGTGG  600
GCAAAGAACT  ACTGCGCCTG  GCCTACAGCG  AGCCGTGCGG  CCTGCGGGGG  GCGCTGCTGG  660
ACGTCTGCGT  GGAGCAGGGC  AAGAGCTGCC  ACAGCGTGGG  CCAGCTGGCA  CTCGACCCCA  720
GCCTGGTGCC  CACCTTCCAG  CTGACCCTCG  TGCTGCGCCT  GGACTCACGA  CTCTGGCCCA  780
AGATCCAGGG  GCTGTTTAGC  TCCGCCAACT  CTCCCTTCCT  CCCTGGCTTC  AGCCAGTCCC  840
TGACGCTGAG  CACTGGCTTC  CGAGTCATCA  AGAAGAAGCT  GTACAGCTCG  AACAGCTGC   900
TCATTGAGGA  GTGTTGAACT  TCAACCTGAG  GGGGCCGACA  GTGCCCTCCA  AGACAGAGAC  960
GACTGAACTT  TTGGGGTGGA  GACTAGAGGC  AGGAGCTGAG  GGACTGATTC  CTGTGGTTGG  1020
AAAACTGAGG  CAGCCACCTA  AGGTGGAGGT  GGGGGAATAG  TGTTTCCCAG  GAAGCTCATT  1080
GAGTTGTGTG  CGGGTGGCTG  TGCATTGGGG  ACACATACCC  CTCAGTACTG  TAGCATGAAA  1140
CAAAGGCTTA  GGGGCCAACA  AGGCTTCCAG  CTGGATGTGT  GTGTAGCATG  TACCTTATTA  1200
TTTTTGTTAC  TGACAGTTAA  CAGTGGTGTG  ACATCCAGAG  AGCAGCTGGG  CTGCTCCCGC  1260
CCCAGCCCGG  CCCAGGGTGA  GGAAGAGGC   ACGTGCTCCT  CAGAGCAGCC  GGAGGGAGGG  1320
GGGAGGTCGG  AGGTCGTGGA  GGTGGTTTGT  GTATCTTACT  GGTCTGAAGG  ACCAAGTGT   1380
GTTTGTTGTT  TGTTTTGTAT  CTTGTTTTTC  TGATCGGAGC  ATCACTACTG  ACCTGTTGTA  1440
GGCAGCTATC  TTACAGACGC  ATGAATGTAA  GAGTAGGAAG  GGGTGGGTGT  CAGGGATCAC  1500
TTGGGATCTT  TGACACTTGA  AAAATTACAC  CTGGCAGCTG  CGTTTAAGCC  TTCCCCCATC  1560
GTGTACTGCA  GAGTTGAGCT  GGCAGGGGAG  GGGCTGAGAG  GGTGGGGGCT  GGAACCCCTC  1620
CCCGGGAGGA  GTGCCATCTG  GGTCTTCCAT  CTAGAACTGT  TTACATGAAG  ATAAGATACT  1680
CACTGTTCAT  GAATACACTT  GATGTTCAAG  TATTAAGACC  TATGCAATAT  TTTTTACTTT  1740
TCTAATAAAC  ATGTTTGTTA  AAACAAAAAA  AAAAAAAAA   AA                     1782
```

Figure 2
Human RTP801 polypeptide (SEQ ID NO:2)

```
MPSLWDRFSS SSTSSSPSSL PRTPTPDRPP RSAWGSATRE EGFDRSTSLE  50
SSDCESLDSS NSGFGPEEDT AYLDGVSLPD FELLSDPEDE HLCANLMQLL 100
QESLAQARLG SRRPARLLMP SQLVSQVGKE LLRLAYSEPC GLRGALLDVC 150
VEQGKSCHSV GQLALDPSLV PTFQLTLVLR LDSRLWPKIQ GLFSSANSPF 200
LPGFSQSLTL STGFRVIKKK LYSSEQLLIE EC                    232
```

INHIBITORS OF RTP801 AND THEIR USE IN DISEASE TREATMENT

This application claims benefit of U.S. Provisional Application No. 60/903,737, filed Feb. 26, 2007, the content of which is hereby incorporated by reference in into this application.

FIELD OF THE INVENTION

The present invention relates to novel siRNA molecules which inhibit the RTP801 gene and to the use of such molecules to treat respiratory disorders of all types (including pulmonary disorders), eye diseases and conditions, microvascular disorders, angiogenesis- and apoptosis-related conditions, and hearing impairments.

BACKGROUND OF THE INVENTION

RTP801

Gene RTP801 was first reported by the assignee of the instant application. U.S. Pat. Nos. 6,455,674, 6,555,667, and 6740738, all assigned to the assignee of the instant application, disclose and claim per se the RTP801 polynucleotide and polypeptide, and antibodies directed toward the polypeptide. RTP801 represents a unique gene target for hypoxia-inducible factor-1 (HIF-1) that may regulate hypoxia-induced pathogenesis independent of growth factors such as VEGF. Additionally, the assignee of the instant application also discovered a similar gene termed RTP801L (for RTP801 Like) which can be used in combination therapies with RTP801 (see below). For further information re RTP801L see PCT publication No. WO07/141,796, assigned to the assignee of the instant application, which is hereby incorporated by reference in its entirety.

The following patents and patent applications give aspects of background information.

WO 2001070979 relates to nucleic acid markers which are overexpressed in ovarian cancer cells.

US application 2003108871 relates to a composition comprising several cDNAs that are differentially expressed in treated human C3A liver cell cultures.

US application 2002119463 discloses a new composition, useful for treating and diagnosing prostate cancer, said composition comprising human cDNAs that are differentially expressed in prostate cancer.

WO 2004018999 discloses a method for assessing, characterizing, monitoring, preventing and treating cervical cancer.

EP 1394274 relates to a method of testing for bronchial asthma or chronic obstructive pulmonary disease by comparing the expression level of a marker gene in a biological sample from a subject with the expression level of the gene in a sample from a healthy subject.

WO 2002101075 relates to an isolated nucleic acid molecule useful for detecting, characterizing, preventing and treating human cervical cancers.

WO 2003010205 relates to inhibiting angiogenesis for treating wound healing, retinopathy, ischemia, inflammation, microvasculopathy, bone healing and skin inflammation.

WO 2002046465 relates to identifying a gene involved in disease for treating hypoxia-regulated conditions.

The following publications also give background information: Shoshani, et al. Mol. Cel. Biol., April 2002, p. 2283-2293;

Brafman, et al. Invest Opthalmol Vis Sci. 2004 October; 45 (10): 3796-805;

Ellisen, et al. Molecular Cell, Vol. 10, 995-1005, November, 2002;

Richard et al. J. Biol. Chem. 2000, Sep. 1; 275(35): 26765-71.

siRNAs and RNA Interference

RNA interference (RNAi) is a phenomenon involving double-stranded (ds) RNA-dependent gene-specific posttranscriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000. 5:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

An siRNA is a double-stranded RNA which down-regulates or silences (i.e. fully or partially inhibits) the expression of an endogenous or exogenous gene/mRNA. RNA interference is based on the ability of certain dsRNA species to enter a specific protein complex, where they are then targeted to complementary cellular RNAs and specifically degrades them. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al., Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Bernstein et al., Nature, 2001, 409:363-6 and Lee et al., Nature, 2003, 425:415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol. Ther. 2003, 5(3): 217-24). (For additional information on these terms and proposed mechanisms, see for example, Bernstein, et al., RNA. 2001, 7(11):1509-21; Nishikura, Cell. 2001, 107(4): 415-8 and PCT Publication No. WO 01/36646).

Studies have revealed that siRNA can be effective in vivo in both mammals and humans. Specifically, Bitko et al., showed that specific siRNAs directed against the respiratory syncytial virus (RSV) nucleocapsid N gene are effective in treating mice when administered intranasally (Bitko et al., Nat. Med. 2005, 11(1):50-55). For reviews of therapeutic applications of siRNAs see Barik (Mol. Med. 2005, 83: 764-773), Chakraborty (Current Drug Targets 2007 8(3):469-82) and Dykxhoom, et al (Gene Therapy 2006, 13, 541-552). In addition, clinical studies with short siRNAs that target the VEGFR1 receptor in order to treat age-related macular degeneration (AMD) have been conducted in human patients. In studies such siRNA administered by intravitreal (intraocular) injection was found effective and safe in 14 patients tested (Kaiser, Am J. Opthalmol. 2006 142(4):660-8).

SUMMARY OF THE INVENTION

The present invention provides novel methods and compositions for treating microvascular disorders, macular degeneration, respiratory disorders, spinal cord injury or disease, hearing loss and other diseases and conditions.

In one embodiment, novel molecules which inhibit RTP801 and can be used to treat various diseases and indications are provided.

In another embodiment, the present invention provides a method of treating a patient suffering from a microvascular disorder, macular degeneration or a respiratory disorder, comprising administering to the patient a pharmaceutical composition comprising an RTP801 inhibitor.

Another embodiment of the present invention concerns a method for treating a patient suffering from COPD, comprising administering to the patient a pharmaceutical composition comprising a therapeutically effective amount of an RTP801 inhibitor. In one embodiment the inhibitor is an siRNA molecule, an antisense molecule, an antibody (such as a neutralizing antibody), a dominant negative peptide or a ribozyme.

Another embodiment of the present invention concerns a method for treating a patient suffering from macular degeneration, comprising administering to the patient a pharmaceutical composition comprising a therapeutically effective amount of an RTP801 inhibitor. In one embodiment the inhibitor is an siRNA molecule, an antisense molecule, an antibody (such as a neutralizing antibody), a dominant negative peptide or a ribozyme.

Another embodiment of the present invention concerns a method for treating a patient suffering from a microvascular disorder, comprising administering to the patient a pharmaceutical composition comprising a therapeutically effective amount of an RTP801 inhibitor. In one embodiment the inhibitor is an siRNA molecule, an antisense molecule, an antibody (such as a neutralizing antibody), a dominant negative peptide or a ribozyme. In certain preferred embodiments the 801 inhibitor is an siRNA compound.

An additional embodiment of the present invention provides for the use of a therapeutically effective amount of an RTP801 inhibitor for the preparation of a medicament for promoting recovery in a patient suffering from a respiratory disorder. In one embodiment the respiratory disorder is COPD and the inhibitor is preferably an siRNA.

An additional embodiment of the present invention provides for the use of a therapeutically effective dose of an RTP801 inhibitor for the preparation of a medicament for promoting recovery in a patient suffering from macular degeneration. In one embodiment the macular degeneration is AMD and the inhibitor is preferably an siRNA.

An additional embodiment of the present invention provides for the use of a therapeutically effective amount of an RTP801 inhibitor for the preparation of a medicament for promoting recovery in a patient suffering from a microvascular disorder. In one embodiment the microvascular disorder is diabetic retinopathy and the inhibitor is preferably an siRNA.

The present invention relates generally to methods and compositions for treating or preventing the incidence or severity of hearing impairment (or balance impairment), particularly hearing impairment associated with cell death of the inner ear hair cells. The methods and compositions involve administering to a mammal in need of such treatment a prophylactically or therapeutically effective amount of one or more compounds which down-regulate expression of the RTP801 gene, particularly novel small interfering RNAs (siRNAs).

More specifically, the present invention provides methods and compositions for treating a patient suffering from hearing impairment, or other oto-pathologies associated with cell death of inner ear hair cells. Such oto-pathologies may be the result of acoustic trauma, mechanical trauma, or ototoxin-induced hearing loss. The methods of the invention comprising administering to the patient one or more compounds which down-regulate expression of the RTP801 gene, particularly siRNAs that inhibit RTP801 typically as a pharmaceutical composition, in a therapeutically effective dose so as to thereby treat the patient.

In one embodiment, the present invention provides for improved compositions and methods for treatments requiring administration of a pharmaceutical drug having an ototoxic, hearing-impairing side-effect, in combination with a therapeutically effective amount of one or more siRNA molecules that inhibit RTP801, to treat or prevent the ototoxicity induced by the pharmaceutical drug. The compositions of the invention can be administered at a suitable interval(s) either prior to, subsequent to, or substantially concurrent with the administration of the ototoxic, hearing-impairing drug that induces inner ear apoptotic tissue damage. Similarly, this treatment can be effective as a prophylactic treatment prior to or in conjunction with conditions which cause acoustic trauma.

Accordingly, it is an object of the invention to provide an improved composition containing a therapeutically effective amount of one or more siRNA molecules that inhibit RTP801 in combination with an ototoxic, hearing-impairing pharmaceutical drug for administration to a mammal. The combination of drugs may be administered separately; the siRNA molecules that inhibit RTP801 would then be administered locally while the ototoxic, hearing-impairing, pharmaceutical drug is administered systemically. The siRNA molecules may be administered prior to, simultaneously with or subsequent to the ototoxic drug. The composition or compositions can further contain a pharmaceutically acceptable carrier. The pharmaceutical composition will have lower ototoxicity than the ototoxic pharmaceutical alone, and preferably, will have a higher dosage of the ototoxic pharmaceutical than typically used. Examples of such improved compositions include cisplatin or other ototoxic neoplastic agent or an aminoglycoside antibiotic(s) in combination with the therapeutically effective amount of one or more siRNA molecules that inhibit RTP801.

Still further, the invention relates to the use of the compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use of the compositions of the invention in cases where quinine or quinine-like compounds are needed. The present invention provides a solution to the art that has long sought a therapy and a medicament which can treat the ototoxic effects currently associated with certain quinines without sacrificing their effectiveness.

The present invention further relates to methods and compositions for treating or preventing the incidence or severity of pressure sores. The methods and compositions involve administering to a mammal in need of such treatment a prophylactically or therapeutically effective amount of one or more compounds which down-regulate expression of the RTP801 gene, particularly novel small interfering RNAs (siRNAs).

Further, the present invention relates to methods and compositions for the treatment of any ischemic or ischemia-reperfusion injuries or conditions, as described herein. Said methods and compositions involve administering to a mammal in need of such treatment a prophylactically or therapeutically effective amount of one or more compounds which down-regulate expression of the RTP801 gene, particularly novel small interfering RNAs (siRNAs).

As indicated above, the present invention provides inhibitors of RTP801. In various embodiments the inhibitor is selected from the group consisting of siRNA, shRNA, an aptamer, an antisense molecule, miRNA, a ribozyme, and an antibody. In the presently preferred embodiments the inhibitor is siRNA. In various embodiments the siRNA comprises once or more ribonucleotides having a chemical modification in the sugar residue.

Accordingly, in one aspect the present invention provides novel double stranded oligoribonucleotides that inhibit expression of RTP801. The invention also provides pharmaceutical compositions comprising one or more such oligoribonucleotides or a vector capable of expressing the oligoribonucleotide. The present invention further relates to methods for treating or preventing the incidence or severity of various diseases or conditions in a subject in need thereof wherein the disease or condition and/or symptoms associated therewith is selected from the group consisting of hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, pancreas, and kidney transplantation, nephro- and neurotoxicity, spinal cord injury, pressure sores, age-related macular degeneration (AMD), dry eye syndrome, oral mucositis and chronic obstructive pulmonary disease (COPD). Such methods involve administering to a mammal in need of such treatment a prophylactically or therapeutically effective amount of one or more such compounds which inhibits or reduces expression or activity of RTP801.

In one aspect the present invention provides a compound having the structure:

5' $(N)_x$—Z 3' (antisense strand)
3' Z'—$(N')_y$ 5' (sense strand)

wherein each of N and N' is a nucleotide which may be modified or unmodified in its sugar residue;

wherein each of $(N)_x$ and $(N')_y$ is an oligonucleotide in which each consecutive N or N' is joined to the next N or N' by a covalent bond;

wherein each of x and y is an integer between 18 and 40;

wherein each of Z and Z' may be present or absent, but if present is 1-5 consecutive nucleotides covalently attached at the 3' terminus of the strand in which it is present; and wherein the sequence of $(N')_y$ is present within a mRNA of RTP801.

In some embodiments the covalent bond joining each consecutive N or N' is a phosphodiester bond. In various embodiments all the covalent bonds are phosphodiester bonds.

In various embodiments the compound comprises ribonucleotides wherein x=y and each of x and y is 19, 20, 21, 22 or 23. In some embodiments x=y=23. In other embodiments x=y=19.

In some embodiments the compound is blunt ended, for example wherein both Z and Z' are absent. In an alternative embodiment, the compound comprises at least one 3' overhang, wherein at least one of Z or Z' is present. Z and Z' can independently comprise one or more covalently linked modified or non-modified nucleotides, for example inverted dT or dA; dT, LNA, mirror nucleotide and the like. In some embodiments each of Z and Z' are independently selected from dT and dTdT.

In some embodiments N or N' comprises a modification in the sugar residue. In other embodiments $(N)_x$ and/or $(N')_y$ comprises at least one ribonucleotide modified in the sugar residue. In some embodiments at least one of $(N)_x$ and $(N')_y$ comprises a ribonucleotide having a modification at the 2' position of the sugar residue. In some embodiments the modification in the 2' position comprises the presence of an amino, a fluoro, an alkoxy or an alkyl moiety. In certain embodiments the 2' modification comprises a methoxy moiety. A presently preferred modification is a 2' methoxy of the sugar residue (2'-O-methyl; 2'-O-Me; 2'-O—$CH_3$).

In some embodiments the compound comprises modified alternating ribonucleotides in one or both of the antisense and the sense strands, i.e at least one of $(N)_x$ and $(N')_y$ comprises modified alternating ribonucleotides. In certain embodiments the compound comprises modified alternating ribonucleotides in the antisense and the sense strands. In other embodiments the compound comprises modified alternating ribonucleotides in the antisense strand only. In certain embodiments the middle ribonucleotide of the antisense strand is not modified; e.g. ribonucleotide in position 10 in a 19-mer strand or position 12 in a 23-mer strand.

In additional embodiments the compound comprises modified ribonucleotides in alternating positions wherein each N at the 5' and 3' termini of $(N)_x$ are modified in their sugar residues, and each N' at the 5' and 3' termini of $(N')_y$ are unmodified in their sugar residues. In some embodiments, neither $(N)_x$ nor $(N')_y$ are phosphorylated at the 3' and 5' termini. In other embodiments either or both $(N)_x$ and $(N')_y$ are phosphorylated at the 3' termini.

In certain embodiments the present invention provides a compound having the structure:

5' $(N)_x$—Z 3' (antisense strand)
3' Z'—$(N')_y$ 5' (sense strand)

wherein each of N and N' is a ribonucleotide which may be modified or unmodified in its sugar residue;

wherein each of $(N)_x$ and $(N')_y$ is an oligomer in which each consecutive N or N' is joined to the next N or N' by a covalent bond;

wherein each of x and y is an integer between 19 and 40;

wherein each of Z and Z' may be present or absent, but if present is 1-5 consecutive nucleotides covalently attached at the 3' terminus of the strand in which it is present; and wherein the sequence of $(N)_x$ and $(N')_y$ is set forth in any one of SEQ ID NOS: 3-70.

In certain embodiments the present invention provides a compound having the structure:

5' $(N)_x$ 3' antisense strand
3' $(N')_y$ 5' sense strand wherein each of N and N' is a nucleotide which may be modified or unmodified in its sugar residue;

wherein x=y=19 and the sequence of $(N)_x$ and $(N')_y$ are fully complementary;

wherein alternating ribonucleotides in $(N)_x$ and $(N')_y$ are modified to result in a 2'-O-methyl modification in the sugar residue of the ribonucleotides; wherein the ribonucleotides at the 5' and 3' termini of $(N)_x$ are modified;

wherein the ribonucleotides at the 5' and 3' termini of $(N')_y$ are unmodified;

wherein $(N)_x$ and $(N')_y$ are phosphorylated or non-phosphorylated at the 3' and 5' termini; and wherein each of N and N' is selected from the group of oligomers set forth in Table A.

In certain embodiments the present invention provides a compound having the structure 5' (N)x 3' antisense strand
3' (N')y 5' sense strand wherein x=y=23 and the sequence of $(N)_x$ and $(N')_y$ are fully complementary;

wherein alternating ribonucleotides in $(N)_x$ and $(N')_y$ are modified to result in a 2'-O-methyl modification in the sugar residue of the ribonucleotides; wherein the ribonucleotides at the 5' and 3' termini of $(N)_x$ are modified;

wherein the ribonucleotides at the 5' and 3' termini of $(N')_y$ are unmodified;

wherein $(N)_x$ and $(N')_y$ are phosphorylated or non-phosphorylated at the 3' and 5' termini; and wherein each of N and N' is selected from the group of oligomers set forth in Table A.

In a second aspect the present invention provides a pharmaceutical composition comprising one or more compounds of the present invention, in an amount effective to inhibit human RTP801 gene expression and a pharmaceutically acceptable carrier.

In another aspect, the present invention relates to a method for the treatment of a subject in need of treatment for a disease or disorder or symptoms associated with the disease or disorder, associated with the expression of RTP801, comprising administering to the subject an amount of an siRNA which reduces or inhibits expression of RTP801.

More specifically, the present invention provides methods and compositions useful in treating a subject suffering from acute renal failure (ARF), hearing loss, glaucoma, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, spinal cord injury, pressure sores, dry eye syndrome, oral mucositis and chronic obstructive pulmonary disease (COPD).

The methods of the invention comprise administering to the subject one or more inhibitory compounds which reduces, inhibits or down-regulate expression of RTP801; and in particular siRNA in a therapeutically effective dose so as to thereby treat the patient.

In one embodiment, the present invention provides methods of treating a disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis, dry eye syndrome and chronic obstructive pulmonary disease (COPD), in a subject in need thereof, comprising administering to the subject an oligonucleotide which inhibits expression of RTP801, in an amount effective to treat the disease or condition.

In one embodiment, the present invention provides methods of treating acute renal failure in a subject in need thereof, comprising administering to the subject an oligonucleotide which inhibits expression of RTP801 in an amount effective to treat the acute renal failure.

In one embodiment, the present invention provides methods of treating spinal-cord injury in a subject in need thereof, comprising administering to the subject an oligonucleotide which inhibits expression of RTP801 in an amount effective to treat the spinal cord injury.

In one embodiment, the present invention provides methods of treating hearing loss in a subject in need thereof, comprising administering to the subject an oligonucleotide which inhibits expression of RTP801 in an amount effective to treat the hearing loss.

In one embodiment, the present invention provides methods of treating a disease or condition selected from chronic obstructive pulmonary disease, acute respiratory distress syndrome and acute lung injury in a subject in need thereof, comprising administering to the subject an oligonucleotide which inhibits expression of RTP801 in an amount effective to treat the disease or condition.

In one embodiment, the present invention provides methods of treating a subject who is an organ transplant recipient or organ transplant donor comprising administering to the subject an oligonucleotide which inhibits expression of RTP801 in an amount effective to prevent rejection of the transplant.

In one embodiment, the present invention provides methods of treating glaucoma in a subject in need thereof, comprising administering to the subject an oligonucleotide which inhibits expression of RTP801 in an amount effective to treat glaucoma.

In one embodiment, the present invention provides methods of treating oral mucositis in a subject in need thereof, comprising administering to the subject an oligonucleotide which inhibits expression of RTP801 in an amount effective to treat oral mucositis.

In one embodiment, the present invention provides methods of treating dry eye syndrome in a subject in need thereof, comprising administering to the subject an oligonucleotide which inhibits expression of RTP801 in an amount effective to treat the syndrome.

In one embodiment, the present invention provides methods of treating a pressure sore in a subject in need thereof, comprising administering to the subject an oligonucleotide which inhibits expression of RTP801 in an amount effective to treat the pressure sore.

In one embodiment, the present invention provides methods of treating a disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis and chronic obstructive pulmonary disease (COPD), in a subject in need thereof, comprising administering to the subject an antibody which inhibits a polypeptide of RTP801 in an amount effective to treat the disease or condition.

In one embodiment, the present invention provides a pharmaceutical composition comprising an antibody which inhibits a polypeptide of RTP801 in an amount effective to inhibit the polypeptide, and a pharmaceutically acceptable carrier.

In one embodiment, the present invention relates to the use of a therapeutically effective dose of an oligonucleotide for the preparation of a composition for treating a subject suffering from a disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis and chronic obstructive pulmonary disease (COPD), wherein the oligonucleotide inhibits expression of the RTP801 gene.

The present invention also provides use of an 801 siRNA compound for the preparation of a medicament useful in treating disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis and chronic obstructive pulmonary disease (COPD), wherein the oligonucleotide inhibits expression of the RTP801 gene.

DETAILED DESCRIPTION OF THE INVENTION

The present invention, in some of its embodiments, concerns inhibition of the RTP801 gene or polypeptide for the treatment of eye diseases, respiratory disorders, microvascular disorders, hearing disorders and ischemic conditions, inter alia. As will be described herein, the preferred inhibitors to be used with the present invention are biological molecules.

Without being bound by theory, the inventors of the present invention have found that RTP801 is involved in various disease states including microvascular disorders, eye diseases, respiratory disorders, hearing disorders, pressure sores, ischemic conditions and spinal cord injury and disease, and it would be beneficial to inhibit RTP801 in order to treat any of said diseases or disorders. Methods, molecules and compositions which inhibit RTP801 are discussed herein at length, and any of said molecules and/or compositions may be beneficially employed in the treatment of a patient suffering from any of said conditions.

The present invention provides methods and compositions for inhibiting expression of the RTP801 gene in vivo. In general, the method includes administering oligoribonucleotides, such as small interfering RNAs (i.e., siRNAs) that are targeted to a particular mRNA and hybridise to it, or nucleic acid material that can produce siRNAs in a cell, in an amount sufficient to down-regulate expression of a target gene by an RNA interference mechanism. In particular, the subject method can be used to inhibit expression of the RTP801 gene for treatment of respiratory disorders, microvascular disorders, eye disorders and hearing impairments.

The present invention relates generally to compounds which down-regulate expression of RTP801, particularly to novel small interfering RNAs (siRNAs), and to the use of these novel siRNAs in the treatment of various diseases and medical conditions. Particular diseases and conditions to be treated are hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, bone marrow, pancreas, cornea and kidney transplantation, spinal cord injury, pressure sores, age-related macular degeneration (AMD), dry eye syndrome, oral mucositis and chronic obstructive pulmonary disease (COPD). Other indications include chemical-induced nephrotoxicity and chemical-induced neurotoxicity, for example toxicity induced by cisplatin and cisplatin-like compounds, by aminoglycosides, by loop diuretics, and by hydroquinone and their analogs.

Lists of preferred siRNA to be used in the present invention are provided in Table A, SEQ ID NOS:3 to 70. 21- or 23-mer siRNA sequences can also be generated by 5' and/or 3' extension of the 19-mer sequences disclosed herein. Such extension is preferably complementary to the corresponding mRNA sequence. siRNAs compounds previously disclosed in co-assigned PCT publication No.s WO06/023544 and WO07/084,684 may be used in the novel uses and methods of treatment disclosed herein.

Methods, molecules and compositions which inhibit RTP801 are discussed herein at length, and any of said molecules and/or compositions may be beneficially employed in the treatment of a subject suffering from any of said conditions.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound which is capable of inhibiting the expression of a gene or the activity of the product of such gene to an extent sufficient to achieve a desired biological or physiological effect. The term "inhibitor" as used herein refers to one or more of an oligonucleotide inhibitor, including siRNA, shRNA, aptamers, antisense molecules, miRNA and ribozymes, as well as antibodies. The oligonucleotide may be chemically modified. The inhibitor may cause complete or partial inhibition.

The term "inhibit" as used herein refers to reducing the expression of a gene or the activity of the product of such gene to an extent sufficient to achieve a desired biological or physiological effect. Inhibition may be complete or partial.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs.

"Oligonucleotide" refers to a compound comprising deoxyribonucleotides and/or ribonucleotides from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The present invention provides methods and compositions for inhibiting expression of the RTP801 gene in vivo. In general, the method includes administering oligoribonucleotides, in particular small interfering RNAs (i.e. siRNAs) or a nucleic acid material that can produce siRNA in a cell, that target an mRNA transcribed from the RTP801 gene in an amount sufficient to down-regulate expression of a target gene by an RNA interference mechanism. In particular, the subject method can be used to inhibit expression of the RTP801 gene for treatment of a disease.

In accordance with the present invention, the siRNA molecules or inhibitors of the RTP801 gene are used as drugs to treat various pathologies.

siRNA Oligoribonucleotides

Table A comprises nucleic acid sequences of sense and corresponding antisense oligomers, useful in preparing corresponding siRNA compounds.

The selection and synthesis of siRNA corresponding to known genes has been widely reported; see for example Ui-Tei et al., J Biomed Biotechnol. 2006; 65052; Chalk et al., BBRC. 2004, 319(1):264-74; Sioud and Leirdal, Met. Mol. Biol.; 2004, 252:457-69; Levenkova et al., Bioinform. 2004, 20(3):430-2; Ui-Tei et al., NAR 2004, 32(3):936-48. For examples of the use of, and production of, modified siRNA see Braasch et al., Biochem., 2003, 42(26):7967-75; Chiu et al., RNA, 2003, 9(9): 1034-48; PCT publications WO 2004/015107 (atugen); WO 02/44321 (Tuschl et al), and U.S. Pat. Nos. 5,898,031 and 6,107,094.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

The present invention provides double-stranded oligoribonucleotides (e.g. siRNAs), which down-regulate the expression of RTP801 according to the present invention. An siRNA of the invention is a duplex oligoribonucleotide in which the sense strand is derived from the mRNA sequence of the RTP801 gene, and the antisense strand is complementary to the sense strand. In general, some deviation from the target mRNA sequence is tolerated without compromising the siRNA activity (see e.g. Czauderna et al., 2003, NAR 31(11), 2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

In some embodiments the oligoribonucleotide according to the present invention comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

In one embodiment, the group of modified ribonucleotides and/or the group of flanking ribonucleotides comprise a number of ribonucleotides selected from the group consisting of an integer from 1 to 12. Accordingly, the group thus comprises one nucleotide, two nucleotides, three nucleotides, four nucleotides, five nucleotides, six nucleotides, seven nucleotides, eight nucleotides, nine nucleotides, ten nucleotides, eleven nucleotides or twelve nucleotides.

The groups of modified nucleotides and flanking nucleotides may be organized in a pattern on at least one of the strands. In some embodiments the first and second strands comprise a pattern of modified nucleotides. In another embodiment, only one strand comprises a pattern of modified nucleotides. In various embodiments the pattern of modified nucleotides of said first strand is identical relative to the pattern of modified nucleotides of the second strand.

In other embodiments the pattern of modified nucleotides of said first strand is shifted by one or more nucleotides relative to the pattern of modified nucleotides of the second strand.

In some preferred embodiments the middle ribonucleotide in the antisense strand is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this.

The modifications on the 2' moiety of the sugar residue include amino, fluoro, alkoxy e.g. methoxy, alkyl, amino, fluoro, chloro, bromo, CN, CF, imidazole, carboxylate, thioate, C, to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In some embodiments the siRNA is blunt ended, at one or both ends. More specifically, the siRNA may be blunt ended on the end defined by the 5'-terminus of the first strand and the 3'-terminus of the second strand, or the end defined by the 3'-terminus of the first strand and the 5'-terminus of the second strand. In other embodiments at least one of the two strands may have an overhang of at least one nucleotide at the 5'-terminus. At least one of the strands may also optionally have an overhang of at least one nucleotide at the 3'-terminus. The overhang may consist of from about 1 to about 5 consecutive nucleotides. A nucleotide of the overhang may be a modified or unmodified ribonucleotide or deoxyribonucleotide.

The length of RNA duplex is from about 18 to about 40 ribonucleotides, preferably 19, 21 or 23 ribonucleotides. Further, the length of each strand may independently have a length selected from the group consisting of about 15 to about 40 bases, preferably 18 to 23 bases and more preferably 19, 21 or 23 ribonucleotides.

Additionally, the complementarity between said first strand and the target nucleic acid may be perfect. In some embodiments, the strands are substantially complementary, i.e. having one, two or up to three mismatches between said first strand and the target nucleic acid. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

In certain embodiments the first strand and the second strand each comprise at least one group of modified ribonucleotides and at least one group of flanking ribonucleotides, whereby each group of modified ribonucleotides comprises at least one ribonucleotide and whereby each group of flanking ribonucleotides comprises at least one ribonucleotide, wherein each group of modified ribonucleotides of the first strand is aligned with a group of flanking ribonucleotides on the second strand, and wherein the 5' most terminal ribonucleotide is selected from a group of modified ribonucleotides, and the 3' most terminal ribonucleotide of the second strand is a selected from the group of flanking ribonucleotide.

In some embodiments each group of modified ribonucleotides consists of a single ribonucleotide and each group of flanking ribonucleotides consists of a single nucleotide.

In yet other embodiments the ribonucleotide forming the group of flanking ribonucleotides on the first strand is an unmodified ribonucleotide arranged in a 3' direction relative to the ribonucleotide forming the group of modified ribonucleotides, and the ribonucleotide forming the group of modified ribonucleotides on the second strand is a modified ribonucleotide which is arranged in 5' direction relative to the ribonucleotide forming the group of flanking ribonucleotides. In some embodiments the first strand of the siRNA comprises five to about twenty, eight to twelve, preferably nine to twelve, groups of modified ribonucleotides, and the second strand comprises seven to eleven, preferably eight to eleven, groups of modified ribonucleotides.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker or a non-nucleic acid linker. In certain embodiments a nucleic acid linker has a length of between about 2-100 nucleic acids, preferably about 2 to about 30 nucleic acids.

In various embodiments, the present invention provides a compound having the structure:
  5' $(N)_x$—Z 3' (antisense strand)
  3' Z'—$(N')_y$ 5' (sense strand)

wherein each N and N' is a ribonucleotide which may be modified or unmodified in its sugar residue; and each of $(N)_x$ and $(N')_y$ is an oligomer in which each consecutive N or N' is joined to the next N or N' by a covalent bond;

wherein each of x and y is an integer between 18 and 40;

wherein each of Z and Z' may be present or absent, but if present is 1-5 consecutive nucleotides covalently attached at the 3' terminus of the strand in which it is present;

and wherein the sequence of $(N')_y$ comprises a sense sequence having substantial identity to about 18 to about 40 consecutive ribonucleotides in an mRNA set forth in SEQ ID NO:1.

In some embodiments the compound comprises a phosphodiester bond.

In various embodiments the compound comprises ribonucleotides wherein x=y and wherein x is an integer selected from the group consisting of 18, 19, 20, 21, 22 and 23. In certain embodiments x=y=19 or x=y=23.

In some embodiments the compound is blunt ended, for example wherein Z and Z' are both absent. In an alternative embodiment, the compound comprises at least one 3' overhang, wherein at least one of Z or Z' is present. Z and Z' can be independently comprise one or more covalently linked modified or non-modified nucleotides, as described infra, for example inverted dT or dA; dT, LNA (locked nucleic acids), mirror nucleotide and the like. In some embodiments each of Z and Z' are independently selected from dT and dTdT.

In some embodiments the compound comprises one or more ribonucleotides unmodified in their sugar residues. In other embodiments the compound comprises at least one ribonucleotide modified in the sugar residue. In some embodiments the compound comprises a modification at the 2' position of the sugar residue. Modifications in the 2' position of the sugar residue include amino, fluoro, alkoxy and alkyl moieties. In certain preferred embodiments the alkoxy modification is a methoxy moiety at the 2' position of the sugar residue (2'-O-methyl; 2'-O-Me; 2'-O—$CH_3$).

In some embodiments the compound comprises modified alternating ribonucleotides in one or both of the antisense and the sense strands. In certain embodiments the compound comprises modified alternating ribonucleotides in the antisense and the sense strands. In some preferred embodiments the middle ribonucleotide of the antisense strand is not modified; e.g. ribonucleotide in position 10 in a 19-mer strand.

In various embodiments the compound comprises an antisense sequence present in Table A SEQ ID NOS:37 to 70. In other embodiments the present invention provides a mammalian expression vector comprising an antisense sequence present in Table A (SEQ ID NOS:37 to 70).

In certain embodiments the present invention provides a compound having the structure
  5' $(N)x$ 3' antisense strand
  3' $(N')y$ 5' sense strand wherein each of x and y=19 and $(N)_x$ and $(N')_y$ are fully complementary;

wherein alternating ribonucleotides in $(N)_x$ and $(N')_y$ are modified to result in a 2'-O-methyl modification in the sugar residue of the ribonucleotides;

wherein each N at the 5' and 3' termini of $(N)_x$ are modified;

wherein each N' at the 5' and 3' termini of $(N')_y$ are unmodified;

wherein each of $(N)_x$ and $(N')_y$ is selected from the group of oligomers set forth in Table A (SEQ ID NOS:3-70).

$(N)_x$ and $(N')_y$ may be phosphorylated or non-phosphorylated at the 3' and 5' termini.

In certain embodiments of the invention, alternating ribonucleotides are modified in the 2' position of the sugar residue in both the antisense and the sense strands of the compound. In particular the exemplified siRNA has been modified such that a 2'-O-methyl (Me) group was present on the first, third, fifth, seventh, ninth, eleventh, thirteenth, fifteenth, seventeenth and nineteenth nucleotide of the antisense strand, whereby the very same modification, i.e. a 2'-O-Me group, was present at the second, fourth, sixth, eighth, tenth, twelfth, fourteenth, sixteenth and eighteenth nucleotide of the sense strand. Additionally, it is to be noted that these particular siRNA compounds are also blunt ended.

In certain embodiments the present invention provides a compound having the structure
  5' $(N)x$ 3' antisense strand
  3' $(N')y$ 5' sense strand wherein each of x and y=23 and $(N)_x$ and $(N')_y$ are fully complementary wherein alternating ribonucleotides in $(N)_x$ and $(N')_y$ are modified to result in a 2'-O-methyl modification in the sugar residue of the ribonucleotides;

wherein each N at the 5' and 3' termini of $(N)_x$ are modified;

wherein each N' at the 5' and 3' termini of $(N')_y$ are unmodified;

wherein each of $(N)_x$ and $(N')_y$ is selected from the group of oligomers set forth in Table A (SEQ ID NOS:3-70).

$(N)_x$ and $(N')_y$ may be phosphorylated or non-phosphorylated at the 3' and 5' termini. In certain embodiments of the invention, alternating ribonucleotides are modified in both the antisense and the sense strands of the compound. In particular the exemplified siRNA has been modified such that a 2'-O-methyl (2'-OMe) group was present on the first, third, fifth, seventh, ninth, eleventh, thirteenth, fifteenth, seventeenth, nineteenth, twenty-first and twenty-third nucleotide of the antisense strand $(N)_x$, and whereby the very same modification, i.e. a 2'-OMe group, was present at the second, fourth, sixth, eighth, tenth, twelfth, fourteenth, sixteenth, eighteenth, twentieth and twenty-second nucleotide of the sense strand $(N')_y$. Additionally, it is to be noted that these particular siRNA compounds are also blunt ended.

In certain embodiments of the compounds of the invention having alternating ribonucleotides modified in one or both of the antisense and the sense strands of the compound; for 19-mers and 23-mers the ribonucleotides at the 5' and 3' termini of the antisense strand are modified in their sugar residues, and the ribonucleotides at the 5' and 3' termini of the sense strand are unmodified in their sugar residues. For 21-mers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

Additionally, the invention provides siRNA comprising a nucleic acid sequence set forth in Table A (SEQ ID NOS:37-70) antisense strands or a homolog thereof wherein 1, 2, or 3 of the nucleotides in one strand or both strands are substituted thereby providing at least one base pair mismatch. The substituted nucleotides in each strand are preferably in the terminal region of one strand or both strands.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

In some embodiments, neither (N)x nor (N')y are phosphorylated at the 3' and 5' termini. In other embodiments either or both (N)x and (N')y are phosphorylated at the 3' termini. Phosphorylated and unphosphorylated siRNA have similar activity and stability in vivo.

The invention further provides a vector capable of expressing any of the aforementioned oligoribonucleotides in unmodified form in a cell after which appropriate modification may be made. In preferred embodiment the cell is a mammalian cell, preferably a human cell.

More particularly, the invention provides an oligoribonucleotide wherein one strand comprises consecutive nucleotides having, from 5' to 3', the sequence set forth in any one of SEQ ID NOS:3-70, or a homolog thereof wherein in up to two of the ribonucleotides in each terminal region is altered.

Additionally, further nucleic acids according to the present invention comprise at least 14 contiguous nucleotides of any one of the polynucleotides in Table A (SEQ ID NOS:3-70) and more preferably 14 contiguous nucleotide base pairs at any end of the double-stranded structure comprised of the first strand and second strand as described above.

It will be understood by one skilled in the art that given the potential length of the nucleic acid according to the present invention and particularly of the individual strands forming such nucleic acid according to the present invention, some shifts relative to the coding sequence of the RTP801 gene to each side is possible, whereby such shifts can be up to 1, 2, 3, 4, 5 and 6 nucleotides in both directions, and whereby the thus generated double-stranded nucleic acid molecules shall also be within the present invention.

Pharmaceutical Compositions

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different siRNAs The invention further provides a pharmaceutical composition comprising at least one compound of the invention covalently or non-covalently bound to one or more compounds of the invention in an amount effective to inhibit RTP801; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to inhibit expression in a cell of the human RTP801 gene of the present invention, the compound comprising a sequence which is substantially complementary to the sequence of the RTP801 mRNA.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, the invention provides a method of inhibiting the expression of the RTP801 gene by at least 20%, preferably 30%, even more preferably 40% or even 50% as compared to a control comprising contacting an mRNA transcript of the RTP801 gene of the present invention with one or more of the compounds of the invention.

In one embodiment the oligoribonucleotide is inhibiting the RTP801 gene of the present invention, whereby the inhibition is selected from the group comprising inhibition of gene function, inhibition of polypeptide and inhibition of mRNA expression.

In one embodiment the compound inhibits the RTP801 polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In additional embodiments the invention provides a method of treating a subject suffering from a disease accompanied by an elevated level of the RTP801 gene, the method comprising administering to the subject a compound of the invention in a therapeutically effective dose thereby treating the subject.

Delivery

The siRNA molecules of the present invention may be delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Further, administration of any naked siRNA, oligonucleotide, combination of naked siRNAs or combination of naked siRNA and additional molecule in order to treat any of the diseases and conditions disclosed herein is within the scope of the present invention.

However, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual subject, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration. In addition, in certain embodiments the compositions for use in the novel treatments of the present invention may be formed as aerosols, for example for intranasal administration. In certain embodiments, oral compositions (such as tablets, suspensions, solutions) may be effective for local delivery to the oral cavity such as oral composition suitable for mouthwash for the treatment of oral mucositis.

In a particular embodiment, the administration comprises intravenous administration. In another embodiment the administration comprises topical or local administration, particularly to the eye or nose for a local or systemic effect.

In addition, in certain embodiments the compositions for use in treating disorders of the eye or CNS may be formulated for intranasal administration.

In some embodiments the compounds are useful in the treatment of an eye disorder. The compounds can be administered directly to the eye, for example in the form of eye drops, gel or ointment, for local or systemic delivery to the target cell. Accordingly, the compounds are incorporated into topical ophthalmic formulations. The compounds may be combined with opthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Preferred additives for use in sterile, isotonic solutions include, but are not limited to, benzalkonium chloride, thimerosal, chlorobutanol, sodium chloride, boric acid and mixtures thereof. In some embodiments, benzalkonium chloride or thimerosal is added as an antimicrobial preservative.

Ophthalmic formulations may contain an agent to increase solubility, (such as a surfactant), or viscosity, (such as, hydroxymethylcellulose, hydroxyethylcellulose, hydroxypropylmethylcellulose, methylcellulose, polyvinylpyrrolidone, or the like,) to improve the retention of the formulation in the conjunctival sac. Gelling agents can also be used, including, but not limited to, gellan and xanthan gum. In various embodiments an ophthalmic ointment is preferred. A sterile ophthalmic ointment formulation may be prepared by combining the active ingredient with an appropriate vehicle, such as, mineral oil, liquid lanolin, or white petrolatum and optionally a preservative. Topical formulations can include from about 0.001% by weight to about 10% by weight of the active compound with the remainder of the formulation being the carrier and other materials known in the art as topical pharmaceutical components.

Eye drops comprising a compound, in particular an siRNA compound of the present invention, are useful in targeting genes expressed in various cells and tissues of the eye. Accordingly, eye drops comprising a compound of the present invention are useful in treating age related macular degeneration, diabetic retinopathy, glaucoma.

Further, the compounds of the present invention can be administered to the eye topically or in the form of an injection, such as an intravitreal injection, a sub-retinal injection or a bilateral injection.

Further information on administration of the compounds of the present invention can be found in Tolentino et al., Retina 24 (2004) 132-138; Reich et al., Molecular vision 9 (2003) 210-216.

In another embodiment, the compounds can be administered directly to the nasal passage, for example in the form of nose drops, nasal spray, aerosol, gel or ointment, for local or systemic delivery to the target cell. Intranasal administration of a formulation comprising a compound of the present invention is useful in treating age related macular degeneration, diabetic retinopathy.

Additional systemic formulations of the compounds may also be used to treat ocular or CNS disorders. Such systemic formulations can be administered by a variety of routes including oral, transdermal, subcutaneous, intravenous, intramuscular, and intranasal. In some embodiments the compounds of the present invention are useful for treating disorders in the inner ear. Administration of the compound to the inner ear is effected by intratympanic delivery, systemic administration or alternatively via intranasal administration.

The therapeutic compositions of the present invention are preferably administered into the lung by inhalation of an aerosol containing these compositions/compounds, or by intranasal or intratracheal instillation of said compositions. Formulating the compositions in liposomes may benefit absorption. Additionally, the compositions may include a PFC liquid such as perflubron, and the compositions may be formulated as a complex of the compounds of the invention with polyethylemeimine (PEI).

For further information on pulmonary delivery of pharmaceutical compositions see Weiss et al., *Human gene therapy* 10:2287-2293 (1999); Densmore et al., *Molecular therapy* 1:180-188 (1999); Gautam et al., *Molecular therapy* 3:551-556 (2001); and Shahiwala & Misra, *AAPS PharmSciTech* 5 (2004). Additionally, respiratory formulations for siRNA are described in U.S. patent application No. 2004/0063654 of Davis et el.

An additional administration mode, particularly in connection with hearing disorders, is topical delivery of the RTP801 inhibitors onto the round window membrane of the cochlea as disclosed for example in Tanaka et al. (Hear Res. 2003 March; 177(1-2):21-31). An additional mode of administration to the ear is by trans-tympanic injection.

In the treatment of pressure sores or other wounds, the administration of the pharmaceutical composition is preferably by topical application to the damages area, but the compositions may also be administered systemically.

Additional formulations for improved delivery of the compounds of the present invention can include non-formulated compounds, compounds covalently bound to cholesterol, and compounds bound to targeting antibodies (Song et al., Antibody mediated in vivo delivery of small interfering RNAs via cell-surface receptors, Nat. Biotechnol. 2005 June; 23(6): 709-17).

Methods of Treatment

In another aspect, the present invention relates to a method for the treatment of a subject in need of treatment for a disease or disorder associated with the abnormal expression of RTP801, comprising administering to the subject an amount of an inhibitor which reduces or inhibits expression of RTP801.

In preferred embodiments the subject being treated is a warm-blooded animal and, in particular, mammals including human.

The methods of the invention comprise administering to the subject one or more inhibitory compounds which down-regulate expression of the RTP801 gene; and in particular siRNA in a therapeutically effective dose so as to thereby treat the subject.

In various embodiments the inhibitor is selected from the group consisting of siRNA, shRNA, an aptamer, an antisense molecule, miRNA, a ribozyme, and an antibody. In the presently preferred embodiments the inhibitor is siRNA.

The term "treatment" refers to both therapeutic treatment and prophylactic or preventative measures, wherein the object is to prevent or slow down (lessen) a disorder as listed above. Those in need of treatment include those already experiencing the disease or condition, those prone to having the disease or condition, and those in which the disease or condition is to be prevented. The compounds of the invention may be administered before, during or subsequent to the onset of the disease or condition or symptoms associated therewith. In cases where treatment is for the purpose of prevention, then the present invention relates to a method for delaying the onset of or averting the development of the disease or disorder.

The present invention relates to the use of compounds which down-regulate the expression of RTP801 particularly to novel small interfering RNAs (siRNAs), in the treatment of the following diseases or conditions in which inhibition of RTP801 is beneficial: hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, bone marrow, pancreas, cornea and kidney transplantation, spinal cord injury, pressure sores, age-related macular degeneration (AMD), dry eye syndrome, oral mucositis and chronic obstructive pulmonary disease (COPD). Other indications include chemical-induced nephrotoxicity and chemical-induced neurotoxicity, for example toxicity induced by cisplatin and cisplatin-like compounds, by aminoglycosides, by loop diuretics, and by hydroquinone and their analogs.

Methods, molecules and compositions which inhibit RTP801 gene are discussed herein at length, and any of said molecules and/or compositions may be beneficially employed in the treatment of a subject suffering from any of said conditions. Preferred oligomer sequences useful in the preparation of siRNA directed to RTP801 are set forth in SEQ ID NOS:3-70, listed in Table A.

The method of the invention includes administering a therapeutically effective amount of one or more compounds which down-regulate expression of RTP801, particularly the novel siRNAs of the present invention, small molecule inhibitors of RTP801 as described herein or antibodies to RTP801.

In some preferred embodiments, the methods of the invention are applied to various conditions of hearing loss. Without being bound by theory, the hearing loss may be due to apoptotic inner ear hair cell damage or loss, wherein the damage or loss is caused by infection, mechanical injury, loud sound, aging (presbycusis), or chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxin" in the context of the present invention is meant a substance that through its chemical action injures, impairs or inhibits the activity of the sound receptors component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, antineoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines, loop diuretics, and phosphodiesterase type 5 (PDE5) inhibitors such as sildenafil citrate (Viagra®).

By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

Hearing loss or impairment may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome.

The hearing loss can be noise-induced, generally due to a noise greater than 85 decibels (db) that damages the inner ear. In a particular aspect of the invention, the hearing loss is caused by an ototoxic drug that effects the auditory portion of the inner ear, particularly inner ear hair cells. Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

It is the object of the present invention to provide a method and compositions for treating a mammal, to prevent, reduce, or treat a hearing impairment, disorder or imbalance, preferably an ototoxin-induced hearing condition, by administering to a mammal in need of such treatment a composition of the invention. One embodiment of the invention is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

The methods and compositions of the present invention are especially effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2.

The methods and compositions of the present invention are also effective when the ototoxic compound is a antineoplastic agent such as vincristine, vinblastine, cisplatin and cisplatin-like compounds and taxol and taxol-like compounds.

The methods and compositions of the present invention are also effective in the treatment of acoustic trauma or mechanical trauma, preferably acoustic or mechanical trauma that leads to inner ear hair cell loss. Acoustic trauma to be treated in the present invention may be caused by a single exposure to an extremely loud sound, or following long-term exposure to everyday loud sounds above 85 decibels. Mechanical inner ear trauma to be treated in the present invention is for example the inner ear trauma following an operation of electronic device insertion in the inner ear. The compositions of the present invention prevent or minimize the damage to inner ear hair cells associated with the operation.

In some embodiments the composition of the invention is co-administered with an ototoxin. For example, an improved method is provided for treatment of infection of a mammal by administration of an aminoglycoside antibiotic, the improvement comprising administering a therapeutically effective amount of one or more compounds (particularly novel siRNA compounds) which down-regulate expression of RTP801, to the subject in need of such treatment to reduce or prevent ototoxin-induced hearing impairment associated with the antibiotic. The compounds which down-regulate expression of RTP801 particularly novel siRNA compounds are preferably administered locally within the inner ear.

In yet another embodiment an improved method for treatment of cancer in a mammal by administration of a chemotherapeutic compound is provided, wherein the improvement comprises administering a therapeutically effective amount of a composition of the invention to the subject in need of such treatment to reduce or prevent ototoxin-induced hearing impairment associated with the chemotherapeutic drug. The compounds which reduce or prevent the ototoxin-induced hearing impairment, e.g. the novel siRNA compounds inter alia are preferably administered locally within the inner ear.

In another embodiment the methods of treatment are applied to treatment of hearing loss resulting from the administration of a chemotherapeutic agent in order to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include carboplatin (Paraplatin®), tetraplatin, oxaliplatin, aroplatin and transplatin inter alia.

In another embodiment the methods of the invention are applied to hearing impairments resulting from the administration of quinine and its synthetic substitutes, typically used in the treatment of malaria, to treat its ototoxic side-effect.

In another embodiment the methods of the invention are applied to hearing impairments resulting from administration of a diuretic to treat its ototoxic side-effect. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in non-edematous states for example hypertension, hypercalcemia, idiopathic hypercalciuria, and nephrogenic diabetes insipidus.

In another preferred embodiment, the compounds of the invention are used for treating acute renal failure, in particular acute renal failure due to ischemia in post surgical patients, and acute renal failure due to chemotherapy treatment such as cisplatin administration or sepsis-associated acute renal failure. A preferred use of the compounds of the invention is for the prevention of acute renal failure in high-risk patients undergoing major cardiac surgery or vascular surgery. The patients at high-risk of developing acute renal failure can be identified using various scoring methods such as the Cleveland Clinic algorithm or that developed by US Academic Hospitals (QMMI) and by Veterans' Administration (CICSS). Other preferred uses of the compounds of the invention are for the prevention of ischemic acute renal failure in kidney transplant patients or for the prevention of toxic acute renal failure in patients receiving chemotherapy.

In another preferred embodiment, the compounds of the invention are used for treating glaucoma. Main types of glaucoma are primary open angle glaucoma (POAG), angle closure glaucoma, normal tension glaucoma and pediatric glaucoma. These are marked by an increase of intraocular pressure (IOP), or pressure inside the eye. When optic nerve damage has occurred despite a normal IOP, this is called normal tension glaucoma. Secondary glaucoma refers to any case in which another disease causes or contributes to increased eye pressure, resulting in optic nerve damage and vision loss.

In another preferred embodiment, the compounds of the invention are used for treating or preventing the damage caused by nephrotoxins such as diuretics, β-blockers, vasodilator agents, ACE inhibitors, cyclosporin, aminoglycoside antibiotics (e.g. gentamicin), amphotericin B, cisplatin, radiocontrast media, immunoglobulins, mannitol, NSAIDs (eg aspirin, ibuprofen, diclofenac), cyclophosphamide, methotrexate, aciclovir, polyethylene glycol, β-lactam antibiotics, vancomycin, rifampicin, sulphonamides, ciprofloxacin, ranitidine, cimetidine, furosemide, thiazides, phenyloin, penicillamine, lithium salts, fluoride, demeclocycline, foscarnet, aristolochic acid.

In another preferred embodiment, the compounds of the invention are used for treating or preventing the damage caused by spinal-cord injury especially spinal cord trauma caused by motor vehicle accidents, falls, sports injuries, industrial accidents, gunshot wounds, spinal cord trauma caused by spine weakening (such as from rheumatoid arthritis or osteoporosis) or if the spinal canal protecting the spinal cord has become too narrow (spinal stenosis) due to the normal aging process, direct damage that occur when the spinal cord is pulled, pressed sideways, or compressed, damage to the spinal-cord following bleeding, fluid accumulation, and swelling inside the spinal cord or outside the spinal cord (but within the spinal canal).

The compounds of the invention are also used for treating or preventing the damage caused by spinal-cord injury due to disease such as polio or spina bifida. In other embodiments the compounds and methods of the invention are useful for treating or preventing the incidence or severity of acute lung injury, in particular conditions which result from ischemic/reperfusion injury or oxidative stress. For example, acute respiratory distress syndrome (ARDS) due to coronavirus infection or endotoxins, severe acute respiratory syndrome (SARS), ischemia reperfusion injury associated with lung transplantation and other acute lung injuries.

In other embodiments the compounds and methods of the invention are useful for treating or preventing damage following organ transplantation including lung, liver, heart, bone pancreas, intestine, skin, blood vessels, heart valve, bone and kidney transplantation.

The term "organ transplant" is meant to encompass transplant of any one or more of the following organs including, inter alia, lung, kidney, heart, skin, vein, bone, cartilage, liver transplantation. Although a xenotransplant can be contemplated in certain situations, an allotransplant is usually preferable. An autograft can be considered for bone marrow, skin, bone, cartilage and or blood vessel transplantation.

The siRNA compounds of the present invention are particularly useful in treating a subject experiencing the adverse effects of organ transplant, including ameliorating, treating or preventing perfusion injury.

For organ transplantation, either the donor or the recipient or both may be treated with a compound or composition of the present invention. Accordingly, the present invention relates to a method of treating an organ donor or an organ recipient comprising the step of administering to the organ donor or organ recipient a therapeutically effective amount of a compound according to the present invention.

The invention further relates to a method for preserving an organ comprising contacting the organ with an effective amount of compound of the present invention. Also provided is a method for reducing or preventing injury (in particular reperfusion injury) of an organ during surgery and/or following removal of the organ from a subject comprising placing the organ in an organ preserving solution wherein the solution comprises a compound according to the present invention.

In other embodiments the compounds and methods of the invention are useful for treating or preventing the incidence or severity of other diseases and conditions in a patient. These diseases and conditions include stroke and stroke-like situations (e.g. cerebral, renal, cardiac failure), neuronal cell death, brain injuries with or without reperfusion issues, chronic degenerative diseases e.g. neurodegenerative disease including Alzheimer's disease, Huntington's disease, Parkinson's disease, multiple sclerosis, amyotrophic lateral sclerosis, spinobulbar atrophy, prion disease, and apoptosis resulting from traumatic brain injury (TBI).

The compounds and methods of the invention are directed to providing neuroprotection, or to provide cerebroprotection, or to prevent and/or treat cytotoxic T cell and natural killer cell-mediated apoptosis associated with autoimmune disease and transplant rejection, to prevent cell death of cardiac cells including heart failure, cardiomyopathy, viral infection or bacterial infection of heart, myocardial ischemia, myocardial infarct, and myocardial ischemia, coronary artery by-pass graft, to prevent and/or treat mitochondrial drug toxicity e.g. as a result of chemotherapy or HIV therapy, to prevent cell death during viral infection or bacterial infection, or to prevent and/or treat inflammation or inflammatory diseases, inflammatory bowel disease, sepsis and septic shock, or to prevent cell death from follicle to oocyte stages, from oocyte to mature egg stages and sperm (for example, methods of freezing and transplanting ovarian tissue, artificial fertilization), or to preserve fertility in mammals after chemotherapy, in particular human mammals, or to prevent and/or treat, macular degeneration, or to prevent and/or treat acute hepatitis, chronic active hepatitis, hepatitis-B, and hepatitis-C, or to prevent hair loss, (e.g. hair loss due-to male-pattern baldness, or hair loss due to radiation, chemotherapy or emotional stress), or to treat or ameliorate skin damage whereby the skin damage may be due to exposure to high levels of radiation, heat, chemicals, sun, or to burns and autoimmune diseases), or to prevent cell death of bone marrow cells in myelodysplastic syndromes (MDS), to treat pancreatitis, to treat rheumatoid arthritis, psoriasis, glomerulonephritis, atherosclerosis, and graft versus host disease (GVHD), or to treat retinal pericyte apoptosis, retinal damages resulting from ischemia, diabetic retinopathy, or to treat any disease states associated with an increase of apoptotic cell death.

The present invention also provides for a process of preparing a pharmaceutical composition, which comprises:

providing one or more double stranded compound of the invention; and admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Conditions to be Treated

Chronic Obstructive Pulmonary Disease (COPD)

Chronic obstructive pulmonary disease (COPD), affects more than 16 million Americans and is the fourth highest cause of death in the United States. Cigarette smoking causes most occurrences of the debilitating disease but other environmental factors cannot be excluded (Petty T L. 2003. Clin. Cornerstone, 5-10).

Pulmonary emphysema is a major manifestation of COPD. Permanent destruction of peripheral air spaces, distal to terminal bronchioles, is the hallmark of emphysema (Tuder, et al. *Am J Respir Cell Mol Biol*, 29:88-97; 2003.). Emphysema is also characterized by accumulation of inflammatory cells such as macrophages and neutrophils in bronchioles and alveolar structures (Petty, 2003).

The pathogenesis of emphysema is complex and multifactorial. In humans, a deficiency of inhibitors of proteases produced by inflammatory cells, such as alpha1-antitrypsin, has been shown to contribute to protease/antiprotease imbalance, thereby favoring destruction of alveolar extracellular matrix in cigarette-smoke (CS) induced emphysema (Eriksson, S. 1964. Acta Med Scand 175:197-205. Joos, L., Pare, P. D., and Sandford, A. J. 2002. Swiss Med Wkly 132:27-37). Matrix metalloproteinases (MMPs) play a central role in experimental emphysema, as documented by resistance of macrophage metalloelastase knockout mice against emphysema caused by chronic inhalation of CS (Hautamaki, et al: Requirement for macrophage elastase for cigarette smoke-induced emphysema in mice. Science 277:2002-2004). Moreover, pulmonary overexpression of interleukin-13 in transgenic mice results in MMP- and cathepsin-dependent emphysema (Zheng, T., et al 2000. J Clin Invest 106:1081-1093). Oxidative stress and apoptosis interact and cause emphysema due to vascular endothelial growth factor blocade. Am J Respir Cell Mol Biol, 29:88-97; 2003.; Yokohori N, Aoshiba K, Nagai A, Chest. 2004 February; 125(2):626-32.; Aoshiba K, Yokohori N, Nagai A., Am J Respir Cell Mol. Biol. 2003 May; 28(5): 555-62.). Both reactive oxygen species (ROS) from inhaled cigarette smoke and those endogenously formed by inflammatory cells contribute to an increased intrapulmonary oxidant burden.

An additional pathogenic factor with regards to COPD pathogenesis is the observed decreased expression of VEGF and VEGFR11 in lungs of emphysematous patients (Yasunori Kasahara, Rubin M. Tuder, Carlyne D. Cool, David A. Lynch, Sonia C. Flores, and Norbert F. Voelkel. *Am J Respir Crit. Care Med Vol* 163. pp 737-744, 2001). Moreover, inhibition of VEGF signaling using chemical VEGFR inhibitor leads to alveolar septal endothelial and then to epithelial cell apoptosis, probably due to disruption of intimate structural/functional connection of both types of cells within alveoli (Yasunori Kasahara, Rubin M. Tuder, Laimute Taraseviciene-Stewart, Timothy D. Le Cras, Steven Abman, Peter K. Hirth, Johannes Waltenberger, and Norbert F. Voelkel. *J. Clin. Invest.* 106:1311-1319 (2000).; Voelkel N F, Cool C D. *Eur Respir J. Suppl.* 2003 November; 46:28s-32s).

Macular Degeneration

The most common cause of decreased best-corrected vision in individuals over 65 years of age in the US is the retinal disorder known as age-related macular degeneration (AMD). As AMD progresses, the disease is characterized by loss of sharp, central vision. The area of the eye affected by AMD is the Macula—a small area in the center of the retina, composed primarily of photoreceptor cells. So-called "dry" AMD, accounting for about 85%-90% of AMD patients, involves alterations in eye pigment distribution, loss of photoreceptors and diminished retinal function due to overall atrophy of cells. So-called "wet" AMD involves proliferation of abnormal choroidal vessels leading to clots or scars in the sub-retinal space. Thus, the onset of wet AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, *Frontiers in Bioscience*, e305-314, May 2003). CNV occurs not only in wet AMD but also in other ocular pathologies such as ocular histoplasmosis syndrome, angiod streaks, ruptures in Bruch's membrane, myopic degeneration, ocular tumors and some retinal degenerative diseases.

siRNA molecules inhibiting VEGF and VEGF-R1 (Flt-1), respectively, for treatment of AMD are in clinical trials (Acuity Pharmaceuticals and Sirna Therapeutics).

Microvascular Disorders

Microvascular disorders are composed of a broad group of conditions that primarily affect the microscopic capillaries and lymphatics and are therefore outside the scope of direct surgical intervention. Microvascular disease can be broadly grouped into the vasospastic, the vasculitis and lymphatic occlusive. Additionally, many of the known vascular conditions have a microvascular element to them.

Vasospastic Disease—Vasospastic diseases are a group of relatively common conditions where, for unknown reasons, the peripheral vasoconstrictive reflexes are hypersensitive. This results in inappropriate vasoconstriction and tissue ischaemia, even to the point of tissue loss. Vasospastic symptoms are usually related to temperature or the use of vibrating machinery but may be secondary to other conditions.

Vasculitic Disease—Vasculitic diseases are those that involve a primary inflammatory process in the microcirculation. Vasculitis is usually a component of an autoimmune or connective tissue disorder and is not generally amenable to surgical treatment but requires immunosuppressive treatment if the symptoms are severe.

Lymphatic Occlusive Disease—Chronic swelling of the lower or upper limb (lymphoedema) is the result of peripheral lymphatic occlusion. This is a relatively rare condition that has a large number of causes, some inherited, some acquired. The mainstays of treatment are correctly fitted compression garments and the use of intermittent compression devices.

Microvascular Pathologies Associated with Diabetes

Diabetes is the leading cause of blindness, the number one cause of amputations and impotence, and one of the most frequently occurring chronic childhood diseases. Diabetes is also the leading cause of end-stage renal disease in the United States, with a prevalence rate of 31% compared with other renal diseases. Diabetes is also the most frequent indication for kidney transplantation, accounting for 22% of all transplantation operations.

In general, diabetic complications can be classified broadly as microvascular or macrovascular disease. Microvascular complications include neuropathy (nerve damage), nephropathy (kidney disease) and vision disorders (eg retinopathy, glaucoma, cataract and corneal disease). In the retina, glomerulus, and vasa nervorum, similar pathophysiologic features characterize diabetes-specific microvascular disease.

For further information, see Larsen: Williams Textbook of Endocrinology, 10th ed., Copyright®2003 Elsevier.

Microvascular complications occur not only in overt diabetes but are also due to Impaired Glucose Tolerance (IGT). Microvascular complications of IGT: neuropathy, retinopathy, and renal microproteinuria.

Diabetic Neuropathy

Diabetic neuropathies are neuropathic disorders (peripheral nerve damage) that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy and the most common form, peripheral neuropathy, which mainly affects the feet and legs. There are four factors involved in the development of diabetic neuropathy: microvascular disease, advanced glycated end products, protein kinase C, and the polyol pathway.

Microvascular Disease in Diabetic Neuropathy

Neuropathy is a common complication of diabetes occurring over time in more than half of patients with type 2 diabetes. Nerve conduction studies demonstrate that neuropathy is already present in 10-18% of patients at the time of diabetes diagnosis, suggesting that peripheral nerve injury occurs at early stages of disease and with milder glycemic dysregulation. The concept that neuropathy is an early clinical sign of diabetes was proposed >40 years ago, and most studies report an association between IGT and neuropathy. Most patients with IGT and associated neuropathy have a symmetric, distal sensory polyneuropathy with prominent neuropathic pain. IGT neuropathy (Robinson Singleton, *Perspectives in Diabetes*, in *Diabetes* Dec. 1, 2003) is phenotypically similar to early diabetic neuropathy, which also causes sensory symptoms, including pain, and autonomic dysfunction. In a survey of 669 patients with early diabetic neuropathy, sensory symptoms were present in >60%, impotence in nearly 40%, and other autonomic involvement in 33%, but evidence of motor involvement in only 12%. These clinical findings suggest prominent early involvement of the small unmyelinated nerve fibers that carry pain, temperature, and autonomic signals. Direct quantitation of unmyelinated intraepidermal nerve fibers from skin biopsies shows similar fiber loss and altered morphology in patients with neuropathy associated with IGT and early diabetes.

Nerve damage in diabetes affects the motor, sensory, and autonomic fibers. Motor neuropathy causes muscle weakness, atrophy, and paresis. Sensory neuropathy leads to loss of the protective sensations of pain, pressure, and heat. The absence of pain leads to many problems in the insensate foot, including ulceration, unperceived trauma, and Charcot neuroarthropathy.

Sensorimotor Polyneuropathy

Longer nerve fibers are affected to a greater degree than shorter ones, because nerve conduction velocity is slowed in proportion to a nerve's length. In this syndrome, decreased sensation and loss of reflexes occurs first in the toes bilaterally, then extends upward. It is usually described as glove-stocking distribution of numbness, sensory loss, dysesthesia and nighttime pain. The pain can feel like burning, pricking sensation, achy or dull. Pins and needles sensation is common. Loss of proprioception, that is, the sense of where a limb is in space, is affected early. These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle or foot, and develop a Charcot joint. Loss of motor function results on dorsiflexion contractures of the toes, so called hammertoes. These contractures occur not only in the foot but also in the hand.

Autonomic Neuropathy

The autonomic nervous system is composed of nerves serving the heart, GI tract and urinary system. Autonomic neuropathy can affect any of these organ systems. The most commonly recognized autonomic dysfunction in diabetics is orthostatic hypotension, or the uncomfortable sensation of fainting when a patient stands up. In the case of diabetic autonomic neuropathy, it is due to the failure of the heart and arteries to appropriately adjust heart rate and vascular tone to keep blood continually and fully flowing to the brain. This symptom is usually accompanied by a loss of sinus respiratory variation, that is, the usual change in heart rate seen with normal breathing. When these two findings are present, cardiac autonomic neuropathy is present.

GI tract manifestations include delayed gastric emptying, gastroparesis, nausea, bloating, and diarrhea. Because many diabetics take oral medication for their diabetes, absorption of these medicines is greatly affected by the delayed gastric emptying. This can lead to hypoglycemia when an oral diabetic agent is taken before a meal and does not get absorbed until hours, or sometimes days later, when there is normal or low blood sugar already. Sluggish movement of the small intestine can cause bacterial overgrowth, made worse by the presence of hyperglycemia. This leads to bloating, gas and diarrhea.

Urinary symptoms include urinary frequency, urgency, incontinence and retention. Again, because of the retention of sweet urine, urinary tract infections are frequent. Urinary retention can lead to bladder diverticula, stones, reflux nephropathy.

Cranial Neuropathy

When cranial nerves are affected, oculomotor (3rd) neuropathies are most common. The oculomotor nerve controls all of the muscles that move the eye with the exception of the lateral rectus and superior oblique muscles. It also serves to constrict the pupil and open the eyelid. The onset of a diabetic third nerve palsy is usually abrupt, beginning with frontal or periorbital pain and then diplopia. All of the oculomotor muscles innervated by the third nerve may be affected, except for those that control pupil size. The sixth nerve, the abducens nerve, which innervates the lateral rectus muscle of the eye (moves the eye laterally), is also commonly affected but fourth nerve, the trochlear nerve, (innervates the superior oblique muscle, which moves the eye downward) involvement is unusual. Mononeuropathies of the thoracic or lumbar spinal nerves can occur and lead to painful syndromes that mimic myocardial infarction, cholecystitis or appendicitis. Diabetics have a higher incidence of entrapment neuropathies, such as carpal tunnel syndrome.

Diabetic Limb Ischemia and Diabetic Foot Ulcers

Diabetes and pressure can impair microvascular circulation and lead to changes in the skin on the lower extremities, which in turn, can lead to formation of ulcers and subsequent infection. Microvascular changes lead to limb muscle microangiopathy, as well as a predisposition to develop peripheral ischemia and a reduced angiogenesis compensatory response to ischemic events. Microvascular pathology exacerbates Peripheral Vascular Disease (PVD) (or Peripheral Arterial Disease (PAD) or Lower Extremity Arterial Disease (LEAD)—a MACROvascular complication—narrowing of the arteries in the legs due to atherosclerosis. PVD occurs earlier in diabetics, is more severe and widespread, and often involves intercurrent microcirculatory problems affecting the legs, eyes, and kidneys.

Foot ulcers and gangrene are frequent comorbid conditions of PAD. Concurrent peripheral neuropathy with impaired sensation make the foot susceptible to trauma, ulceration, and infection. The progression of PAD in diabetes is compounded by such comorbidity as peripheral neuropathy and insensitivity of the feet and lower extremities to pain and trauma. With impaired circulation and impaired sensation, ulceration and infection occur. Progression to osteomyelitis and gangrene may necessitate amputation. Persons with diabetes are up to 25 times more likely than nondiabetic persons to sustain a lower limb amputation, underscoring the need to prevent foot ulcers and subsequent limb loss.

For further information, see American Journal of Surgery, Volume 187•Number 5 Suppl 1•May 1, 2004, Copyright© 2004 Elsevier.

Coronary Microvascular Dysfunction in Diabetes

The correlation between histopathology and microcirculatory dysfunction in diabetes is well known from old experimental studies and from autopsy, where thickening of the basal membrane, perivascular fibrosis, vascular rarefication, and capillary hemorrhage are frequently found. It remains difficult to confirm these data in vivo, although a recent paper demonstrated a correlation between pathology and ocular micorvascular dysfunction (Am J Physiol 2003; 285). A large amount of clinical studies, however, indicate that not only overt diabetes but also impaired metabolic control may affect coronary microcirculation (Hypert Res 2002; 25:893). Sambuceti et al (Circulation 2001; 104:1129) shown the persistence of microvascular dysfunction in patients after successful reopening of the infarct related artery, and which may explain the increased cardiovascular morbidity and mortality in these patients. There is mounting evidence from large acute reperfusion studies that morbidity and mortality are unrelated to the reopening itself of the infarct related artery, but much more dependent on the TIMI flow+/− myocardial blush (Stone 2002; Feldmann Circulation 2003). Herrmann indicated, among others, that the integrity of the coronary microcirculation is probably the most important clinical and prognostic factor in this context (Circulation 2001). The neutral effect of protection devices (no relevant change for TIMI flow, for ST resolution, or for MACE) may indicate that a functional impairment of microcirculation is the major determinant of prognosis. There is also increasing evidence that coronary microvascular dysfunction plays a major role in non obstructive CAD. Coronary endothelial dysfunction remains a strong prognostic predictor in these patients.

Diabetic Nephropathy (Renal Dysfunction in Patients with Diabetes)

Diabetic nephropathy encompasses microalbuminuria (a microvascular disease effect), proteinuria and ESRD. Diabetes is the most common cause of kidney failure, accounting for more than 40 percent of new cases. Even when drugs and diet are able to control diabetes, the disease can lead to nephropathy and kidney failure. Most people with diabetes do not develop nephropathy that is severe enough to cause kidney failure. About 16 million people in the United States have diabetes, and about 100,000 people have kidney failure as a result of diabetes.

Diabetic Retinopathy

In the diabetic state, hyperglycemia leads to decreased retinal blood flow, retinal hyperpermeability, delays in photoreceptor nerve conduction, and retinal neuronal cell death. In short duration diabetes, neuronal cell death has been identified within the inner nuclear layer of the retina. Specifically, apoptosis has been localized to glial cells such as Mueller cells and astrocytes and has been shown to occur within 1 month of diabetes in the STZ-induced diabetic rat model. The cause of these events is multi-factorial including activation of the diacylglycerol/PKC pathway, oxidative stress, and non-enzymatic glycosylation. The combination of these events renders the retina hypoxic and ultimately leads to the development of diabetic retinopathy. One possible connection between retinal ischemia and the early changes in the diabetic retina is the hypoxia-induced production of growth factors such as VEGF. The master regulator of the hypoxic response has been identified as hypoxia inducible factor-1 (HIF-1), which controls genes that regulate cellular proliferation and angiogenesis. Prior studies have demonstrated that inhibition of HIF-1 ubiquitination leads to binding with hypoxia responsive elements (HRE) and production of VEGF mRNA.

Diabetic Retinopathy is defined as the progressive dysfunction of the retinal vasculature caused by chronic hyperglycemia. Key features of diabetic retinopathy include microaneurysms, retinal hemorrhages, retinal lipid exudates, cotton-wool spots, capillary nonperfusion, macular edema and neovascularization. Associated features include vitreous hemorrhage, retinal detachment, neovascular glaucoma, premature cataract and cranial nerve palsies.

Diabetic Macular Edema (DME)

DME is a complication of diabetic retinopathy, a disease affecting the blood vessels of the retina. Diabetic retinopathy results in multiple abnormalities in the retina, including retinal thickening and edema, hemorrhages, impeded blood flow, excessive leakage of fluid from blood vessels and, in the final stages, abnormal blood vessel growth. This blood vessel growth can lead to large hemorrhages and severe retinal damage. When the blood vessel leakage of diabetic retinopathy causes swelling in the macula, it is referred to as DME. The principal symptom of DME is a loss of central vision. Risk factors associated with DME include poorly controlled blood glucose levels, high blood pressure, abnormal kidney function causing fluid retention, high cholesterol levels and other general systemic factors.

According to the World Health Organization, diabetic retinopathy is the leading cause of blindness in working age adults and a leading cause of vision loss in diabetics. The American Diabetes Association reports that there are approximately 18 million diabetics in the United States and approximately 1.3 million newly diagnosed cases of diabetes in the United States each year. Prevent Blindness America and the National Eye Institute estimate that in the United States there are over 5.3 million people aged 18 or older with diabetic retinopathy, including approximately 500,000 with DME. The CDC estimates that there are approximately 75,000 new cases of DME in the United States each year.

Additional Neuropathies

In addition to diabetes, the common causes of neuropathy are herpes zoster infection, chronic or acute trauma (including surgery) and various neurotoxins. Neuropathic pain is common in cancer as a direct result of the cancer on peripheral nerves (e.g., compression by a tumor) and as a side effect of many chemotherapy drugs.

Microvascular disease—Vascular and neural diseases are closely related and intertwined. Blood vessels depend on normal nerve function, and nerves depends on adequate blood flow. The first pathological change in the microvasculature is vasoconstriction. As the disease progresses, neuronal dysfunction correlates closely with the development of vascular abnormalities, such as capillary basement membrane thickening and endothelial hyperplasia, which contribute to diminished oxygen tension and hypoxia. Vasodilator agents (e.g., angiotensin-converting-enzyme inhibitors, $\alpha$1-antagonists) can lead to substantial improvements in neuronal blood flow, with corresponding improvements in nerve conduction velocities.

Clinical Manifestations

Neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination.

Despite advances in the understanding of the metabolic causes of neuropathy, treatments aimed at interrupting these pathological processes have been limited by side effects and lack of efficacy. Thus, treatments are symptomatic and do not address the underlying problems. Agents for pain caused by sensorimotor neuropathy include tricyclic antidepressants (TCAs), serotonin reuptake inhibitors (SSRIs) and antiepileptic drugs (AEDs). None of these agents reverse the pathological processes leading to diabetic neuropathy and none alter the relentless course of the illness. Thus, it would be useful to have a pharmaceutical composition that could better treat these conditions and/or alleviate the symptoms.

Additional Retinopathies

Retinal Microvasculopathy (AIDS Retinopathy)

Retinal microvasculopathy is seen in 100% of AIDS patients. It is characterized by intraretinal hemorrhages, microaneurysms, Roth spots, cotton-wool spots (microinfarctions of the nerve fiber layer) and perivascular sheathing. The etiology of the retinopathy is unknown though it has been thought to be due to circulating immune complexes, local release of cytotoxic substances, abnormal hemorheology, and HIV infection of endothelial cells. AIDS retinopathy is now so common that cotton wool spots in a patient without diabetes or hypertension but at risk for HIV should prompt the physician to consider viral testing. There is no specific treatment for AIDS retinopathy but its continued presence may prompt a physician to reexamine the efficacy of the HIV therapy and patient compliance.

Bone Marrow Transplantation (BMT) Retinopathy

Bone marrow transplantation retinopathy was first reported in 1983. It typically occurs within six months, but it can occur as late as 62 months after BMT. Risk factors such as diabetes and hypertension may facilitate the development of BMT retinopathy by heightening the ischemic microvasculopathy. There is no known age, gender or race predilection for development of BMT retinopathy. Patients present with decreased visual acuity and/or visual field deficit. Posterior segment findings are typically bilateral and symmetric. Clinical manifestations include multiple cotton wool spots, telangiectasia, microaneurysms, macular edema, hard exudates and retinal hemorrhages. Fluorescein angiography demonstrates capillary nonperfusion and dropout, intraretinal microvascular abnormalities, microaneurysms and macular edema. Although the precise etiology of BMT retinopathy has not been elucidated, it appears to be affected by several factors: cyclosporine toxicity, total body irradiation (TBI), and chemotherapeutic agents. Cyclosporine is a powerful immunomodulatory agent that suppresses graft-versus-host immune response. It may lead to endothelial cell injury and neurologic side effects, and as a result, it has been suggested as the cause of BMT retinopathy. However, BMT retinopathy can develop in the absence of cyclosporine use, and cyclosporine has not been shown to cause BMT retinopathy in autologous or syngeneic bone marrow recipients. Cyclosporine does not, therefore, appear to be the sole cause of BMT retinopathy. Total body irradiation (TBI) has also been implicated as the cause of BMT retinopathy. Radiation injures the retinal microvasculature and leads to ischemic vasculopathy.

Ischemic Conditions

Ischemic injury is the most common clinical expression of cell injury by oxygen deprivation. The most useful models for studying ischemic injury involve complete occlusion of one of the end-arteries to an organ (e.g., a coronary artery) and examination of the tissue (e.g., cardiac muscle) in areas supplied by the artery. Complex pathologic changes occur in diverse cellular systems during ischemia. Up to a certain point, for a duration that varies among different types of cells, the injury may be amenable to repair, and the affected cells may recover if oxygen and metabolic substrates are again made available by restoration of blood flow. With further extension of the ischemic duration, cell structure continues to deteriorate, owing to relentless progression of ongoing injury mechanisms. With time, the energetic machinery of the cell—the mitochondrial oxidative powerhouse and the glycolytic pathway—becomes irreparably damaged, and restoration of blood flow (reperfusion) cannot rescue the damaged cell. Even if the cellular energetic machinery were to remain intact, irreparable damage to the genome or to cellular membranes will ensure a lethal outcome regardless of reperfusion. This irreversible injury is usually manifested as necrosis, but apoptosis may also play a role. Under certain circumstances, when blood flow is restored to cells that have been previously made ischemic but have not died, injury is often paradoxically exacerbated and proceeds at an accelerated pace—this is reperfusion injury.

Reperfusion injury may occur in a variety of conditions, especially during medical intervention, including but not limited to angioplasty, cardiac surgery or thrombolysis; organ transplant; as a result of plastic surgery; during severe compartment syndrome; during re-attachment of severed limbs; as a result of multiorgan failure syndrome; in the brain as a result of stroke or brain trauma; in connection with chronic wounds such as pressure sores, venous ulcers and diabetic ulcers; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal failure as observed after renal transplantation, major surgery, trauma, and septic as well as hemorrhagic shock; Sepsis; Retinal ischemia occurring as a result of acute vascular occlusion, leading to loss of vision in a number of ocular diseases such as acute glaucoma, diabetic retinopathy, hypertensive retinopathy, and retinal vascular occlusion; Cochlear ischemia; flap failure in microvascular surgery for head and neck defects; Raynaud's phenomenon and the associated digital ischemic lesions in scleroderma; spinal cord injury; vascular surgery; Traumatic rhabdomyolysis (crush syndrome); and myoglobinuria.

Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor; and diseases such as stroke, Parkinson's disease, epilepsy, depression, ALS, Alzheimer's disease, Huntington's disease and any other disease-induced dementia (such as HIV induced dementia for example).

Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracarnial hematoma or edema). Similarly, traumatic constriction or compression can arise from the presence of a mass of abnormal tissue, such as a metastatic or primary tumor.

In conclusion, current modes of therapy for the prevention and/or treatment of COPD, macular degeneration microvascular diseases and ototoxic conditions are unsatisfactory and there is a need therefore to develop novel compounds for this purpose. There is also a need to develop a therapy and a medicament which can treat the ototoxic effects currently associated with certain drugs and conditions, in particular with cisplatin chemotherapeutics and certain antibiotics without sacrificing the effectiveness of the drugs. Additionally, there is a need to develop a therapy and medicament which can treat the ototoxic effects associated with acoustic trauma or mechanical trauma within the inner ear. Furthermore, there is a need to develop a therapy and a medicament for the treatment of pressure sores, ischemia and ischemia-reperfusion related conditions. All the diseases and indications disclosed herein above, as well as other diseases and conditions described herein such as MI may also be treated by the novel compounds of this invention.

Post Stroke Dementia

About 25% of people have dementia after a stroke with many others developing dementia over the following 5 to 10 years. In addition, many individuals experience more subtle impairments of their higher brain functions (such as planning skills and speed of processing information) and are at very high risk of subsequently developing dementia. Very small strokes in the deep parts of the brain in this process (called microvascular disease) seem to be essential in the process leading to an identified pattern of brain atrophy specific to post-stroke dementia.

Ocular Ischemic Syndrome

Patients suffering from ocular ischemic syndrome (OIS) are generally elderly, ranging in age from the 50 s to 80 s. Males are affected twice as commonly as females. The patient is only rarely asymptomatic. Decreased vision occurs at presentation in 90 percent of cases, and 40 percent of patients have attendant eye pain. There may also be an attendant or antecedent history of transient ischemic attacks or amaurosis fugax. Patients also have significant known or unknown systemic disease at the time of presentation. The most commonly encountered systemic diseases are hypertension, diabetes, ischemic heart disease, stroke, and peripheral vascular disease. To a lesser extent, patients manifest OIS as a result of giant cell arteritis (GCA).

Unilateral findings are present in 80 percent of cases. Common findings may include advanced unilateral cataract, anterior segment inflammation, asymptomatic anterior chamber reaction, macular edema, dilated but non-tortuous retinal veins, mid-peripheral dot and blot hemorrhages, cotton wool spots, exudates, and neovascularization of the disc and retina. There may also be spontaneous arterial pulsation, elevated intraocular pressure, and neovascularization of the iris and angle with neovascular glaucoma (NVG). While the patient may exhibit anterior segment neovascularization, ocular hypotony may occur due to low arterial perfusion to the ciliary body. Occasionally, there are visible retinal emboli (Hollenhorst plaques).

The findings in OIS are caused by internal carotid artery atheromatous ulceration and stenosis at the bifurcation of the common carotid artery. Five percent of patients with internal artery stenosis develop OIS. However, OIS only occurs if the degree of stenosis exceeds 90 percent. Stenosis of the carotid artery reduces perfusion pressure to the eye, resulting in the above-mentioned ischemic phenomena. Once stenosis reaches 90 percent, the perfusion pressure in the central retinal artery (CRA) drops only to 50 percent. Often, the reduced arterial pressure manifests as spontaneous pulsation of the CRA. The findings are variable and may include any or all of the above findings.

Patients with OIS have significant systemic disease that must be assessed. Cardiac death is the primary cause of mortality in patients with OIS—the five-year mortality rate is 40 percent.

Microvascular Diseases of the Kidney

The kidney is involved in a number of discreet clinicopathologic conditions that affect systemic and renal microvasculature. Certain of these conditions are characterized by primary injury to endothelial cells, such as:

hemolytic-uremic syndrome (HUS) and thrombotic thrombocytopenic purpura (TTP) HUS and TTP are closely related diseases characterized by microangiopathic hemolytic anemia and variable organ impairment Traditionally, the diagnosis of HUS is made when renal failure is a predominant feature of the syndrome, as is common in children. In adults, neurologic impairment frequently predominates and the syndrome is then referred to as TTP. Thrombotic microangiopathy is the underlying pathologic lesion in both syndromes, and the clinical and laboratory findings in patients with either HUS or TTP overlap to a large extent. This has prompted several investigators to regard the two syndromes as a continuum of a single disease entity. Pathogenesis: Experimental data strongly suggest that endothelial cell injury is the primary event in the pathogenesis of HUS/TTP. Endothelial damage triggers a cascade of events that includes local intravascular coagulation, fibrin deposition, and platelet activation and aggregation. The end result is the histopathologic finding of thrombotic microangiopathy common to the different forms of the HUS/TTP syndrome. If HUS/TTP is left untreated, the mortality rate approaches 90%. Supportive therapy—including dialysis, antihypertensive medications, blood transfusions, and management of neurologic complications—contributes to the improved survival of patients with HUS/TTP. Adequate fluid balance and bowel rest are important in treating typical HUS associated with diarrhea.

radiation nephritis—The long-term consequences of renal irradiation in excess of 2500 rad can be divided into five clinical syndromes:

(i) Acute radiation nephritis occurs in approximately 40% of patients after a latency period of 6 to 13 months. It is characterized clinically by abrupt onset of hypertension, proteinuria, edema, and progressive renal failurein most cases leading to end-stage kidneys.

(ii) Chronic radiation nephritis, conversely, has a latency period that varies between 18 months and 14 years after the initial insult. It is insidious in onset and is characterized by hypertension, proteinuria, and gradual loss of renal function.

(iii) The third syndrome manifests 5 to 19 years after exposure to radiation as benign proteinuria with normal renal function (iv) A fourth group of patients exhibits only benign hypertension 2 to 5 years later and may have variable proteinuria. Late malignant hypertension arises 18 months to 11 years after irradiation in patients with either chronic radiation nephritis or benign hypertension. Removal of the affected kidney reversed the hypertension. Radiation-induced damage to the renal arteries with subsequent renovascular hypertension has been reported.

(v) A syndrome of renal insufficiency analogous to acute radiation nephritis has been observed in bone marrow transplantation (BMT) patients who were treated with total-body irradiation (TBI).

Irradiation causes endothelial dysfunction but spares vascular smooth muscle cells in the early postradiation phase. Radiation could directly damage DNA, leading to decreased regeneration of these cells and denudement of the basement membrane in the glomerular capillaries and tubules. In other kidney diseases, the microvasculature of the kidney is involved in autoimmune disorders, such as systemic sclerosis (scleroderma). Kidney involvement in systemic sclerosis manifests as a slowly progressing chronic renal disease or as scleroderma renal crisis (SRC), which is characterized by malignant hypertension and acute azotemia. It is postulated that SRC is caused by a Raynaud-like phenomenon in the kidney. Severe vasospasm leads to cortical ischemia and enhanced production of renin and angiotensin II, which in turn perpetuate renal vasoconstriction. Hormonal changes (pregnancy), physical and emotional stress, or cold temperature may trigger the Raynaud-like arterial vasospasm.

The renal microcirculation can also be affected in sickle cell disease, to which the kidney is particularly susceptible because of the low oxygen tension attained in the deep vessels of the renal medulla as a result of countercurrent transfer of oxygen along the vasa recta. The smaller renal arteries and arterioles can also be the site of thromboembolic injury from cholesterol-containing material dislodged from the walls of the large vessels.

Taken as a group, diseases that cause transient or permanent occlusion of renal microvasculature uniformly result in disruption of glomerular perfusion, and hence of the glomerular filtration rate, thereby constituting a serious threat to systemic homeostasis.

Acute Renal Failure (ARF)

ARF can be caused by microvascular or macrovascular disease (major renal artery occlusion or severe abdominal aortic disease). The classic microvascular diseases often present with microangiopathic hemolysis and acute renal failure occurring because of glomerular capillary thrombosis or occlusion, often with accompanying thrombocytopenia. Typical examples of these diseases include:

a) Thrombotic thrombocytopenic purpura—The classic pentad in thrombotic thrombocytopenic purpura includes fever, neurologic changes, renal failure, microangiopathic hemolytic anemia and thrombocytopenia.

b) Hemolytic uremic syndrome—Hemolytic uremic syndrome is similar to thrombotic thrombocytopenic purpura but does not present with neurologic changes.

c) HELLP syndrome (hemolysis, elevated liver enzymes and low platelets). HELLP syndrome is a type of hemolytic uremic syndrome that occurs in pregnant women with the addition of transaminase elevations.

Acute renal failure can present in all medical settings but is predominantly acquired in hospitals. The condition develops in 5 percent of hospitalized patients, and approximately 0.5 percent of hospitalized patients require dialysis. Over the past 40 years, the survival rate for acute renal failure has not improved, primarily because affected patients are now older and have more comorbid conditions. Infection accounts for 75 percent of deaths in patients with acute renal failure, and cardio-respiratory complications are the second most common cause of death. Depending on the severity of renal failure, the mortality rate can range from 7 percent to as high as 80 percent. Acute renal failure can be divided into three categories: Prerenal, intrinsic and postrenal ARF. Intrinsic ARF is subdivided into four categories: tubular disease, glomerular disease, vascular disease (includes microvascular) and interstitial disease.

Progressive Renal Disease

There is evidence that progressive renal disease is characterized by a progressive loss of the microvasculature. The loss of the microvasculature correlates directly with the development of glomerular and tubulointerstitial scarring. The mechanism is mediated in part by a reduction in the endothelial proliferative response, and this impairment in capillary repair is mediated by alteration in the local expression of both angiogenic (vascular endothelial growth factor) and antiangiogenic (thrombospondin 1) factors in the kidney. The alteration in balance of angiogenic growth factors is mediated by both macrophage-associated cytokines (interleukin-1β) and vasoactive mediators. Finally, there is intriguing evidence that stimulation of angiogenesis and/or capillary repair may stabilize renal function and slow progression and that this benefit occurs independently of effects on BP or proteinuria.

For further information see Brenner & Rector's The Kidney, 7th ed., Copyright© 2004 Elsevier: Chapter 33—*Microvascular diseases of the kidney* and also Tiwari and Vikrant Journal of Indian Academy of Clinical Medicine Vol. 5, No. 1 *Review Article—Sepsis and the Kidney*.

Renal Transplant

Delayed Graft Function

Delayed graft function (DGF) is the most common complication of the immediate postoperative period in renal transplantation and results in poor graft outcome (Moreso et al. 1999. Nephrol. Dial. Transplant. 14(4):930-35). Although the incidence and definition of DGF vary among transplant centers, the consequences are invariable: prolonged hospital stay, additional invasive procedures, and additional cost to the patient and health-care system.

Acute Transplant Rejection

Graft rejection has been categorized into three subsets depending on the onset of graft destruction: Hyperacute rejection is the term applied to very early graft destruction, usually within the first 48 hours. Acute rejection has an onset of several days to months or even years after transplantation and can involve humoral and/or cellular mechanisms. Chronic rejection relates to chronic alloreactive immune response.

Hearing Disorders

Chemical-Induced Ototoxicity

The toxic effects of various ototoxic therapeutic drugs on auditory cells and spiral ganglion neurons are often the limiting factor for their therapeutic usefulness. Main ototoxic drugs include the widely used chemotherapeutic agent cisplatin and its analogs, commonly used aminoglycoside antibiotics, e.g. gentamicin, for the treatment of infections caused by gram-negative bacteria, quinine and its analogs, salicylate and its analogs, and loop-diuretics.

For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980)). Clearly, ototoxicity is a dose-limiting side-effect of antibiotic administration. From 4 to 15% of patients receiving 1 gram per day for greater than 1 week develop measurable hearing loss, which slowly becomes worse and can lead to complete permanent deafness if treatment continues.

Ototoxicity is also a serious dose-limiting side-effect for cisplatin, a platinum coordination complex, that has proven effective on a variety of human cancers including testicular, ovarian, bladder, and head and neck cancer. Cisplatin (Platinol®) damages auditory and vestibular systems. Salicylates, such as aspirin, are the most commonly used therapeutic drugs for their anti-inflammatory, analgesic, anti-pyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

Accordingly, there exists a need for means to prevent, reduce or treat the incidence and/or severity of inner ear disorders and hearing impairments involving inner ear tissue, particularly inner ear hair cells. Of particular interest are those conditions arising as an unwanted side-effect of ototoxic therapeutic drugs including cisplatin and its analogs, aminoglycoside antibiotics, salicylate and its analogs, or loop diuretics. In addition, there exits a need for methods which will allow higher and thus more effective dosing with these ototoxicity-inducing pharmaceutical drugs, while concomitantly preventing or reducing ototoxic effects caused by these drugs. What is needed is a method that provides a safe, effective, and prolonged means for prophylactic or curative treatment of hearing impairments related to inner ear tissue damage, loss, or degeneration, particularly ototoxin-induced and particularly involving inner ear hair cells. In addition, there is required a method and composition for the treatment of damage and deafness resulting from inner ear trauma (acoustic trauma).

Without being bound by theory, it is believed that cisplatin drugs and other drugs that induce ototoxicity (such as aminoglycoside antibiotics), as well as acoustic trauma, may induce the ototoxic effects via programmed cell death or apoptosis in inner ear tissue, particularly inner ear hair cells (Zhang et al., Neuroscience 120 (2003) 191-205; Wang et al., J. Neuroscience 23((24):8596-8607). In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Presbycusis

Another type of hearing loss is presbycusis, which is hearing loss that gradually occurs in most individuals as they age. About 30-35 percent of adults between the ages of 65 and 75 years and 40-50 percent of people 75 and older experience hearing loss. Accordingly, there exists a need for means to prevent, reduce or treat the incidence and/or severity of inner ear disorders and hearing impairments involving inner ear tissue, particularly inner ear hair cells.

Acoustic Trauma

Acoustic trauma is a type of hearing loss that is caused by prolonged exposure to loud noises. Without wishing to be bound to theory, exposure to loud noise causes the hair cells on the cochlea to become less sensitive. With more severe exposure, injury can proceed from a loss of adjacent supporting cells to complete disruption of the organ of Corti. Death of the sensory cell can lead to progressive Wallerian degeneration and loss of primary auditory nerve fibers.

Of particular interest are those adverse conditions arising as a side-effect of therapeutic drugs including cisplatin and its analogs, aminoglycoside antibiotics, salicylate and its analogs, or loop diuretics. Thus, there exits a need for treatment methods which will allow higher and thus more effective dosing, while preventing or reducing ototoxic effects caused by these drugs. Thus, compositions and methods are needed that provide a safe, effective, and prolonged means for prophylactic or curative treatment of hearing impairments related to inner ear tissue damage, loss, or degeneration, particularly ototoxin-induced and particularly involving inner ear hair cells. In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Glaucoma

Glaucoma is one of the leading causes of blindness in the world. It affects approximately 66.8 million people worldwide. At least 12,000 Americans are blinded by this disease each year (Kahn and Milton, Am J. Epidemiol. 1980, 111(6): 769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage. Mucke (IDrugs 2007, 10(1):37-41) reviews current therapeutics, including siRNA to various targets for the treatment of ocular diseases, for example, age-related macular degeneration (AMD) and glaucoma.

Acute Respiratory Distress Syndrome

Acute respiratory distress syndrome (ARDS), also known as respiratory distress syndrome (RDS) or adult respiratory distress syndrome (in contrast with infant respiratory distress syndrome, IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators which cause inflammation, hypoxemia and frequently result in failure of multiple organs. This condition is life threatening and often lethal, usually requiring mechanical ventilation and admission to an intensive care unit. A less severe form is called acute lung injury (ALI).

Acute Lung Transplant Rejection

Acute allograft rejection remains a significant problem in lung transplantation despite advances in immunosuppressive medication. Rejection, and ultimately early morbidity and mortality may result from ischemia-reperfusion (I/R) injury and hypoxic injury.

Spinal Cord Injury

Spinal cord injury or myelopathy, is a disturbance of the spinal cord that results in loss of sensation and/or mobility. The two most common types of spinal cord injury are due to trauma and disease. Traumatic injuries are often due to automobile accidents, falls, gunshots diving accidents, and the like. Diseases which can affect the spinal cord include polio, spina bifida, tumors, and Friedreich's ataxia.

Oral Mucositis

Oral mucositis, also referred to as a stomatitis, is a common and debilitating side effect of chemotherapy and radiotherapy regimens, which manifests itself as erythema and painful ulcerative lesions of the mouth and throat. Routine activities such as eating, drinking, swallowing, and talking may be difficult or impossible for subjects with severe oral mucositis. Palliative therapy includes administration of analgesics and topical rinses.

Dry-Eye Syndrome

Dry eye syndrome is a common problem usually resulting from a decrease in the production of tear film that lubricates the eyes. Most patients with dry eye experience discomfort, and no vision loss; although in severe cases, the cornea may become damaged or infected. Wetting drops (artificial tears) may be used for treatment while lubricating ointments may help more severe cases.

More effective therapies to treat the above mentioned diseases and disorders would be of great therapeutic value.

Pressure Sores

Pressure sores or pressure ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's position.

Pressure sores are wounds which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Any of the above conditions can also be treated by compounds which comprise any of the siRNAs disclosed in co-assigned PCT publication No.s WO06/023544 and WO07/084,684.

Modifications

Modifications or analogs of nucleotides can be introduced to improve the therapeutic properties of the nucleotides. Improved properties include increased nuclease resistance and/or increased ability to permeate cell membranes.

Accordingly, the present invention also includes all analogs of, or modifications to, a oligonucleotide of the invention that does not substantially affect the function of the polynucleotide or oligonucleotide. In a preferred embodiment such modification is related to the base moiety of the nucleotide, to the sugar moiety of the nucleotide and/or to the phosphate moiety of the nucleotide.

In one embodiment the modification is a modification of the phosphate moiety, whereby the modified phosphate moiety is selected from the group comprising phosphothioate.

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., 1987, J. Am. Chem.

Soc., 109, 7845; Scaringe et al., 1990, NAR., 18, 5433; Wincott et al., 1995, NAR. 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. US 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from the nucleic acids set forth in Table A. For further information on tandem siRNA molecules and tandem structures which can be used in conjunction with siRNAs of the present invention, see PCT publication No. WO07/091,269, assigned to the assignee of the instant application, which is hereby incorporated by reference in uts entirety.

Thus, the siRNA molecules may be covalently or non-covalently bound or joined by a linker to form a tandem siRNA compound. Such tandem siRNA compounds comprising two siRNA sequences are typically of 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention. A tandem compound comprising two or more siRNAs sequences of the invention is envisaged.

siRNA molecules that target RTP801 may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which also targets RTP801 or another gene such as VEGF (see below). Simultaneous inhibition of said additional gene(s) will likely have an additive or synergistic effect for treatment of the diseases disclosed herein.

Additionally, the siRNA disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any RTP801 siRNA. In another example, an aptamer which can act like a ligand/antibody may be combined (covalently or non-covalently) with any RTP801 siRNA.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of the RTP801 gene. In particular, it is envisaged that this oligonucleotide comprises sense and antisense siRNA sequences as depicted in Table A, set forth in SEQ ID NOS:3-70.

All analogues of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. In some embodiments one or more nucleotides in an oligomer is substituted with inosine.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of siRNA compounds comprising LNA nucleotides are disclosed in Elmen et al., (NAR 2005, 33(1): 439-447).

The compounds of the present invention can be synthesized using one or more inverted nucleotides, for example inverted thymidine or inverted adenine (see, for example, Takei, et al., 2002, JBC 277(26):23800-06).

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and my further comprise at least one sugar, base and or backbone modification. U.S. Pat. No. 6,602,858 discloses nucleic acid catalysts comprising at least one L-nucleotide substitution.

Although the inhibitors of the present invention are preferably siRNA molecules, other inhibitors contemplated to be used in the methods of the invention to inhibit RTP801 and to treat the diseases and conditions described herein are inter alia antibodies, preferably neutralizing antibodies or fragments thereof, including single chain antibodies, antisense oligonucleotides, antisense DNA or RNA molecules, ribozymes, proteins, polypeptides and peptides including peptidomimetics and dominant negatives, and also expression vectors expressing all the above. Additional inhibitors may be small chemical molecules, which generally have a molecular weight of less than 2000 daltons, more preferably less than 1000 daltons, even more preferably less than 500 daltons. These inhibitors may act as follows: small molecules may affect expression and/or activity; antibodies may affect activity; all kinds of antisense may affect RT801 gene expression; and dominant negative polypeptides and peptidomimetics may affect activity; expression vectors may be used inter alia for delivery of antisense or dominant-negative polypeptides or antibodies.

Antibodies

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;

(2) (Fab')$_2$. the fragment of the antibody that can be obtained by treating whole antibody with the enzyme pepsin without subsequent reduction; F(ab'$_2$) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

Antisense Molecules

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (Aboul-Fadl, Curr Med. Chem. 2005. 12(19):2193-214; Crooke, Curr Mol. Med. 2004. 4(5):465-87; Crooke, Annu Rev Med. 2004; 55:61-95; Vacek et al., Cell Mol Life Sci. 2003. 60(5):825-33; Cho-Chung, Arch Pharm Res. 2003. 26(3):183-91. There are further reviews on the chemical (Crooke, 1995; Uhlmann et al, 1990), cellular (Wagner, 1994. Nature. 24; 372(6504):333-5) and therapeutic (Hanania, et al, 1995; Scanlon, et al, 1995; Gewirtz, 1993) aspects of this technology. Antisense intervention in the expression of specific genes can be achieved by the use of synthetic AS oligonucleotide sequences (see for example, Zhang et al., Curr Cancer Drug Targets. 2005 5(1): 43-9.)

AS oligonucleotide sequences may be short sequences of DNA, typically 15-30 mer but may be as small as 7 mer (Wagner et al, 1996 Nat. Biotechnol. 14(7):840-4), designed to complement a target mRNA of interest and form an RNA: AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996 BBRC. 229(1):305-9). For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for a variety of different genes including integrin (Galileo et al., Neuron. 1992 9(6): 1117-31.) and for the N-myc protein (Rosolen et al., 1990 Prog Clin Biol Res. 366:29-36). Antisense oligonucleotide inhibition of basic fibroblast growth factor (bFGF), having mitogenic and angiogenic properties, suppressed 80% of growth in glioma cells (Morrison, JBC 1991 266(2):728-34) in a saturable and specific manner. Being hydrophobic, antisense oligonucleotides interact well with phospholipid membranes (Akhter et al., NAR. 1991, 19:5551-5559). Following their interaction with the cellular plasma membrane, they are actively (or passively) transported into living cells (Loke et al., PNAS 1989, 86(10):3474-8), in a saturable mechanism predicted to involve specific receptors (Yakubov et al., PNAS, 1989 86(17):6454-58).

Ribozymes

A "ribozyme" is an RNA molecule that possesses RNA catalytic ability (see Cech Biochem Soc Trans. 2002 November; 30(Pt 6):1162-6, for review) and cleaves a specific site in a target RNA. In accordance with the present invention, ribozymes which cleave mRNA may be utilized as inhibitors. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stochiochemistry (Hampel and Tritz, Biochem. 1989, 28(12): 4929-33; Uhlenbeck, Nature. 1987 328(6131):596-600).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

Screening of Inactivation Compounds for RTP801

Some of the compounds and compositions of the present invention may be used in a screening assay for identifying and isolating compounds that modulate the activity of RTP801, in particular compounds that modulate a disorder accompanied by an elevated level of RTP801. The compounds to be screened comprise inter alia substances such as small chemical molecules and antisense oligonucleotides.

The inhibitory activity of the compounds of the present invention on RTP801 or binding of the compounds of the present invention to RTP801 may be used to determine the interaction of an additional compound with the RTP801 polypeptide, e.g., if the additional compound competes with the oligonucleotides of the present invention for inhibition of RTP801, or if the additional compound rescues said inhibition. The inhibition or activation can be tested by various means, such as, inter alia, assaying for the product of the activity of the RTP801 polypeptide or displacement of binding compound from the RTP801 polypeptide in radioactive or fluorescent competition assays.

For further information on screening systems utilizing RTP801 and screening systems in which the siRNAs of the present invention can be used, see PCT application No.s PCT/US2007/011266 and PCT/IL 2007/000774, assigned to the assignee of the instant application, which are hereby incorporated by reference in their entirety.

In one embodiment the present invention provides for a method of treating a patient suffering from a condition selected from a microvascular disorder, an eye disease, a respiratory disorder, a hearing disorder, pressure sores or a spinal cord injury or other wound, comprising administering to the patient a pharmaceutical composition comprising an RTP801 inhibitor in a therapeutically effective amount so as to thereby treat the patient. The invention further provides a method of treating a patient suffering from a microvascular disorder, an eye disease a respiratory disorder, a hearing disorder, pressure sores or a spinal cord injury or other wound, comprising administering to the patient a pharmaceutical composition comprising an RTP801 inhibitor, in a dosage and over a period of time sufficient to promote recovery. The eye disease may be macular degeneration such as age-related macular degeneration (AMD), inter alia. The microvascular disorder may be diabetic retinopathy or acute renal failure, inter alia. The respiratory disorder may be chronic obstructive pulmonary disease (COPD), emphysema, chronic bronchitis, asthma and lung cancer, inter alia. The hearing disorder may be acoustic trauma or cisplatin-induced deafness, inter alia. The RTP801 inhibitor may be selected from a large variety of molecules, including but not limited to compounds such as polynucleotides, antisense fragments, RNA molecules which target the RTP801 gene mRNA such as ribozymes or siRNAs (such as the siRNAs of Table A and in particular, siRNA listed as Nos: 102, 103 and 106 of Table A), or expression vectors comprising them; polypeptides such as dominant negatives, antibodies (such as an antibody which specifically binds to an epitope present within a polypeptide which comprises consecutive amino acids, the sequence of which is set forth in FIG. 2 (SEQ ID No:2)), or, in some cases, enzymes. Additionally, the RTP801 inhibitor may be a chemical inhibitor such as a small molecule, e.g., chemical molecules with a low molecular weight e.g. a molecular weight below 2000 daltons. Specific RTP801 inhibitors are given below.

The present invention further provides a method for treating a patient suffering from macular degeneration, COPD, diabetic retinopathy or acoustic trauma-induced deafness, comprising administering to the patient a pharmaceutical composition comprising a therapeutically effective dose of an RTP801 inhibitor comprising a polynucleotide which specifically hybridizes to mRNA transcribed from the RTP801 gene and down regulates the expression of the RTP801 gene so as to thereby treat the patient. The polynucleotide may be an siRNA comprising consecutive nucleotides having a sequence identical to any sequence set forth in Table A (SEQ ID NOs:3-70) and in particular, siRNA listed as Nos: 102, 103 and 106.

Further, an additional embodiment of the present invention concerns a method for treating a patient suffering from a microvascular disorder, an eye disease, a respiratory disorder, a hearing disorder, pressure sores or a spinal cord injury or other wound, comprising administering to the patient a pharmaceutical composition comprising a therapeutically effective dose of an RTP801 inhibitor comprising an siRNA molecule, optionally an siRNA molecule detailed in Table A, in a dosage and over a period of time so as to thereby treat the patient.

An additional method for treating a patient suffering from a microvascular disorder, an eye disease, a respiratory disorder, a hearing disorder, pressure sores or a spinal cord injury or other wound is provided, comprising administering to the patient a pharmaceutical composition comprising a therapeutically effective dose of an RNA molecule which targets the RTP801 gene mRNA in a dosage and over a period of time so as to thereby treat the patient. The RNA molecule may be an siRNA molecule, such as an siRNA molecule detailed in Table A and in particular, siRNA Nos: 102, 103 and 106, or a ribozyme.

The present invention further provides a method for treating a patient suffering from a microvascular disorder, an eye disease, a respiratory disorder, a hearing disorder, pressure sores or a spinal cord injury or other wound or any of the conditions disclosed herein, comprising administering to the patient a pharmaceutical composition comprising a therapeutically effective dose of an siRNA molecule which targets the RTP801 gene mRNA, optionally an siRNA molecule detailed in Table A, in a dosage and over a period of time so as to thereby treat the patient. Further, the eye disease may be macular degeneration such as age-related macular degeneration (AMD); the microvascular disorder may be diabetic retinopathy or acute renal failure; the respiratory disorder may be COPD and the aspects of COPD being treated may comprise, but are not limited to, emphysema, chronic bronchitis, or both; and the hearing disorder may be acoustic trauma-induced deafness.

The present invention additionally relates to the use of the novel siRNAs disclosed herein in the treatment of hearing impairment in which inhibition of RTP801 expression is beneficial. In one embodiment, the present invention constitutes a method for treating a mammal having or prone to a hearing (or balance) impairment or treating a mammal prophylactically in conditions where inhibition of RTP801 expression is beneficial. The method of this embodiment of the present invention would prevent or reduce the occurrence or severity of a hearing (or balance) impairment that would result from inner ear cell injury, loss, or degeneration, in particular caused by acoustic trauma or an ototoxic agent. In this embodiment, the method of the invention includes administering a therapeutically effective amount of one or more compounds which down-regulate expression of the RTP801 gene, particularly the novel siRNAs of the present invention.

siRNA compounds directed against RTP801 have been used successfully by the assignee of the present invention in the treatment of COPD, AMD, ARF, microvascular disorders and deafness, in primates and other mammals. For further information and animal models aimed at researching and treating these conditions, see PCT publication No. WO06/023544A2 and PCT patent publication No. WO07/084,684, which are hereby incorporated by reference in their entirety.

In another embodiment, the methods of the invention are applied to treating or preventing the incidence or severity of pressure sores. The methods and compositions involve administering to a mammal in need of such treatment a prophylactically or therapeutically effective amount of one or more compounds which down-regulate expression of the RTP801 gene, particularly novel small interfering RNAs (siRNAs). The compounds which treat or prevent the incidence or severity of pressure sores, particularly the novel siRNAs are preferably administered locally within the damaged area. The methods and compositions of the present invention are effective in the treatment and prevention of pressure sores or pressure ulcers developed when sustained pressure (usually from a bed or wheelchair) cuts off circulation to vulnerable parts of the body. The methods and compositions are effective in patients with diminished or absent sensation or who are debilitated, emaciated, paralyzed, or long bedridden. The compositions of the present invention are effective also in improving the healing of pressure sores using the compositions. The compositions may be used at any particular stage in the healing process including the stage before any healing has initiated or even before a specific sore is formed (prophylactic treatment).

Other kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions.

The methods and compositions of the present invention are also effective in the treatment and prevention of any chronic wounds including inter alia pressure sores, venous ulcers, and diabetic ulcers. In all these chronic wound types, the underlying precipitating event is a period of ischemia followed by a period of reperfusion. These ischemia-reperfusion events are usually repetitive, which means the deleterious effects of ischemia-reperfusion are potentiated and eventually sufficient to cause ulceration. For both pressure sores and diabetic foot ulcers, the ischemic event is the result of prolonged pressure sufficient to prevent tissue perfusion, and when the pressure is finally relieved, the reperfusion injury occurs. The present compositions are effective in inhibiting the damage caused by ischemia-reperfusion in chronic wounds.

The present compositions are also effective in other conditions associated with ischemia-reperfusion such as but not limited to: organ transplantation, intestinal and colon anastamoses, operations on large blood vessels, stitching detached limbs, balloon angioplasty or any cardiac surgery, stroke or brain trauma, limb transplantation, pulmonary hypertension, hypoxemia, and noncardiogenic pulmonary edema, acute renal failure, acute glaucoma, diabetic retinopathy, hypertensive retinopathy, retinal vascular occlusion, cochlear ischemia, microvascular surgery and ischemic lesions in scleroderma.

The methods and compositions of the present invention are also effective in the treatment of acoustic trauma or mechanical trauma, preferably acoustic or mechanical trauma that leads to inner ear hair cell loss. Acoustic trauma to be treated in the present invention may be caused by a single exposure to an extremely loud sound, or following long-term exposure to everyday loud sounds above about 85 decibels. Mechanical inner ear trauma to be treated in the present invention is for example the inner ear trauma following an operation of electronic device insertion in the inner ear. The compositions of the present invention prevent or minimize the damage to inner ear hair cells associated with the operation. The compounds which reduce or prevent the ototoxin-induced hearing impairment, particularly the novel siRNAs are preferably administered locally within the inner ear, optionally by trans-tympanic injection.

Additionally, the compound of the present invention can be used to treat any condition in which ischemia is involved, optionally ischemia-reperfusion. Such condition include ischemia or ischemia-reperfusion resulting from an angioplasty, cardiac surgery or thrombolysis; organ transplant; as a result of plastic surgery; during severe compartment syndrome; during re-attachment of severed limbs; as a result of multiorgan failure syndrome; in the brain as a result of stroke or brain trauma; in connection with chronic wounds such as pressure sores, venous ulcers and diabetic ulcers; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal failure as observed after renal transplantation, major surgery, trauma, and septic as well as hemorrhagic shock; sepsis; retinal ischemia occurring as a result of acute vascular occlusion, leading to loss of vision in a number of ocular diseases such as acute glaucoma, diabetic retinopathy, hypertensive retinopathy, and retinal vascular occlusion; cochlear ischemia; flap failure in microvascular surgery for head and neck defects; Raynaud's phenomenon and the associated digital ischemic lesions in scleroderma; spinal cord injury; vascular surgery; traumatic rhabdomyolysis (crush syndrome); and myoglobinuria. Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor; and diseases such as stroke, Parkinson's disease, epilepsy, depression, ALS, Alzheimer's disease, Huntington's disease and any other disease-induced dementia (such as HIV induced dementia for example). Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracarnial hematoma or edema). Similarly, traumatic constriction or compression can arise from the presence of a mass of abnormal tissue, such as a metastatic or primary tumor.

The methods of treating the diseases disclosed herein and included in the present invention may include administering an RTP801 inhibitor in conjunction with an additional RTP801 inhibitor, a substance which improves the pharmacological properties of the active ingredient as detailed below, or an additional compound known to be effective in the treatment of the disease to be treated, such as macular degeneration, COPD, ARF, DR, cisplatin or acoustic trauma-induced deafness, inter alia. By "in conjunction with" is meant prior to, simultaneously or subsequent to. Further detail on exemplary conjoined therapies is given below.

In another embodiment, the present invention provides for the use of a therapeutically effective dose of an RTP801 inhibitor for the preparation of a medicament for promoting recovery in a patient suffering from macular degeneration, COPD, ARF, DR, cisplatin or acoustic trauma-induced deafness or any other eye disease, microvascular or respiratory condition or hearing disorder as detailed above, and the use of a therapeutically effective dose of an RTP801 inhibitor for the preparation of a medicament for treating said diseases and conditions. In this embodiment, the RTP801 inhibitor may comprise a polynucleotide which comprises consecutive nucleotides having a sequence which comprises an antisense sequence to the sequence set forth in FIG. 1 (SEQ ID No: 1). Additionally, the RTP801 inhibitor may be an expression vector comprising a polynucleotide having a sequence which is an antisense sequence to the sequence set forth in FIG. 1 (SEQ ID No:1). The RTP801 inhibitor according to said uses may also be an antibody, such as a neutralizing antibody which specifically binds to an epitope present within a polypeptide which comprises consecutive amino acids, the sequence of which is set forth in FIG. 2 (SEQ ID No:2). Additionally, the RTP801 inhibitor may be an RNA molecule which targets the RTP801 gene mRNA optionally an siRNA, optionally an siRNA comprising consecutive nucleotides having a sequence identical to any sequence set forth in Table A (SEQ ID NOs:3-70) and in particular, siRNA Nos: 102, 103 and 106, or a ribozyme.

Thus, according to the information disclosed herein, the RTP801 inhibitor to be used with any of the methods disclosed herein, in any of the uses disclosed herein and in any of the pharmaceutical compositions disclosed herein, may be selected from the group consisting of an siRNA, a vector comprising an siRNA, a vector which expresses an siRNA and any molecule which is endogenously processed into an siRNA. As detailed herein, said siRNA is preferably an siRNA comprising consecutive nucleotides having a sequence identical to any sequence set forth in Table A (SEQ ID NOs:3-70) and in particular, siRNA Nos: 102, 103 and 106.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, anterior ischemic optic neuropathy, optic neuritis (primary or secondary to autoimmune diseases), glaucoma, von hippel lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, birdshot retinochoroidopathy, long-standing retinal detachment; systemic conditions such as diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, neuropathies, nephropathies, microvascular diseases of the kidney, and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. All these neovascular conditions may be treated using the compounds and pharmaceutical compositions of the present invention.

"Eye disease" refers to refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases and retinal vein occlusion (RVO). Some conditions disclosed herein, such as DR, which may be treated according to the methods of the present invention have been regarded as either a microvascular disorder and an eye disease, or both, under the definitions presented herein.

Hearing impairments relevant to the invention may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than about 85 decibels (db) that damages the inner ear. Preferably, the hearing loss is caused by acoustic trauma or an ototoxic drug that effects the auditory portion of the inner ear, particularly inner ear hair cells. Incorporated herein by reference are Chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Hearing disorders or impairments (or balance impairment) to be treated or prevented in the context of the present invention are preferably, without being bound by theory, ototoxin- or trauma-induced apoptotic damage to inner ear hair cells. Those in need of treatment include those already experiencing a hearing impairment, those prone to having the impairment, and those in which the impairment is to be prevented. Without being bound by theory, the hearing impairments may be due to apoptotic inner ear hair cell damage or loss, wherein the damage or loss is caused by infection, mechanical injury, loud sound, aging, or chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity or acoustic trauma, especially resulting from or expected to result from administration of therapeutic drugs or exposure to acoustic-trauma including environments. Preferably a therapeutically effective composition is given immediately after the exposure to prevent or reduce the ototoxic effect or traumatic effect. More preferably, treatment is provided prophylactically, either by administration of the composition prior to or concomitantly with the ototoxic pharmaceutical or the exposure to the ototoxin or to the acoustic-trauma inducing environment. The hearing impairment may be induced by chemotherapy.

"RTP801 gene" refers to the RTP801 coding sequence open reading frame, as shown in FIG. 1 (SEQ ID NO:1), or any homologous sequence thereof preferably having at least 70% identity, more preferable 80% identity, even more preferably 90% or 95% identity. This encompasses any sequences derived from SEQ ID NO:1 which have undergone mutations, alterations or modifications as described herein. Thus, in a preferred embodiment RTP801 is encoded by a nucleic acid sequence according to SEQ. ID. NO. 1. It is also within the present invention that the nucleic acids according to the present invention are only complementary and identical, respectively, to a part of the nucleic acid coding for RTP801 as, preferably, the first stretch and first strand is typically shorter than the nucleic acid according to the present invention. It is also to be acknowledged that based on the amino acid sequence of RTP801 any nucleic acid sequence coding for such amino acid sequence can be perceived by the one skilled in the art based on the genetic code. However, due to the assumed mode of action of the nucleic acids according to the present invention, it is most preferred that the nucleic acid coding for RTP801, preferably the mRNA thereof, is the one present in the organism, tissue and/or cell, respectively, where the expression of RTP801 is to be reduced.

"RTP801 polypeptide" refers to the polypeptide of the RTP801 gene, and is understood to include, for the purposes of the instant invention, the terms "RTP779", "REDD1", "Ddit4", "FLJ20500", "Dig2", and "PRF1", derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the RTP801 coding sequence, such as, inter alia, point mutations, substitutions, deletions and insertions which may cause a difference in a few amino acids between the resultant polypeptide and the naturally occurring RTP801. Polypeptides encoded by nucleic acid sequences which bind to the RTP801 coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified RTP801 or chemically modified fragments of RTP801 are also included in the term, so long as the biological activity is retained. RTP801 preferably has or comprises an amino acid sequence according to SEQ. ID. NO. 2. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of RTP801 include amino acids 1-50, 51-100, 101-150, 151-200 and 201-232 of the sequence shown in FIG. 2. Further particular fragments of RTP801 include amino acids at positions 25-74, 75-124, 125-174, 175-224 and 225-232 of the sequence shown in FIG. 2.

RTP801 as used herein is a protein described, among others, in WO 99/09046. RTP801 which is also referred to as RTP801, has been described as a transcriptional target of HIF-1α by Shoshani T et al. (Shoshani et al., 2002, Mol Cell Biol, 22, 2283-93). Furthermore the study by Ellisen et al. (Ellisen et al., Mol Cell, 10, 995-1005) has identified RTP801 as a p53-dependent DNA damage response gene and as a p63-dependent gene involved in epithelial differentiation. Also, RTP801 mirrors the tissue-specific pattern of the p53 family member p63, is effective similar to or in addition to TP 63, is an inhibitor to in vitro differentiation, and is involved in the regulation of reactive oxygen species. Apart from that, RTP801 is responsive to hypoxia-responsive transcription factor hypoxia-inducible factor 1 (HIF-1) and is typically up-regulated during hypoxia both in vitro and in vivo in an animal model of ischemic stroke. RTP801 appears to function in the regulation of reactive oxygen species (ROS) and ROS levels and reduced sensitivity to oxidative stress are both increased following ectopic expression RTP801 (Ellisen et al. 2002, supra; Soshani et al. 2002, supra). Preferably, RTP801 is a biologically active RTP801 protein which preferably exhibits at least one of those characteristics, preferable two or more and most preferably each and any of these characteristics.

Without being bound by theory, RTP801 being a stress-inducible protein (responding to hypoxia, oxidative stress, thermal stress, ER stress) is a factor acting in fine-tuning of cell response to energy disbalance. As such, it is a target suitable for treatment of any disease in which cells should be rescued from apoptosis due to stressful conditions (e.g. diseases accompanied by death of normal cells) or where cells, which are adapted to stressful conditions due to changes in RTP801 expression (e.g. cancer cells), should be killed. In the latter case, RTP801 may be viewed as a survival factor for cancer cells and its inhibitors may treat cancer as a monotherapy or as sensitising drugs in combination with chemotherapy or radiotherapy.

The term "amino acid" refers to a molecule which consists of any one of the 20 naturally occurring amino acids, amino acids which have been chemically modified (see below), or synthetic amino acids.

The term "polypeptide" refers to a molecule composed of two or more amino acids residues. The term includes peptides, polypeptides, proteins and peptidomimetics.

A "peptidomimetic" is a compound containing non-peptidic structural elements that is capable of mimicking the biological action(s) of a natural parent peptide. Some of the classical peptide characteristics such as enzymatically scissile peptidic bonds are normally not present in a peptidomimetic.

By the term "dominant negative peptide" is meant a polypeptide encoded by a cDNA fragment that encodes for a part of a protein (see Herskowitz, Nature. 1987 Sep. 17-23; 329(6136):219-22. Review; Roninson et al., Cornelius P. Rhoads Memorial Award Lecture. Cancer Res. 1995 Sep. 15; 55(18):4023). This peptide can have a different function from the protein from which it was derived. It can interact with the full protein and inhibit its activity or it can interact with other proteins and inhibit their activity in response to the full-length (parent) protein. Dominant negative means that the peptide is able to overcome the natural parent protein and inhibit its activity to give the cell a different characteristic, such as resistance or sensitization to death or any cellular phenotype of interest. For therapeutic intervention the peptide itself may be delivered as the active ingredient of a pharmaceutical composition, or the cDNA can be delivered to the cell utilizing known methods.

Preparation of Peptides and Polypeptides

Polypeptides may be produced via several methods, for example:

1) Synthetically:

Synthetic polypeptides can be made using a commercially available machine, using the known sequence of RTP801 or a portion thereof.

2) Recombinant Methods:

A preferred method of making the RTP801 polypeptides of fragments thereof is to clone a polynucleotide comprising the cDNA of the RTP801 gene into an expression vector and culture the cell harboring the vector so as to express the encoded polypeptide, and then purify the resulting polypeptide, all performed using methods known in the art as described in, for example, Marshak et al., "Strategies for Protein Purification and Characterization. A laboratory course manual." CSHL Press (1996). (in addition, see Bibl Haematol. 1965; 23:1165-74 Appl Microbiol. 1967 July; 15(4):851-6; Can J. Biochem. 1968 May; 46(5):441-4; Biochemistry. 1968 July; 7(7):2574-80; Arch Biochem Biophys. 1968 Sep. 10; 126(3):746-72; Biochem Biophys Res Commun. 1970 Feb. 20; 38(4):825-30).).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al. (1986).

3) Purification from Natural Sources:

RTP801 polypeptide, or naturally occurring fragments thereof, can be purified from natural sources (such as tissues) using many methods known to one of ordinary skill in the art, such as for example: immuno-precipitation with anti-RTP801 antibody, or matrix-bound affinity chromatography with any molecule known to bind RTP801.

Protein purification is practiced as is known in the art as described in, for example, Marshak et al., "*Strategies for Protein Purification and Characterization. A laboratory course manual*." CSHL Press (1996).

By "biological effect of RTP801" or "RTP801 biological activity" is meant the effect of RTP801 in disorders, which may be direct or indirect. Regarding respiratory disorders this includes, without being bound by theory, the effect of RTP801 on apoptosis of alveolar cells induced by hypoxic or hyperoxic conditions. The indirect effect includes, but is not limited to, RTP801 binding to or having an effect on one of several molecules, which are involved in a signal transduction cascade resulting in apoptosis.

"Apoptosis" refers to a physiological type of cell death which results from activation of some cellular mechanisms, i.e. death that is controlled by the machinery of the cell. Apoptosis may, for example, be the result of activation of the cell machinery by an external trigger, e.g. a cytokine or anti-FAS antibody, which leads to cell death or by an internal signal. The term "programmed cell death" may also be used interchangeably with "apoptosis".

"Apoptosis-related disease" refers to a disease whose etiology is related either wholly or partially to the process of apoptosis. The disease may be caused either by a malfunction of the apoptotic process (such as in cancer or an autoimmune disease) or by overactivity of the apoptotic process (such as in certain neurodegenerative diseases). Many diseases in which RTP801 is involved are apoptosis-related diseases. For example, apoptosis is a significant mechanism in dry AMD, whereby slow atrophy of photoreceptor and pigment epithelium cells, primarily in the central (macular) region of retina takes place. Neuroretinal apoptosis is also a significant mechanism in diabetic retinopathy.

"Expression vector" refers to a vector that has the ability to incorporate and express heterologous DNA fragments in a foreign cell. Many prokaryotic and eukaryotic expression vectors are known and/or commercially available. Selection of appropriate expression vectors is within the knowledge of those having skill in the art.

Preparation of Anti-RTP801 Antibodies

Antibodies which bind to RTP801 or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of the RTP801. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, *Current Protocols in Immunology*, Wiley Interscience, 1994).

Methods for making antibodies of all types, including fragments, are known in the art (See for example, Harlow and Lane, *Antibodies: A Laboratory Manual*, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR—grafting (EP239,400: PCT publication WO.91/09967; U.S. Pat. Nos. 5,225,539; 5,530,101; and 5,585,089, veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

Antibodies to RTP801 are detailed in U.S. Pat. No. 6,740,738, which is hereby incorporated by reference in its entirety.

The terms "chemical compound", "small molecule", "chemical molecule" "small chemical molecule" and "small chemical compound" are used interchangeably herein and are understood to refer to chemical moieties of any particular type which may be synthetically produced or obtained from natural sources and usually have a molecular weight of less than 2000 daltons, less than 1000 daltons or even less than 600 daltons.

The present invention also relates to functional nucleic acids comprising a double-stranded structure, their use for the manufacture of a medicament, a pharmaceutical composition comprising such functional nucleic acids and a method for the treatment of a patient.

Hypoxia has been recognised as a key element in the pathomechanism of quite a number of diseases such as stroke, emphysema and infarct which are associated with sub-optimum oxygen availability and tissue damaging responses to the hypoxia conditions. In fast-growing tissues, including tumor, a sub-optimum oxygen availability is compensated by undesired neo-angiogenesis. Therefore, at least in case of cancer diseases, the growth of vasculature is undesired.

In view of this, the inhibition of angiogenesis and vascular growth, respectively, is subject to intense research. Already today some compounds are available which inhibit undesired angiogenesis and vascular growth. Some of the more prominent compounds are those inhibiting VEGF and the VEGF receptor. In both cases, the effect of VEGF is avoided by either blocking VEGF as such, for example by using an antibody directed against VEGF such as pursued by Genentech's AVASTIN® (monoclonal AB specific for VEGF) (Ferrara N.; Endocr Rev. 2004 August; 25(4):581-611), or by blocking the corresponding receptor, i.e. the VEGF receptor (Traxler P; Cancer Res. 2004 Jul. 15; 64(14):4931-41; or Stadler W M et al., Clin Cancer Res. 2004 May 15; 10(10):3365-70).

As, however, angiogenesis and the growth of vasculature is a very basic and vital process in any animal and human being, the effect of this kind of compound has to be focused at the particular site where angiogenesis and vascular growth is actually undesired which renders appropriate targeting or delivery a critical issue in connection with this kind of therapeutic approach.

It is thus an objective of the present invention to provide further means for the treatment of diseases involving undesired growth of vasculature and angiogenesis, respectively.

An additional aspect of the present invention provides for a pharmaceutical composition comprising a compound of the above structure (A) for the treatment of any of the diseases and conditions mentioned herein.

Further, this aspect provides for a pharmaceutical composition comprising two or more compounds of the above structure (A) for the treatment of any of the diseases and conditions mentioned herein, whereby said two compounds may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. Such siRNA molecules are therefore comprised of a double-stranded nucleic acid structure as described herein, whereby two siRNA sequences selected from Table A and preferably from ID Nos: 102, 103 and 106 are covalently or non-covalently bound or joined by a linker to form a tandem siRNA molecule. Further, said siRNAs of Table A may also be covalently or non-covalently bound to any antisense strand of any siRNA disclosed in WO 06/023544A2 or PCT/US2007/01468, which are both co-assigned to the assignee of the present invention and incorporated by reference in their entirety. Such tandem siRNA molecules comprising two siRNA sequences would typically be of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention, and further information concerning them is given below.

Said combined or tandem structures have the advantage that toxicity and/or off-target effects of each siRNA are minimized, while the efficacy is increased.

Of the nucleic acids according to the present invention as disclosed herein, those with internal reference numbers 102, 103 and 106 (see Table A) are particularly preferred. In connection therewith it is to be noted that those nucleic acids according to the present invention which can be used in both human and an animal model such as rat and/or mouse are particularly useful. The surprising advantage of these particular nucleic acids according to the present invention resides in the fact that they are effective both in human and in an animal model which means that the test results obtained in the animal model can be immediately transferred from the animal model to the human being and more particularly without the necessity to make any changes to the human sequence which would otherwise become necessary in case the nucleic acid according to the present invention was designed such as to comprise (a) sequence(s) which differ(s) between the species, more particularly the species used for animal model testing and man as the ultimate preferred organisms or patient. It is further preferred that these nucleic acids have a modification pattern as also described in the examples.

However, it is also within the present invention that any of the sequences according to SEQ. ID. NOs. 3-70 is only partially contained in a further nucleic acid according to the present invention. Preferably, the further nucleic acids according to the present invention comprise at least 14 contiguous nucleotides of the SEQ. ID. NO.s 3-70 and more preferably 14 contiguous nucleotide base pairs at any end of the double-stranded structure comprised of the first stretch and second stretch as outlined in the preceding table. It will be understood by the ones skilled in the art that given the potential length of the nucleic acid according to the present invention and particularly of the individual stretches forming such nucleic acid according to the present invention, some shifts relative to the coding sequence of RTP801 to each side is possible, whereby such shifts can be up to 1, 2, 3, 4, 5 and 6 nucleotides in both directions, and whereby the thus generated double-stranded nucleic acid molecules shall also be within the present invention.

siRNA for RTP801 can be made using methods known in the art as described above, based on the known sequence of RTP801 (SEQ ID NO:1), and can be made stable by various modifications as described above. For further information, see Example 3.

Further, in relation to the methods of the present invention as described herein, additional RNA molecules may be used with said methods e.g. inhibitory RNA molecules of the present invention include single stranded oligoribonucleotides preferably comprising stretches of at least 7-10 consecutive nucleotides present in the sequences detailed in Table A, said oligoribonucleotides being capable of forming [and/or comprising] double stranded regions in particular conformations that are recognized by intracellular complexes, leading to the degradation of said oligoribonucleotides into smaller RNA molecules that are capable of exerting inhibition of their corresponding endogenous gene, and DNA molecules encoding such RNA molecules. The corresponding endogenous gene is preferably the 801 gene and may additionally be the VEGF gene and/or the VEGF-R1 gene. The invention also provides a composition comprising the above single stranded oligoribonucleotide in a carrier, preferably a pharmaceutically acceptable carrier.

Additionally, the present invention provides for combination therapy for all the conditions disclosed herein and in particular conditions involving choroidal neovascularization. In said combination therapy, both the RTP801 and VEGFR genes are inhibited in order to ameliorate the symptoms of the disease being treated. These genes may be inhibited with a combination of one or more siRNAs or antibodies or aptamers. The present invention therefore also provides for a novel pharmaceutical composition comprising an RTP801 inhibitor and a VEGF or VEGFR-1 inhibitor, the RTP801 inhibitor preferable being an siRNA, more preferably an siRNA molecule detailed in Table A and in particular, siRNA Nos: 102, 103 and 106, and the VEGF/VEGFR-1 inhibitor optionally being an antibody or aptamer. The combined use of said compounds (i.e., RTP801 siRNA and VEGF antibody or any other combined example disclosed herein) in the preparation of a medicament is also part of the present invention.

Thus, RTP801 siRNA such as an siRNA molecule detailed in Table A and in particular, siRNA Nos: s 102, 103 and 106 may be administered in conjunction with agents which target VEGF or VEGF receptor 1 (VEGFR1). Such agents currently exist on the market or in various stages of approval and work through different mechanisms. Antibodies and antibody fragments such as ranibizumab (Lucentis, Genentech) attach to released VEGF to inhibit binding of VEGF to active receptors. An aptamer which can act like a ligand/antibody (Macugen, Eyetech/Pfizer, approved recently by the FDA for wet AMD) is also a possibility. Macugen bonds with extracellular VEGF to block its activity. These drugs are administered locally by intravitreal injection. Anti-VEGF siRNA based compounds (such as Acuity's Cand5 inhibitor of VEGF or SIRNA's 027 inhibitor of VEGFR-1) are also available. Additionally, the small molecule aminosterol Squalamine (Genaera) which is administered systemically reportedly interferes in multiple facets of the angiogenic process, including inhibiting VEGF and other growth factor signaling in endothelial cells.

The conjoined administration of an RTP801 inhibitor, preferably an siRNA, and any of the above VEGF/VEGFR-1 inhibitory agents can have a synergistic effect whereby said combined treatment is more effective than treatment by any of these individual compositions, irrespective of dosage in the single therapy option.

RTP801i has a different mechanism of action and is potentially synergistic with VEGF-VEGFR inhibitors. A study in RTP801 KO mice indicates that protective phenotype in the KO mice persists in spite of the fact that expression of VEGF mRNA in the eye is as high as in the WT mice. Our additional preliminary data indicate that inhibition of RTP801 may be synergistic with the inhibition of VEGF-VEGFR regulatory axis in treatment of retinal pathology. The inventors of the present invention have found in appropriate experiments that administration of siRNA against RTP801 in the model of AMD (see Example 2 below) leads not only to downregulation of RTP801 itself but also, as a consequence, to upregulation of the antiangiogenic and neuroprotective factor PEDF as well as the downregulation of expression of MCP1, a macrophage chemoattractant protein. Thus, inhibition of RTP801 simultaneously confers antiangiogenic, neuroprotective and anti-inflammatory effects.

As disclosed herein, aptamers may also be used in the present invention in combination with the novel siRNAs disclosed herein. For example, an aptamer can be used with any one of the siRNAs disclosed herein in combination therapy for the treatment of any one of the conditions disclosed herein. The novel pharmaceutical composition employed for such a combination therapy, which is also part of the present invention, may comprise an siRNA of the present invention covalently or non-covalently attached to an aptamer. Aptamers are RNA or DNA single-strand or double-strand oligonucleic acids which bind to a target protein and do not generally exhibit non-specific effects. Aptamers can be modified for stability or other desired qualities in accordance with any nucleic acid modifications disclosed herein and/or known to one of skill in the art. Modifications to aptamers can be introduced anywhere in the molecule, such as the 5' or 3' termini, or at any internally defined modification site. For example, RNA aptamers can be stabilized with 2'-Fluoro or 2'-amino modified pyrimidines. Aptamers can also be linked to reporter molecules or linker chemistries and can be attached to beads or other solid support if necessary (e.g., 5' or 3' amino, thiol ester or biotin groups). Thioaptamers are aptamers which contain sulfur modifications at specific internucleoside phosphoryl sites, and may possess enhanced stability, nuclease resistance, target affinity and/or selectivity. Examples of thioaptamers include phosphoromonothioate (S-ODN) and phosphorodithioate (S2-ODN) oligodeoxy thioaptamers. For further information on aptamers and thioaptamers see U.S. Pat. Nos. 5,218,088 and 6,423,493.

It is to be understood that, in the context of the present invention, any of the siRNA molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, can be employed in the treatment of the diseases or disorders described herein.

Additional disorders which can be treated by the molecules and compositions of the present invention include all types of choroidal neovascularization (CNV), which occurs not only in wet AMD but also in other ocular pathologies such as ocular histoplasmosis syndrome, angiod streaks, ruptures in Bruch's membrane, myopic degeneration, ocular tumors and some retinal degenerative diseases.

An additional aspect of the present invention provides for methods of treating an apoptosis related disease. Methods for therapy of diseases or disorders associated with uncontrolled, pathological cell growth, e.g. cancer, psoriasis, autoimmune diseases, inter alia, and methods for therapy of diseases associated with ischemia and lack of proper blood flow, e.g. myocardial infarction (MI) and stroke, are provided. "Cancer" or "Tumor" refers to an uncontrolled growing mass of abnormal cells. These terms include both primary tumors, which may be benign or malignant, as well as secondary tumors, or metastases which have spread to other sites in the body. Examples of cancer-type diseases include, inter alia: carcinoma (e.g.: breast, colon and lung), leukemia such as B cell leukemia, lymphoma such as B-cell lymphoma, blastoma such as neuroblastoma and melanoma.

The invention also provides a composition comprising one or more of the compounds of the invention in a carrier, preferably a pharmaceutically acceptable carrier. This composition may comprise a mixture of two or more siRNAs for different genes or different siRNAs for the same gene. A composition comprising siRNA for the RTP801 gene and siRNA for the VEGF gene and/or the VEGF-R1 gene is envisaged.

Another compound of the invention comprises the above compound of the invention (structure A) covalently or non-covalently bound to one or more compounds of the invention (structure A). This compound may be delivered in a carrier, preferably a pharmaceutically acceptable carrier, and may be processed intracellularly by endogenous cellular complexes to produce one or more siRNAs of the invention. Another compound of the invention comprises the above compound of the invention (structure A) covalently or non-covalently bound to an siRNA for another gene, especially the VEGF gene and/or the VEGF-R1 gene.

This invention also comprises a novel chemical entity which is an RTP801 inhibitor, preferably an siRNA, chemically bound, covalently or non-covalently, to any of the above VEGF/VEGFR-1 inhibitory agents A particular chemical entity envisaged is an siRNA RTP801 inhibitor covalently bound to an antibody to VEGF or VEGF receptor-1. An additional chemical entity envisaged is a modified or unmodified DNA aptamer which targets VEGF receptor-1 covalently bound to an RTP801 siRNA disclosed herein. Without being bound by theory, the aptamer portion of such a pharmaceutical composition would bind VEGF receptor-1 and internalize into the cell, whereupon the siRNA portion of the molecule would inhibit RTP801 expression in the cell. Such a pharmaceutical would thus have the benefit of increased selectivity and targeting, as well as the additional benefits of combination therapy as disclosed herein. Methods of production of such novel chemical entities are known to those skilled in the art.

This invention also comprises a tandem double-stranded structure which comprises two or more siRNA sequences, which is processed intracellularly to form two or more different siRNAs, one inhibiting 801 and a second inhibiting VEGF/VEGFR-1 In a related aspect, this invention also comprises a tandem double-stranded structure which comprises two or more siRNA sequences, which is degraded intracellularly to form two or more different siRNAs, both inhibiting 801.

In particular, it is envisaged that a long oligonucleotide (typically about 80-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an 801 gene. In particular, it is envisaged that this oligonucleotide comprises sense and antisense siRNA sequences as depicted in Table A. Alternatively, the tandem shRNA construct may comprise sense and corresponding antisense siRNA sequence of an 801 gene and additionally sense and corresponding antisense siRNA sequence of a different gene such as VEGF or VEGF-R1.

As mentioned herein, siRNA against RTP801 may be the main active component in a pharmaceutical composition, or may be one active component of a pharmaceutical composition containing two or more siRNAs (or molecules which encode or endogenously produce two or more siRNAs, be it a mixture of molecules or one or more tandem molecule which encodes two or more siRNAs), said pharmaceutical composition further being comprised of one or more additional siRNA molecule which targets one or more additional gene. Simultaneous inhibition of RTP801 and said additional gene(s) will probably have an additive or synergistic effect for treatment of the diseases disclosed herein, according to the following:

Acute Renal Failure (ARF) and other microvascular disorders, as well as hearing disorders and pressure sores: the pharmaceutical composition for treatment of ARF may be comprised of the following compound combinations: 1) RTP801 siRNA and p53 siRNA dimers; 2) RTP801 and Fas siRNA dimers; 3) RTP801 and Bax siRNA dimers; 4) RTP801 and Fas siRNA dimers; 5) RTP801 and Bax siRNA dimers; 6) RTP801 and Noxa siRNA dimers; 7) RTP801 and Puma siRNA dimers; 8) RTP801 (REDD1) and RTP801L (REDD2) siRNA dimers; 9) RTP801siRNA, Fas siRNA and any of RTP801L siRNA p53 siRNA, Bax siRNA, Noxa siRNA or Puma siRNA to form trimers or polymers (i.e., tandem molecules which encode three or more siRNAs).

Further, additional pharmaceutical compositions for combination therapies for ARF, hearing disorders, pressure sores and any other disease or condition disclosed herein may comprise two siRNAs wherein the first siRNA is an RTP801 siRNA, preferably selected from Table A, and the second siRNA, which can be covalently or non-covalently bound to the first siRNA or admixed with the first siRNA, is an siRNA which targets a gene selected from the following group: tumor protein p53 binding protein, 2 (TP53BP2); leucine-rich repeats and death domain containing (LRDD); cytochrome b-245, alpha polypeptide (CYBA); activating transcription factor 3 (ATF3); caspase 2, apoptosis-related cysteine peptidase (neural precursor cell expressed, developmentally down-regulated 2) (CASP2); NADPH oxidase 3 (NOX3); harakiri, BCL2 interacting protein (HRK); complement component 1, q subcomponent binding protein (C1QBP); BCL2/adenovirus E1B 19 kDa interacting protein 3 (BNIP3); mitogen-activated protein kinase 8 (MAPK8); mitogen-activated protein kinase 14 (MAPK14); ras-related C3 botulinum toxin substrate 1 (rho family, small GTP binding protein Rac1); glycogen synthase kinase 3 beta (GSK3B); purinergic receptor P2X, ligand-gated ion channel, 7 (P2RX7); transient receptor potential cation channel, subfamily M, member 2 (TRPM2); poly (ADP-ribose) glycohydrolase (PARG); CD38 molecule (CD38); STEAP family member 4 (STEAP4); bone morphogenetic protein 2—BMP2; gap junction protein, alpha 1, 43 kDa (connexin 43) (GJA1); TYRO protein tyrosine kinase binding protein (TYROBP); connective tissue growth factor (CTGF); secreted phosphoprotein 1 (osteopontin, bone sialoprotein 1, early T-lymphocyte activation 1) (SPP1); reticulon 4 receptor (RTN4R); annexin A2 (ANXA2); ras homolog gene family, member A (RHOA); and dual oxidase 1 (DUOX1).

Macular degeneration (MD), diabetic retinopathy (DR), spinal cord injury: pharmaceutical compositions for treatment of MD, DR and spinal cord injury may be comprised of the following compound combinations: 1) RTP801 siRNA combined with either of VEGF siRNA, VEGF-R1 siRNA, VEGF R2 siRNA, PKCbeta siRNA, MCP1 siRNA, eNOS siRNA, KLF2 siRNA, RTP801L siRNA (either physically mixed or in a tandem molecule); 2) RTP801 siRNA in combination with two or more siRNAs of the above list (physically mixed or in a tandem molecule encoding three siRNAs, or a combination thereof).

COPD and respiratory disorders: the pharmaceutical composition for treatment of respiratory disorders may be comprised of the following compound combinations: RTP801 siRNA combined with siRNA against one or more of the following genes: elastases, matrix metalloproteases, phospholipases, caspases, sphingomyelinase, and ceramide synthase.

Additionally, RTP801 siRNA or any nucleic acid molecule comprising or encoding RTP801 siRNA can be linked (covalently or non-covalently) to an antibody or aptamer, in order to achieve enhanced targeting for treatment of the diseases disclosed herein, according to the following:

ARF: anti-Fas antibody (preferably neutralizing antibodies).

Macular degeneration, diabetic retinopathy, spinal cord injury: anti-Fas antibody or aptamer, anti-MCP1 antibody or aptamer, anti-VEGFR1 and anti-VEGFR2 antibody or aptamer. The antibodies should be preferably be neutralizing antibodies.

For further information on genes to be targeted in combination with RTP801 and siRNA sequences which can be used in such combination therapies see co-assigned PCT publication No.s WO06/023544 and WO07/084,684 and PCT application number PCT/IL 2007/001278 (assigned to the assignee of the instant application) which are hereby incorporated by reference in their entirety.

Any molecules, such as, for example, antisense DNA molecules which comprise the siRNA sequences disclosed herein (with the appropriate nucleic acid modifications) are particularly desirable and may be used in the same capacity as their corresponding siRNAs for all uses and methods disclosed herein.

The invention also comprises a method of treating a patient suffering from a disorder such as the disorders described herein comprising administering to the patient the above composition or compound in a therapeutically effective dose so as to thereby treat the patient.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

The polypeptides employed in the present invention may also be modified, optionally chemically modified, in order to improve their therapeutic activity. "Chemically modified"—when referring to the polypeptides, means a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

Additional possible polypeptide modifications (such as those resulting from nucleic acid sequence alteration) include the following:

"Conservative substitution"—refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

In an additional embodiment of the present invention, the RTP801 polypeptide or polynucleotide may be used to diagnose or detect macular degeneration in a subject. A detection method would typically comprise assaying for RTP801 mRNA or RTP801 polypeptide in a sample derived from a subject.

"Detection"—refers to a method of detection of a disease. This term may refer to detection of a predisposition to a disease, or to the detection of the severity of the disease.

By "homolog/homology", as utilized in the present invention, is meant at least about 70%, preferably at least about 75% homology, advantageously at least about 80% homology, more advantageously at least about 90% homology, even more advantageously at least about 95%, e.g., at least about 97%, about 98%, about 99% or even about 100% homology. The invention also comprehends that these polynucleotides and polypeptides can be used in the same fashion as the herein or aforementioned polynucleotides and polypeptides.

Alternatively or additionally, "homology", with respect to sequences, can refer to the number of positions with identical nucleotides or amino acid residues, divided by the number of nucleotides or amino acid residues in the shorter of the two sequences, wherein alignment of the two sequences can be determined in accordance with the Wilbur and Lipman algorithm ((1983) Proc. Natl. Acad. Sci. USA 80:726); for instance, using a window size of 20 nucleotides, a word length of 4 nucleotides, and a gap penalty of 4, computer-assisted analysis and interpretation of the sequence data, including alignment, can be conveniently performed using commercially available programs (e.g., Intelligenetics™ Suite, Intelligenetics Inc., CA). When RNA sequences are said to be similar, or to have a degree of sequence identity or homology with DNA sequences, thymidine (T) in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally or alternatively, amino acid sequence similarity or homology can be determined, for instance, using the BlastP program (Altschul et al., Nucl. Acids Res. 25:3389-3402) and available at NCBI. The following references provide algorithms for comparing the relative identity or homology of amino acid residues of two polypeptides, and additionally, or alternatively, with respect to the foregoing, the teachings in these references can be used for determining percent homology: Smith et al., (1981) Adv. Appl. Math. 2:482-489; Smith et al., (1983) Nucl. Acids Res. 11:2205-2220; Devereux et al., (1984) Nucl. Acids Res. 12:387-395;

Feng et al., (1987) J. Molec. Evol. 25:351-360; Higgins et al., (1989) CABIOS 5:151-153; and Thompson et al., (1994) Nucl. Acids Res. 22:4673-4680.

"Having at least X % homolgy"—with respect to two amino acid or nucleotide sequences, refers to the percentage of residues that are identical in the two sequences when the sequences are optimally aligned. Thus, 90% amino acid sequence identity means that 90% of the amino acids in two or more optimally aligned polypeptide sequences are identical.

An additional embodiment of the present invention concerns a pharmaceutical composition comprising an RTP801 inhibitor in a therapeutically affective amount as an active ingredient and a pharmaceutically acceptable carrier. The inhibitor may be a biological inhibitor, an organic molecule, a chemical molecule, etc. said pharmaceutical composition may comprise an RTP801 inhibitor which is a polynucleotide which comprises consecutive nucleotides having a sequence which is an antisense sequence to the sequence set forth in FIG. 1 (SEQ ID No: 1). Further, the RTP801 inhibitor may be a vector comprising these polynucleotides. Additionally, the RTP801 inhibitor may be a monoclonal antibody which specifically binds to an epitope comprising 4-25 amino acids set forth in FIG. 2 (SEQ ID No:2), or an RNA molecule which targets the RTP801 gene mRNA such as an siRNA molecule (optionally depicted in Table A and in particular, siRNA Nos: 102, 103 and 106) or a ribozyme.

The active ingredients of the pharmaceutical composition can include oligonucleotides that are nuclease resistant needed for the practice of the invention or a fragment thereof shown to have the same effect targeted against the appropriate sequence(s) and/or ribozymes. Combinations of active ingredients as disclosed in the present invention can be used, including combinations of antisense sequences.

An additional embodiment of the present invention provides for the use of a therapeutically effective dose of an RTP801 inhibitor for the preparation of a medicament for promoting recovery in a patient suffering from spinal cord disease or injury. In one embodiment the inhibitor is preferably an siRNA. In another embodiment the inhibitor is preferably Structure A depicted herein.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

BRIEF DESCRIPTION OF THE FIGURES

FIG. 1 details the coding sequence of the RTP801 gene (SEQ ID NO:1);

FIG. 2 details the amino acid sequence of the RTP801 polypeptide (SEQ ID NO:2).

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic syntheses*: Vol. 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

The features of the present invention disclosed in the specification, the claims and/or the drawings may both separately and in any combination thereof be material for realizing the invention in various forms thereof.

Example 1

General Materials and Methods

Cell Culture

The first human cell line, namely HeLa cells (American Type Culture Collection) were cultured as follows: Hela cells (American Type Culture Collection) were cultured as described in Czauderna F et al. (Czauderna, F., Fechtner, M., Aygun, H., Arnold, W., Klippel, A., Giese, K. & Kaufmann, J. (2003). Nucleic Acids Res, 31, 670-82).

The second human cell line was a human keratinozyte cell line which was cultivated as follows: Human keratinocytes were cultured at 37° C. in Dulbecco's modified Eagle medium (DMEM) containing 10% FCS.

The mouse cell line was B16V (American Type Culture Collection) cultured at 37° C. in Dulbecco's modified Eagle medium (DMEM) containing 10% FCS. Culture conditions were as described in Methods Find Exp Clin Pharmacol. 1997 May; 19(4):231-9:

In each case, the cells were subject to the experiments as described herein at a density of about 50,000 cells per well and the double-stranded nucleic acid according to the present invention was added at 20 nM, whereby the double-stranded nucleic acid was complexed using 1 µg/ml of a proprietary lipid.

Induction of Hypoxia-Like Condition

The cells were treated with $CoCl_2$ for inducing a hypoxia-like condition as follows: siRNA transfections were carried out in 10-cm plates (30-50% confluency) as described by (Czauderna et al., 2003; Kretschmer et al., 2003). Briefly, siRNA were transfected by adding a preformed 10× concentrated complex of GB and lipid in serum-free medium to cells in complete medium. The total transfection volume was 10 ml. The final lipid concentration was 1.0 µg/ml; the final siRNA concentration was 20 nM unless otherwise stated. Induction of the hypoxic responses was carried out by adding $CoCl_2$ (100 µM) directly to the tissue culture medium 24 h before lysis.

Preparation of Cell Extracts and Immuno Blotting

The preparation of cell extracts and immuno blot analysis were carried out essentially as described by Klippel et al. ((1998). Mol Cell Biol, 18, 5699-711; Klippel, (1996). Mol Cell Biol, 16, 4117-27). Polyclonal antibodies against full length RTP801 were generated by immunising rabbits with recombinant RTP801 protein producing bacteria from pET19-b expression vector (Merck Biosciences GmbH, Schwalbach, Germany). The murine monoclonal anti-p110a and anti-p85 antibodies have been described by Klippel et al. (supra).

Example 2

Experimental Models, Methods and Results

Macular Degeneration

The compounds of the present invention are tested in the following an animal model of Choroidal neovascularization (CNV). This hallmark of wet AMD is induced in model animals by laser treatment.

A) Mouse Model

Choroidal Neovascularization (CNV) Induction

Choroid neovascularization (CNV), a hallmark of wet AMD, is triggered by laser photocoagulation (532 nm, 200 mW, 100 ms, 75 µm) (OcuLight GL, Iridex, Mountain View, Calif.) performed on both eyes of each mouse on day 0 by a single individual masked to drug group assignment. Laser spots are applied in a standardized fashion around the optic nerve, using a slit lamp delivery system and a cover slip as a contact lens. For evaluation, the eyes are enucleated and fixed with 4% paraformaldehyde for 30 min at 4° C. The neurosensory retina is detached and severed from the optic nerve. The remaining RPE-choroid-sclera complex is flat mounted in Immu-Mount (Vectashield Mounting Medium, Vector) and coverslipped. Flat mounts are examined with a scanning laser confocal microscope (TCS SP, Leica, Germany). Vessels are visualized by exciting with blue argon laser. Horizontal optical sections (1 µm step) are obtained from the surface of the RPE-choroid-sclera complex. The deepest focal plane in which the surrounding choroidal vascular network connecting to the lesion can be identified is judged to be the floor of the lesion. Any vessel in the laser treated area and superficial to this reference plane is judged as CNV. Images of each section are digitally stored. The area of CNV-related fluorescence is measured by computerized image analysis using the Leica TCS SP software. The summation of whole fluorescent area in each horizontal section is used as an index for the volume of CNV. The siRNA compounds disclosed herein are tested in this animal model which shows that these siRNAs treat and/or prevent AMD and thus may be used to treat this condition.

B) Primate Model

CNV Induction

Male cynomolgus monkeys (*Macaca fascicularis*) 2-6 years of age are used for the study. Choroidal neovascularization (CNV) is induced by perimacular laser treatment of both eyes prior to dose administration. Lesions are placed in the macula with a laser [OcuLight GL (532 nm) Laser Photocoagulator with an IRIS Medical® Portable Slit Lamp Adaptor]. The approximate laser parameters are as follows: spot size: 50-100 µm diameter; laser power: 300-700 milliwatts; exposure time: 0.1 seconds. Immediately following laser treatment, both eyes of animals are subjected to a single intravitreal injection. Left eye is generally dosed with 350 ug of synthetic stabilized siRNA against RTP801 in a final volume of 50 ul, whereas the contralateral eye receives 50 ul of PBS (vehicle). Monkeys are generally euthanized at day 6 following CNV induction. Their eyes are enucleated and posterior pole is flattened. The fovea region is excised and separated into choroids and neuroretina which are separately frozen in liquid nitrogen to be subsequently used for RNA extraction and real time PCR evaluation of RTP801 expression. Fluorescein angiograms are performed pre-study, and at the end of weeks 1, 2, and 3 following CNV induction. Photographs are taken, using a fundus camera (TRC-50EX Retina Camera). Images are captured using the TOPCON IMAGEnet™ system. Fluorescein dye (10% fluorescein sodium, approximately 0.1 mL/kg) is injected via vascular access ports. Photographs are taken at several timepoints following dye injection, to include the arterial phase, early arteriovenous phase and several late arteriovenous phases in order to evaluate neovascularization and to monitor leakage of fluorescein associated with CNV lesions. Interpretation and analysis of the fluorescein angiograms is independently conducted by two ophthalmologists. The siRNA compounds disclosed herein are tested in this animal model which shows that these siRNAs treat and/or prevent AMD and thus may be used to treat this condition.

COPD and Emphysema

The compounds of the present invention are tested in the following animal models:

Cigarette smoke-induced emphysema model: chronic exposure to cigarette smoke causes emphysema in several animals such as, inter alia, mouse, guinea pig.

Lung protease activity as a trigger of emphysema.

VEGFR inhibition model of emphysema.

Bronchial instillation with human neutrophil/pancreatic elastase in rodents.

MMP (matrix metalloprotease)-induced emphysema.

Inflammation-induced emphysema.

Additionally, emphysema models may be generated through genetic means (e.g., mice carrying the TSK mutation), and emphysematous animals may be generated by known modifiers of susceptibility to emphysema such as, inter alia, lung injury, alveolar hypoplasia, hyperoxia, glucocorticoid treatment and nutrition. The siRNA compounds disclosed herein are tested in these animal models which show that these compounds treat and/or prevent emphysema, chronic bronchitis and COPD.

Exposure to Cigarette Smoking (CS)

Exposure is carried out (7 h/day, 7 days/week) by burning 2R4F reference cigarettes (2.45 mg nicotine per cigarette; purchased from the Tobacco Research Institute, University of Kentucky, Lexington, Ky., USA) using a smoking machine (Model TE-10, Teague Enterprises, Davis, Calif., USA). Each smoldering cigarette is puffed for 2 s, once every minute for a total of eight puffs, at a flow rate of 1.05 L/min, to provide a standard puff of 35 cm$^3$. The smoke machine is adjusted to produce a mixture of sidestream smoke (89%) and mainstream smoke (11%) by burning five cigarettes at one time. Chamber atmosphere is monitored for total suspended particulates and carbon monoxide, with concentrations of 90 mg/m3 and 350 ppm, respectively. After exposing the mice to CS or instillation of RTP801 expressing plasmid, the mice are anesthetized with halothane and the lungs are inflated with 0.5% low-melting agarose at a constant pressure of 25 cm as previously described[6]. The inflated lungs are fixed in 10% buffered formalin and embedded in paraffin. Sections (5 µm) are stained with hematoxylin and eosin. Mean alveolar diameter, alveolar length, and mean linear intercepts are determined by computer-assisted morphometry with the Image Pro Plus software (Media Cybernetics, Silver Spring, Md., USA). The lung sections in each group are coded and representative images (15 per lung section) are acquired by an investigator masked to the identity of the slides, with a Nikon E800 microscope, 20× lens.

Bronchoalveolar Lavage (BAL) and Phenotyping

Following exposure to CS or instillation of RTP801 expressing plasmid, the mice are anesthetized with sodium pentobarbital. The BAL fluid collected from the lungs of the mice is centrifuged (500 g at 4° C.), and the cell pellet is resuspended in phosphate-buffered saline. The total number of cells in the lavage fluid is determined, and 2×104 cells are cytocentrifuged (Shandon Southern Products, Pittsburgh, Pa., USA) onto glass slides and stained with Wright-Giemsa stain. Differential cell counts are performed on 300 cells, according to standard cytologic techniques.

Identification of Alveolar Apoptotic Cell Populations in the Lungs.

To identify the different alveolar cell types undergoing apoptosis in the lungs, an immunohistochemical staining of active caspase 3 is performed in the lung sections from the room air (RA) as well as CS exposed mice. To identify the apoptotic type II epithelial cells in the lungs, after active caspase 3 labeling, the lung sections are incubated first with anti-mouse surfactant protein C (SpC) antibody and then with an anti-rabbit Texas red antibody. Apoptotic endothelial cells are identified by incubating the sections first with the anti-mouse CD 31 antibody and then with the biotinylated rabbit anti-mouse secondary antibody. The lung sections are rinsed in PBS and then incubated with the streptavidin-Texas red conjugated complex. The apoptotic macrophages in the lungs are identified by incubating the sections first with the rat anti-mouse Mac-3 antibody and then with the anti-rat Texas red antibody. Finally, DAPI is applied to all lung sections, incubated for 5 minutes, washed and mounted with Vectashield HardSet mounting medium. DAPI and fluorescein are visualized at 330-380 nm and 465-495 nm, respectively. Images of the lung sections are acquired with the Nikon E800 microscope, 40× lens.

Immunohistochemical Localization of Active Caspase-3

Immunohistochemical staining of active caspase-3 assay is performed using anti-active caspase-3 antibody and the active caspase-3-positive cells are counted with a macro, using Image Pro Plus program. The counts are normalized by the sum of the alveolar profiles herein named as alveolar length and expressed in µm. Alveolar length correlates inversely with mean linear intercept, i.e., as the alveolar septa are destroyed, mean linear intercepts increases as total alveolar length, i.e., total alveolar septal length decreases.

Caspase 3 Activity Assay

The caspase-3/7 activity is measured in lung tissue extracts using a fluorometric assay according to the manufacturer's instructions. Snap-frozen lung tissue (n=3 per group) is homogenized with the assay buffer, followed by sonication and centrifugation at 800×g. After removal of nuclei and cellular debris, the supernatant (300 µg protein) is then incubated with the pro-fluorescent substrate at room temperature for 1 h and the fluorescence intensity was measured utilizing a Typhoon phosphoimager (Amersham Biosciences, Inc., Piscataway, N.J., USA). The results are expressed as the rate of specific caspase-3 substrate cleavage, expressed in units of caspase 3 enzymatic activity, normalized by total protein concentration. Active recombinant caspase 3 was utilized as the assay standard (0-4 U). Tissue lysates without substrate, assay buffer alone, and lysates with caspase 3 inhibitor were utilized as negative controls.

Immunohistochemical Localization of 8-oxo-dG

For the immunohistochemical localization and quantification of 8-oxo-dG, lung sections from the mice exposed to CS or instilled with RTP801 expressing plasmid are incubated with anti-8-oxo-dG antibody and stained using InnoGenex™ Iso-IHC DAB kit using mouse antibodies. The 8-oxo-dG-positive cells are counted with a macro (using Image Pro Plus), and the counts were normalized by alveolar length as described.

Instillation of Plasmid DNA into Mouse Lungs

Plasmid DNA of RTP801 expressing and control vectors are prepared using an endotoxin-free DNA isolation kit. For intra-tracheal instillation, 50 ug of plasmid DNA is delivered in 80 ul sterile perfluorocarbon. The oxygen carrying properties of perfluorocarbon make it well-tolerated at these volumes, while its physical-chemical properties allow for extremely efficient distal lung delivery when instilled intratracheally. Mice are anesthetized by brief inhalational halothane exposure, the tongue is gently pulled forward by forceps and the trachea instilled with perfluorocarbon solution applied at the base of the tongue via a blunt angiocatheter.

Instillation of siRNA into Mouse Lungs.

Mice are anesthetized with an intra-peritoneal injection of Ketamine/Xylazine (15/22 mg/kg). 50 µg of siRNA is instilled intranasally in 50 µl volume of 0.9% NaCl by delivering five consecutive 10 µl portions. At the end of the intranasal instillation, the mouse's head is held straight up for 1 minute to ensure that all the instilled solution drains inside.

For further information, see: Rangasamy et al., *Submitted to Journal of Clininical Investigation get ref*; Kasahara, et al., Am J Respir Crit. Care Med Vol 163. pp 737-744, 2001; Kasahara, et al., *J. Clin. Invest.* 106:1311-1319 (2000); and a review on the topic: Tuder, et al., *Pulmonary Pharmacology & Therpaeutics* 2002.

Microvascular Disorders

The compounds of the present invention are tested in animal models of a range of microvascular disorders as described below. The siRNA compounds disclosed herein are tested in these animal models which show that these compounds treat and/or prevent diseases due to microvascular disorders.

Diabetic Retinopathy

RTP801 promotes neuronal cell apoptosis and generation of reactive oxygen species in vitro. The inventor of the current invention also found that in RTP801 knockout (KO) mice subjected to the model of retinopathy of prematurity (ROP), pathologic neovascularization NV was reduced under hypoxic conditions, despite elevations in VEGF, whereas the lack of this gene did not influence physiologic neonatal retinal NV. Moreover, in this model, lack of RTP801 was also protective against hypoxic neuronal apoptosis and hyperoxic vaso-obliteration.

Experiment 1

Diabetes is induced in 8 wk old RTP801 KO and C57/129sv wildtype (WT) littermate mice by intraperitoneal injection of STZ. After 4 weeks, ERG (single white flash, $1.4 \times 10^4$ ftc, 5 ms) is obtained from the left eye after 1 hour of dark adaptation. RVP is assessed from both eyes using the Evans-blue albumin permeation technique.

Experiment 2

Diabetes is induced in RTP801 knockout and in control wild type mice with the matched genetic background. In addition, it may be induced in C57B16 mice, which are subsequently used for intravitreal injection of anti-RTP801 and control siRNAs. For diabetes induction, the mice are injected with streptozotocin (STZ 90 mg/kg/d for 2 days after overnight fast). Animal physiology is monitored throughout the study for changes in blood glucose, body weight, and hematocrit. Vehicle-injected mice serve as controls. The animals are treated by intravitreal injections of 1 ug of REDD14 anti-RTP801 siRNA or 1 ug of anti-GFP control siRNA. siRNA is injected twice in the course of the study—on day 0, when the first STZ injection is performed, and on day 14 after the STZ injection. Retinal vascular leakage is measured using the Evans-blue (EB) dye technique on the animals after 4 weeks duration of diabetes. Mice have a catheter implanted into the right jugular vein 24 hours prior to Evans Blue (EB) measurements. Retinal permeability measurements in both eyes of each animal are conducted according to a standard Evans-blue protocol.

The siRNA compounds disclosed herein are tested in this animal model which shows that these compounds treat diabetic retinopathy.

Retinopathy of Prematurity

Retinopathy of prematurity is induced by exposing the test animals to hypoxic and hyperoxic conditions, and subsequently testing the effects on the retina. Results show that RTP801 KO mice were protected from retinopathy of prematurity, thereby validating the protective effect of RTP801 inhibition.

Myocardial Infarction

Myocardial infarction is induced by Left Anterior Descending artery ligation in mice, both short term and long term. Results: reduction of TnT and CPK-MB fraction levels at 24 hrs postinfarct in the blood and better echocardiogram (ejection fraction volume) at 28 days postinfarct in RTP801 KO mice.

Microvascular Ischemic Conditions

Animal models for assessing ischemic conditions include:

1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.

2. Transient middle cerebral artery occlusion (MCAO)—a 90 to 120 minutes transient focal ischemia is performed in adult, male Sprague Dawley rats, 300-370 gr. The method employed is the intraluminal suture MCAO (Longa et al., Stroke, 30, 84, 1989, and Dogan et al., J. Neurochem. 72, 765, 1999). Briefly, under halothane anesthesia, a 3-O-nylon suture material coated with Poly-L-Lysine is inserted into the right internal carotid artery (ICA) through a hole in the external carotid artery. The nylon thread is pushed into the ICA to the right MCA origin (20-23 mm). 90-120 minutes later the thread is pulled off, the animal is closed and allowed to recover.

3. Permanent middle cerebral artery occlusion (MCAO)—occlusion is permanent, unilateral-induced by electrocoagulation of MCA. Both methods lead to focal brain ischemia of the ipsilateral side of the brain cortex leaving the contralateral side intact (control). The left MCA is exposed via a temporal craniectomy, as described for rats by Tamura A. et al., *J Cereb Blood Flow Metab.* 1981; 1:53-60. The MCA and its lenticulostriatal branch are occluded proximally to the medial border of the olfactory tract with microbipolar coagulation. The wound is sutured, and animals returned to their home cage in a room warmed at 26° C. to 28° C. The temperature of the animals is maintained all the time with an automatic thermostat.

The siRNA compounds disclosed herein are tested in this animal model which shows that these compounds treat microvascular ischemic conditions.

Acute Renal Failure (ARF)

Testing active siRNA for treating ARF may be done using sepsis-induced ARF or ischemia-reperfusion-induced ARF.

Sepsis Induced ARF

Two predictive animal models of sepsis-induced ARF are described by Miyaji T, Hu X, Yuen P S, Muramatsu Y, Iyer S, Hewitt S M, Star R A, 2003, Kidney Int. November; 64(5): 1620-31. These two models are lipopolysaccharide administration and cecal ligation puncture in mice, preferably in aged mice. The siRNA compounds disclosed herein are tested in these animal models which show that these compounds treat and/or prevent sepsis-induced ARF Ischemia-Reperfusion-Induced ARF This predictive animal model is described by Kelly et al., 2003, J Am Soc Nephrol.; 14(1): 128-38.

Ischemia-reperfusion injury is induced in rats following 45 minutes bilateral kidney arterial clamp and subsequent release of the clamp to allow 24 hours of reperfusion. 250 µg of RTP801 siRNA or GFP siRNA (negative control) are injected into the jugular vein 2 hrs prior to and 30 minutes following the clamp. Additional 250 µg of siRNA are given via the tail vein at 4 and 8 hrs after the clamp. siRNA against GFP serves as a negative control. ARF progression is monitored by measurement of serum creatinine levels before and 24 hrs post surgery. At the end of the experiment, the rats are perfused via an indwelling femoral line with warm PBS followed by 4% paraformaldehyde. The left kidneys are removed and stored in 4% paraformaldehyde for subsequent histological analysis. Acute renal failure is frequently defined as an acute increase of the serum creatinine level from baseline. An increase of at least 0.5 mg per dL or 44.2 µmol per L of serum creatinine is considered as an indication for acute renal failure. Serum creatinine is measured at time zero before the surgery and at 24 hours post ARF surgery. The siRNA compounds disclosed herein are tested in this animal model which show that these compounds treat and/or prevent Ischemia-Reperfusion-Induced ARF Deafness Cisplatin-Induced Ototoxicity Cisplatin-induced ototoxicity is induced in cochlear and vestibular organotypic cultures. Postnatal day 3-4 rat pups are used to prepare the cochlear and vestibular organotypic cultures as detailed in Zhang et al., Neuroscience 120 (2003) 191-205. Cochleae are carefully dissected out and the cochlear tissue containing the spiral ganglion, organ of Corti and the middle turn are removed to prepare the organotypic cultures as described in Zhang et al. The cultures are placed in a $CO_2$ incubator for 24 h for conditioning before treatment. After conditioning, the cultures are treated with cisplatin alone at 1, 5 or 10 µg/ml for 48 h. To study the protective effect of RTP801 siRNA, the cochlear explants (5 cochleas per group) are treated for 48 h with 10 µg/ml cisplatin and varying concentrations of RTP801 siRNA with or without Lipofectamine. Untreated control cultures and cultures treated with RTP801 siRNA for 48 h are run in parallel. At the end of the experiments, the cultures are fixed with 10% formalin and stained with FITC-conjugated phalloidin. The numbers of inner hair cells and outer hair cells per 0.25 mm length of the cochlean are counted and the mean number of hair cells are determined for each treatment. The siRNA compounds disclosed herein are tested in this animal model which show that these compounds treat and/or prevent cisplatin-induced ototoxicity Gentamicin-Induced Ototoxicity Chinchillas are either treated with gentamicin sulfate alone for 5 days (125-300 mg/kg, intramuscular) or in combination with RTP801 siRNA. The siRNA molecules are administered topically onto the round window membrane of the cochlea two days prior to and during the 5 days exposure to gentamicin. At the end of the treatment, the animals are killed by exposure to carbon dioxide and decapitation. The cochleas are removed and prepared for staining with FITC-conjugated phalloidin to determine the numbers of inner hair cells and outer hair cells in the cochlean tissue (as described in Ding et al., Hearing Research 164 (2002) 115-126 and in Wang et al., The Journal of Neuroscience 23(24):8596-8607). The siRNA compounds disclosed herein are tested in this animal model which show that these compounds treat and/or prevent gentamicin-induced ototoxicity Acoustic Trauma Pigmented guinea pigs are used in the acoustic trauma study (described in Wang et al., The Journal of Neuroscience 23(24):8596-8607). RTP801 siRNA molecules are administered topically onto the round window membrane of the cochlea over a period of 7 days. Untreated left cochleae serves as controls for the effectiveness of the acoustic trauma on causing auditory hair cell loss and loss of hearing function. Animals are exposed to acoustic trauma [approximately 6 kHz, 120 dB sound pressure level (SPL), 30 min], and audiograms of both ears are derived from the compound action potentials (CAPs) recorded from the auditory nerves via chronic round window membrane electrodes. The CAP audiograms from both ears are measured daily in waking animals. 30 d after sound exposure, animals are sacrificed, and their cochleae are prepared for a quantitative evaluation of hair cell losses using scanning electron microscopy in order to count all hair cells for the entire length of the cochlear duct. The siRNA compounds disclosed herein are tested in this animal model which show that these compounds treat and/or prevent acoustic trauma-induced ototoxicity For further models, methods and results relating to RTP801 siRNAs, see PCT publication No. WO06/023544A2 and PCT patent application No. PCT/US2007/01468, co-assigned to the assignee of the present invention, which are hereby incorporated by reference in their entirety Model Systems of Pressure Sores or Pressure Ulcers Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA compounds) for treating pressure sore, ulcers and similar wounds is performed in the mouse model described in Reid et al., (J Surgical Research. 116:172-180, 2004).

An additional rabbit model (described by Mustoe et al, (JCI, 1991. 87(2):694-703; Ahn and Mustoe, Ann Pl Surg, 1991. 24(1):17-23) is used for testing the siRNA compounds of the invention. siRNA compounds according to the invention e.g. those in Table A are tested in these animal models where it is shown that these siRNA compounds treat and prevent pressure sores and ulcers.

Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

Uptake of siRNA molecules into neurons following injection into injured spinal-cord:

The uptake of Cy3 labeled siRNA (delivered by injection into the injured cord) in different types of cells is examined following spinal cord contusion in injured rats and in uninjured rats. Sagittal cryosections are produced and immunostaining using different groups of antibodies is performed in order to determine whether uptake has occurred in neurons, astroglia, oligdendroglia and/or macrophages/microglia. Exemplary markers for neurons are NeuN, or GAP43; exemplary markers for astroglia and potential neural stem cells are GFAP, nestin or vimentin; exemplary markers for oligdendroglia are NG2 or APC; exemplary markers for macrophages/microglia are ED1 or Iba-1 (Hasegawa et al., 2005. Exp Neurol 193 394-410).

Rats are injected with two different doses of Cy3 labeled siRNA (1 µg/µl, 10 µg/µl) and are left for 1 and 3 days before sacrifice. According to results achieved by the Asignee of the present invention, immunostaining with antibodies to MAP2 has identified uptake of label into dendrites and into cell bodies of neurons including motorneurons. Staining with other antibodies specific to astrocytes or macrophages revealed lower uptake of Cy3 labeled siRNA as compared to neurons. These results indicate that siRNA molecules injected to the injured spinal-cord reach the cell body and dendrites of neurons including motorneurons. The siRNA compounds disclosed herein are tested in this animal model which show that these compounds treat spinal cord injury.

Model Systems of Glaucoma

Testing the active inhibitors of the invention (such as siRNA) for treating or preventing glaucoma is done in the animal model for example as described by Pease et al., J. Glaucoma, 2006, 15(6):512-9 (Manometric calibration and comparison of TonoLab and TonoPen tonometers in rats with experimental glaucoma and in normal mice).

siRNA compounds of the invention including those according to Table A are tested in this animal model which show that these siRNA compounds treat and/or prevent glaucoma.

Model Systems of Ischemia/Reperfusion Injury Following Lung Transplantation in Rats Testing the active inhibitors of the invention (such as siRNA) for treating or preventing ischemia/reperfusion injury or hypoxic injury following lung transplantation is done in one or more of the experimental animal models, for example as described by Mizobuchi et al., (2004. J. Heart Lung Transplant, 23:889-93); Huang, et al., (1995. J. Heart Lung Transplant. 14: S49); Matsumura, et al., (1995. Transplantation 59: 1509-1517); Wilkes, et al., (1999. Transplantation 67:890-896); Naka, et al., (1996. Circulation Research, 79: 773-783).

siRNA compounds of the invention e.g. those according to Table A are tested in these animal models, which show that these siRNA compounds treat and/or prevent ischemia-reperfusion injury following lung transplantation and thus may be used in conjunction with transplant surgery.

Model Systems of Acute Respiratory Distress Syndrome

Testing the active inhibitors of the invention (such as siRNA) for treating acute respiratory distress syndrome is done in the animal model as described by Chen, et al (J Biomed Sci. 2003; 10(6 Pt 1):588-92). siRNA compounds of the invention e.g. those according to Table A are tested in this animal model which shows that these siRNAs treat and/or prevent acute respiratory distress syndrome and thus may be used to treat this condition.

Example 3

Preparation of siRNAs

Using proprietary algorithms and the known sequence of gene RTP801 (SEQ ID NO: 1), the sequences of many potential siRNAs were generated. siRNA molecules according to the above specifications were prepared essentially as described herein.

The siRNAs of the present invention can be synthesized by any of the methods which are well-known in the art for synthesis of ribonucleic (or deoxyribonucleic) oligonucleotides. For example, a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The siRNA molecules of the invention may be synthesized by procedures known in the art e.g. the procedures as described in Usman et al., 1987, *J. Am. Chem. Soc.*, 109, 7845; Scaringe et al., 1990, *Nucleic Acids Res.*, 18, 5433; Wincott et al., 1995, *Nucleic Acids Res.* 23, 2677-2684; and Wincott et al., 1997, *Methods Mol. Bio.*, 74, 59, and may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

Alternatively, the nucleic acid molecules of the present invention can be synthesized separately and joined together post-synthetically, for example, by ligation (Moore et al., 1992, *Science* 256, 9923; Draper et al., International PCT publication No. WO93/23569; Shabarova et al., 1991, *Nucleic Acids Research* 19, 4247; Bellon et al., 1997, *Nucleosides & Nucleotides,* 16, 951; Bellon et al., 1997, *Bioconjugate Chem.* 8, 204), or by hybridization following synthesis and/or deprotection. The siRNA molecules of the invention can also be synthesized via a tandem synthesis methodology, as described in US patent application publication No. US2004/0019001 (McSwiggen) wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

For further information, see PCT publication No. WO 2004/015107 (ATUGEN).

Table A details various novel siRNA molecules which were generated for gene RTP801. Any one of the siRNA molecules disclosed herein are novel and considered a part of the present invention. (Chimp refers to chimpanzee)

TABLE A

| No | Species specificity | Sense siRNA strand | SEQ ID NO (sense strand) | AntiSense siRNA strand | SEQ ID NO (antisense strand) | Coordinates on gi\|56676369\|ref\| NM_019058.2 (*Homo sapiens*) |
|---|---|---|---|---|---|---|
| 100 | Human, Chimp. | UCCGAGUCAUCAAGAAGAA | 3 | UUCUUCUUGAUGACUCGGA | 37 | [843-861] (19/19) |
| 103 | Human, Chimp. | GAGUCAUCAAGAAGAAGCU | 4 | AGCUUCUUCUUGAUGACUC | 38 | [846-864] (19/19) |
| 95 | Human, Chimp. | UGGCUUCCGAGUCAUCAAG | 5 | CUUGAUGACUCGGAAGCCA | 39 | [838-856] (19/19) |
| 105 | Human, Chimp., Rabbit | GUCAUCAAGAAGAAGCUGU | 6 | ACAGCUUCUUCUUGAUGAC | 40 | [848-866] (19/19) |
| 40 | Human, Chimp. | AGACACGGCUUACCUGGAU | 7 | AUCCAGGUAAGCCGUGUCU | 41 | [406-424] (19/19) |
| 108 | Human, Chimp., Rabbit | AUCAAGAAGAAGCUGUACA | 8 | UGUACAGCUUCUUCUUGAU | 42 | [851-869] (19/19) |
| 127 | Human, Chimp., Rabbit | CAGCUGCUCAUUGAGGAGU | 9 | ACUCCUCAAUGAGCAGCUG | 43 | [878-896] (19/19) |

TABLE A-continued

| No | Species specificity | Sense siRNA strand | SEQ ID NO (sense strand) | AntiSense siRNA strand | SEQ ID NO (antisense strand) | Coordinates on gi\|56676369\|ref\| NM_019058.2 (Homo sapiens) |
|---|---|---|---|---|---|---|
| 102 | Human, Chimp. | CGAGUCAUCAAGAAGAAGC | 10 | GCUUCUUCUUGAUGACUCG | 44 | [845-863] (19/19) |
| 96 | Human, Chimp. | GGCUUCCGAGUCAUCAAGA | 11 | UCUUGAUGACUCGGAAGCC | 45 | [839-857] (19/19) |
| 82 | Human, Chimp. | GCAAAGAACUACUGCGCCU | 12 | AGGCGCAGUAGUUCUUUGC | 46 | [585-603] (19/19) |
| 56 | Human | GAUGAACACUUGUGUGCCA | 13 | UGGCACACAAGUGUUCAUC | 47 | [467-485] (19/19) |
| 49 | Human | CCCUGAGGAUGAACACUUG | 14 | CAAGUGUUCAUCCUCAGGG | 48 | [460-478] (19/19) |
| 38 | Human, Chimp. | AGGAAGACACGGCUUACCU | 15 | AGGUAAGCCGUGUCUUCCU | 49 | [402-420] (19/19) |
| 42 | Human, Chimp. | UCAGUGACCCUGAGGAUGA | 16 | UCAUCCUCAGGGUCACUGA | 50 | [453-471] (19/19) |
| 43 | Human, Chimp. | CAGUGACCCUGAGGAUGAA | 17 | UUCAUCCUCAGGGUCACUG | 51 | [454-472] (19/19) |
| 125 | Human, Chimp. | AACAGCUGCUCAUUGAGGA | 18 | UCCUCAAUGAGCAGCUGUU | 52 | [876-894] (19/19) |
| 124 | Human, Chimp. | GAACAGCUGCUCAUUGAGG | 19 | CCUCAAUGAGCAGCUGUUC | 53 | [875-893] (19/19) |
| 121 | Human, Chimp. | UCGGAACAGCUGCUCAUUG | 20 | CAAUGAGCAGCUGUUCCGA | 54 | [872-890] (19/19) |
| 128 | Human, Chimp., Rabbit | AGCUGCUCAUUGAGGAGUG | 21 | CACUCCUCAAUGAGCAGCU | 55 | [879-897] (19/19) |
| 117 | Human, Chimp. | AAGCUGUACAGCUCGGAAC | 22 | GUUCCGAGCUGUACAGCUU | 56 | [860-878] (19/19) |
| 131 | Human, Rabbit, Chimp. | UGCUCAUUGAGGAGUGUUG | 23 | CAACACUCCUCAAUGAGCA | 57 | [882-900] (19/19) |
| 106 | Human, Chimp., Rabbit | UCAUCAAGAAGAAGCUGUA | 24 | UACAGCUUCUUCUUGAUGA | 58 | [849-867] (19/19) |
| 89 | Human, Chimp. | CUGUUUAGCUCCGCCAACU | 25 | AGUUGGCGGAGCUAAACAG | 59 | [776-794] (19/19) |
| 57 | Human | AUGAACACUUGUGUGCCAA | 26 | UUGGCACACAAGUGUUCAU | 60 | [468-486] (19/19) |
| 61 | Human | ACACUUGUGUGCCAACCUG | 27 | CAGGUUGGCACACAAGUGU | 61 | [472-490] (19/19) |
| 53 | Human | GAGGAUGAACACUUGUGUG | 28 | CACACAAGUGUUCAUCCUC | 62 | [464-482] (19/19) |
| 39 | Human, Chimp. | AAGACACGGCUUACCUGGA | 29 | UCCAGGUAAGCCGUGUCUU | 63 | [405-423] (19/19) |
| 74 | Human, Chimp. | UAAGCCAGGUGGGCAAAGA | 30 | UCUUUGCCCACCUGGCUUA | 64 | [573-591] (19/19) |
| 34 | Human, Chimp. | UCUGUCCUCACCAUGCCUA | 31 | UAGGCAUGGUGAGGACAGA | 65 | [191-209] (19/19) |
| 109 | Human, Chimp., Rabbit | UCAAGAAGAAGCUGUACAG | 32 | CUGUACAGCUUCUUCUUGA | 66 | [852-870] (19/19) |
| 129 | Human, Chimp., Rabbit | GCUGCUCAUUGAGGAGUGU | 33 | ACACUCCUCAAUGAGCAGC | 67 | [880-898] (19/19) |
| 111 | Human, Chimp., Rabbit | AAGAAGAAGCUGUACAGCU | 34 | AGCUGUACAGCUUCUUCUU | 68 | [854-872] (19/19) |
| 116 | Human, Chimp. | GAAGCUGUACAGCUCGGAA | 35 | UUCCGAGCUGUACAGCUUC | 69 | [859-877] (19/19) |
| 114 | Human, Chimp., Rabbit | AAGAAGCUGUACAGCUCGG | 36 | CCGAGCUGUACAGCUUCUU | 70 | [857-875] (19/19) |

Note that in the above Table A, the sense strands of siRNAs 1-34 have SEQ ID NOS: 3-36 respectively, and the antisense strands of siRNAs 1-34 have SEQ ID NOS: 37-70 respectively.

The invention claimed is:

1. A compound having the structure:

5' $(N)_x$—Z 3' (antisense strand)
3' Z'—$(N')_y$ 5' (sense strand)

wherein each N and N' is a ribonucleotide which may be modified or unmodified in its sugar residue and each of $(N)_x$ and $(N')_y$ is an oligomer in which each consecutive N or N' is joined to the next N or N' by a covalent bond;

wherein each of x and y is an integer from 19 to 40;

wherein each of Z and Z' may be present or absent, but if present is dTdT and is covalently attached at the 3' terminus of the strand in which it is present;

and wherein the sequence of (N)$_x$ comprises the sequence sequence set forth in either SEQ ID NO:44 or in SEQ ID NO:38.

2. A compound according to claim 1, wherein the covalent bond is a phosphodiester bond, x=y=19, Z and Z' are both absent, at least one ribonucleotide is modified in its sugar residue at the 2' position to be methoxy (2'-O-methyl), alternating ribonucleotides are modified in both the antisense and the sense strands, and the ribonucleotide at each of the 5' terminus and the 3' terminus of the antisense strand is modified in the sugar residue, and the ribonucleotide at each of the 5' terminus and the 3' terminus of the sense strand is unmodified in the sugar residue.

3. A compound according to claim 1, wherein each ribonucleotide at the 5' terminus and the 3' terminus of the antisense strand and of the sense strand is independently phosphorylated or non-phosphorylated.

4. A compound according to claim 1, wherein at least one of Z or Z' is present, and is the dinucleotide dTdT.

5. A compound according to claim 1, wherein a sugar residue in at least one nucleotide is modified.

6. A compound according to claim 5, wherein the modification in the sugar residue comprises replacing a 2' —OH group by a moiety selected from the group consisting of —H, —OCH$_3$, —OCH$_2$CH$_3$, —OCH$_2$CH$_2$CH$_3$, —NH$_2$, and —F.

7. A compound according to claim 6, wherein the moiety is —OCH$_3$.

8. The compound of claim 1, wherein the sequence of (N)$_x$ comprises the sequence set forth in SEQ ID No: 38.

9. A compound having the structure:

```
5' GCUUCUUCUUGAUGACUCG 3' antisense strand (SEQ ID
   |||||||||||||||||||            NO: 44)
3' CGAAGAAGAACUACUGAGC 5' sense strand (SEQ ID NO:
                                                10)
``` wherein each of A, C, G and U represents a ribonucleotide; wherein in alternating ribonucleotides in each of the antisense strand and the sense strand, a 2'-O-methyl group is present in the sugar residue;
wherein the ribonucleotide at each of the 5' terminus and the 3' terminus of the antisense strand comprises a 2'-O-methyl group in the sugar residue;
wherein the ribonucleotide at each of the 5' terminus and the 3' terminus of the sense strand is unmodified in the sugar residue; wherein each ribonucleotide at the 5' terminus and the 3' terminus of the antisense strand and of the sense strand is independently phosphorylated or non-phosphorylated; and wherein each vertical line (|) represents base pairing.

10. A compound having the structure:

```
5' AGCUUCUUCUUGAUGACUC 3' antisense strand (SEQ ID
   |||||||||||||||||||            NO: 38)
3' UCGAAGAAGAACUACUGAG 5' sense strand (SEQ ID NO:
                                                4)
``` wherein each of A, C, G and U represents a ribonucleotide; wherein in alternating ribonucleotides in each of the antisense strand and the sense strand, a 2'-O-methyl group is present in the sugar residue;
wherein the ribonucleotide at each of the 5' terminus and the 3' terminus of the antisense strand comprises a 2'-O-methyl group in the sugar residue;
wherein the ribonucleotide at each of the 5' terminus and the 3' terminus of the sense strand is unmodified in the sugar residue;
wherein each ribonucleotide at the 5' terminus and the 3' terminus of the antisense strand and of the sense strand is independently phosphorylated or non-phosphorylated; and wherein each vertical line (|) represents base pairing.

11. A compound having the structure:

```
5' GCUUCUUCUUGAUGACUCG 3' antisense strand (SEQ ID
   |||||||||||||||||||            NO: 44)
3' CGAAGAAGAACUACUGAGC 5' sense strand (SEQ ID NO:
                                                10)
``` wherein each of A, C, G and U represents a ribonucleotide; wherein in alternating ribonucleotides in each of the antisense strand and the sense strand, a 2'-O-methyl group is present in the sugar residue;
wherein the ribonucleotide at each of the 5' terminus and the 3' terminus of the antisense strand comprises a 2'-O-methyl group in the sugar residue;
wherein the ribonucleotide at each of the 5' terminus and the 3' terminus of the sense strand is unmodified in the sugar residue; wherein each ribonucleotide at the 5' terminus and the 3' terminus of the antisense strand and of the sense strand is independently phosphorylated or non-phosphorylated;
wherein each vertical line (|) represents base pairing, and wherein the sense and antisense strand are each 19 nucleotides in length.

12. A compound having the structure:

```
5' AGCUUCUUCUUGAUGACUC 3' antisense strand (SEQ ID
   |||||||||||||||||||            NO: 38)
3' UCGAAGAAGAACUACUGAG 5' sense strand (SEQ ID NO:
                                                4)
``` wherein each of A, C, G and U represents a ribonucleotide; wherein in alternating ribonucleotides in each of the antisense strand and the sense strand, a 2'-O-methyl group is present in the sugar residue;
wherein the ribonucleotide at each of the 5' terminus and the 3' terminus of the antisense strand comprises a 2'-O-methyl group in the sugar residue;
wherein the ribonucleotide at each of the 5' terminus and the 3' terminus of the sense strand is unmodified in the sugar residue;
wherein each ribonucleotide at the 5' terminus and the 3' terminus of the antisense strand and of the sense strand is independently phosphorylated or non-phosphorylated; and
wherein each vertical line (|) represents base pairing, and wherein the sense and antisense strand are each 19 nucleotides in length.

13. A composition comprising a compound of any of claims 1, 2, 3, 4, 6, 9, or 10 and a pharmaceutically acceptable carrier.

* * * * *

SEQUENCE LISTING

<160> NUMBER OF SEQ ID NOS: 70

<210> SEQ ID NO 1
<211> LENGTH: 1782
<212> TYPE: DNA
<213> ORGANISM: Homo sapiens

<400> SEQUENCE: 1

| | | | | | | |
|---|---|---|---|---|---|---|
| tttggccctc | gaggccaaga | attcggcacg | aggggggggag | gtgcgagcgt | ggacctggga | 60 |
| cgggtctggg | cggctctcgg | tggttggcac | gggttcgcac | acccattcaa | gcggcaggac | 120 |
| gcacttgtct | tagcagttct | cgctgaccgc | gctagctgcg | gcttctacgc | tccggcactc | 180 |
| tgagttcatc | agcaaacgcc | ctggcgtctg | tcctcaccat | gcctagcctt | tgggaccgct | 240 |
| tctcgtcgtc | gtccacctcc | tcttcgccct | cgtccttgcc | ccgaactccc | accccagatc | 300 |
| ggccgccgcg | ctcagcctgg | gggtcggcga | cccgggagga | ggggtttgac | cgctccacga | 360 |
| gcctggagag | ctcggactgc | gagtccctgg | acagcagcaa | cagtggcttc | gggccggagg | 420 |
| aagacacggc | ttacctggat | ggggtgtcgt | tgcccgactt | cgagctgctc | agtgaccctg | 480 |
| aggatgaaca | cttgtgtgcc | aacctgatgc | agctgctgca | ggagagcctg | gcccaggcgc | 540 |
| ggctgggctc | tcgacgccct | gcgcgcctgc | tgatgcctag | ccagttggta | agccaggtgg | 600 |
| gcaaagaact | actgcgcctg | gcctacagcg | agccgtgcgg | cctgcggggg | gcgctgctgg | 660 |
| acgtctgcgt | ggagcagggc | aagagctgcc | acagcgtggg | ccagctggca | ctcgacccca | 720 |
| gcctggtgcc | caccttccag | ctgaccctcg | tgctgcgcct | ggactcacga | ctctggccca | 780 |
| agatccaggg | gctgtttagc | tccgccaact | ctcccttcct | ccctggcttc | agccagtccc | 840 |
| tgacgctgag | cactggcttc | cgagtcatca | agaagaagct | gtacagctcg | gaacagctgc | 900 |
| tcattgagga | gtgttgaact | tcaacctgag | ggggccgaca | gtgccctcca | agacagagac | 960 |
| gactgaactt | tgggggtgga | gactagaggc | aggagctgag | ggactgattc | ctgtggttgg | 1020 |
| aaaactgagg | cagccaccta | aggtggaggt | ggggggaatag | tgtttcccag | gaagctcatt | 1080 |
| gagttgtgtg | cgggtggctg | tgcattgggg | acacatacccc | ctcagtactg | tagcatgaaa | 1140 |
| caaaggctta | ggggccaaca | aggcttccag | ctggatgtgt | gtgtagcatg | taccttatta | 1200 |
| tttttgttac | tgacagttaa | cagtggtgtg | acatccagag | agcagctggg | ctgctcccgc | 1260 |
| cccagcccgg | cccagggtga | aggaagaggc | acgtgctcct | cagagcagcc | ggagggaggg | 1320 |
| gggaggtcgg | aggtcgtgga | ggtggtttgt | gtatcttact | ggtctgaagg | gaccaagtgt | 1380 |
| gtttgttgtt | tgttttgtat | cttgtttttc | tgatcggagc | atcactactg | acctgttgta | 1440 |
| ggcagctatc | ttacagacgc | atgaatgtaa | gagtaggaag | gggtgggtgt | cagggatcac | 1500 |
| ttgggatctt | tgacacttga | aaaattacac | ctggcagctg | cgtttaagcc | ttcccccatc | 1560 |
| gtgtactgca | gagttgagct | ggcaggggag | gggctgagag | ggtgggggct | ggaacccctc | 1620 |
| cccgggagga | gtgccatctg | ggtcttccat | ctagaactgt | ttacatgaag | ataagatact | 1680 |
| cactgttcat | gaatacactt | gatgttcaag | tattaagacc | tatgcaatat | tttttacttt | 1740 |
| tctaataaac | atgtttgtta | aaacaaaaaa | aaaaaaaaaa | aa | | 1782 |

<210> SEQ ID NO 2
<211> LENGTH: 232
<212> TYPE: PRT
<213> ORGANISM: Homo sapiens

<400> SEQUENCE: 2

```
Met Pro Ser Leu Trp Asp Arg Phe Ser Ser Ser Thr Ser Ser Ser
1               5                   10                  15

Pro Ser Ser Leu Pro Arg Thr Pro Thr Pro Asp Arg Pro Arg Ser
            20                  25                  30

Ala Trp Gly Ser Ala Thr Arg Glu Glu Gly Phe Asp Arg Ser Thr Ser
        35                  40                  45

Leu Glu Ser Ser Asp Cys Glu Ser Leu Asp Ser Ser Asn Ser Gly Phe
    50                  55                  60

Gly Pro Glu Glu Asp Thr Ala Tyr Leu Asp Gly Val Ser Leu Pro Asp
65                  70                  75                  80

Phe Glu Leu Leu Ser Asp Pro Glu Asp Glu His Leu Cys Ala Asn Leu
                85                  90                  95

Met Gln Leu Leu Gln Glu Ser Leu Ala Gln Ala Arg Leu Gly Ser Arg
            100                 105                 110

Arg Pro Ala Arg Leu Leu Met Pro Ser Gln Leu Val Ser Gln Val Gly
        115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175

Leu Val Leu Arg Leu Asp Ser Arg Leu Trp Pro Lys Ile Gln Gly Leu
            180                 185                 190

Phe Ser Ser Ala Asn Ser Pro Phe Leu Pro Gly Phe Ser Gln Ser Leu
        195                 200                 205

Thr Leu Ser Thr Gly Phe Arg Val Ile Lys Lys Leu Tyr Ser Ser
    210                 215                 220

Glu Gln Leu Leu Ile Glu Glu Cys
225                 230
```

<210> SEQ ID NO 3
<211> LENGTH: 19
<212> TYPE: RNA
<213> ORGANISM: Artificial Sequence
<220> FEATURE:
<223> OTHER INFORMATION: Chemically synthesized

<400> SEQUENCE: 3
uccgagucau caagaagaa                                                19

<210> SEQ ID NO 4
<211> LENGTH: 19
<212> TYPE: RNA
<213> ORGANISM: Artificial Sequence
<220> FEATURE:
<223> OTHER INFORMATION: Chemically synthesized

<400> SEQUENCE: 4
gagucaucaa gaagaagcu                                                19

<210> SEQ ID NO 5
<211> LENGTH: 19
<212> TYPE: RNA
<213> ORGANISM: Artificial Sequence
<220> FEATURE:
<223> OTHER INFORMATION: Chemically synthesized

<400> SEQUENCE: 5
uggcuuccga gucaucaag                                                19

<210> SEQ ID NO 6
<211> LENGTH: 19
<212> TYPE: RNA
<213> ORGANISM: Artificial sequence
<220> FEATURE:
<223> OTHER INFORMATION: Sense siRNA strand

<400> SEQUENCE: 6
gucaucaaga agaagcugu                                                19

<210> SEQ ID NO 7
<211> LENGTH: 19
<212> TYPE: RNA
<213> ORGANISM: Artificial sequence
<220> FEATURE:
<223> OTHER INFORMATION: siRNA sense strand

<400> SEQUENCE: 7
agacacggcu uaccuggau                                                19

<210> SEQ ID NO 8
<211> LENGTH: 19
<212> TYPE: RNA
<213> ORGANISM: Artificial sequence
<220> FEATURE:
<223> OTHER INFORMATION: siRNA sense strand

<400> SEQUENCE: 8
aucaagaaga agcuguaca                                                19

<210> SEQ ID NO 9
<211> LENGTH: 19
<212> TYPE: RNA
<213> ORGANISM: Artificial sequence
<220> FEATURE:
<223> OTHER INFORMATION: siRNA sense strand

<400> SEQUENCE: 9
cagcugcuca uugaggagu                                                19

<210> SEQ ID NO 10
<211> LENGTH: 19
<212> TYPE: RNA
<213> ORGANISM: Artificial Sequence
<220> FEATURE:
<223> OTHER INFORMATION: siRNA sense strand

<400> SEQUENCE: 10
cgagucauca agaagaagc                                                19

<210> SEQ ID NO 11
<211> LENGTH: 19
<212> TYPE: RNA
<213> ORGANISM: Artificial sequence
<220> FEATURE:
<223> OTHER INFORMATION: siRNA sense strand

<400> SEQUENCE: 11
ggcuuccgag ucaucaaga                                                19

<210> SEQ ID NO 12
<211> LENGTH: 19
<212> TYPE: RNA

```
<213> ORGANISM: Artificial sequence
<220> FEATURE:
<223> OTHER INFORMATION: siRNA sense strand

<400> SEQUENCE: 12
gcaaagaacu acugcgccu                                                        19

<210> SEQ ID NO 13
<211> LENGTH: 19
<212> TYPE: RNA
<213> ORGANISM: Artificial sequence
<220> FEATURE:
<223> OTHER INFORMATION: siRNA sense strand

<400> SEQUENCE: 13
gaugaacacu ugugugcca                                                        19

<210> SEQ ID NO 14
<211> LENGTH: 19
<212> TYPE: RNA
<213> ORGANISM: Artificial Sequence
<220> FEATURE:
<223> OTHER INFORMATION: siRNA sense strand

<400> SEQUENCE: 14
cccugaggau gaacacuug                                                        19

<210> SEQ ID NO 15
<211> LENGTH: 19
<212> TYPE: RNA
<213> ORGANISM: Artificial Sequence
<220> FEATURE:
<223> OTHER INFORMATION: siRNA sense strand

<400> SEQUENCE: 15
aggaagacac ggcuuaccu                                                        19

<210> SEQ ID NO 16
<211> LENGTH: 19
<212> TYPE: RNA
<213> ORGANISM: Artificial sequence
<220> FEATURE:
<223> OTHER INFORMATION: siRNA sense strand

<400> SEQUENCE: 16
ucagugaccc ugaggauga                                                        19

<210> SEQ ID NO 17
<211> LENGTH: 19
<212> TYPE: RNA
<213> ORGANISM: Artificial sequence
<220> FEATURE:
<223> OTHER INFORMATION: siRNA sense strand

<400> SEQUENCE: 17
cagugacccu gaggaugaa                                                        19

<210> SEQ ID NO 18
<211> LENGTH: 19
<212> TYPE: RNA
<213> ORGANISM: Artificial Sequence
<220> FEATURE:
<223> OTHER INFORMATION: siRNA sense strand

<400> SEQUENCE: 18
aacagcugcu cauugagga                                                        19
```

```
<210> SEQ ID NO 19
<211> LENGTH: 19
<212> TYPE: RNA
<213> ORGANISM: Artificial sequence
<220> FEATURE:
<223> OTHER INFORMATION: siRNA sense strand

<400> SEQUENCE: 19
gaacagcugc ucauugagg                                                    19

<210> SEQ ID NO 20
<211> LENGTH: 19
<212> TYPE: RNA
<213> ORGANISM: Siratus beauii

<400> SEQUENCE: 20
ucggaacagc ugcucauug                                                    19

<210> SEQ ID NO 21
<211> LENGTH: 19
<212> TYPE: RNA
<213> ORGANISM: Artificial sequence
<220> FEATURE:
<223> OTHER INFORMATION: siRNA sense strand

<400> SEQUENCE: 21
agcugcucau ugaggagug                                                    19

<210> SEQ ID NO 22
<211> LENGTH: 19
<212> TYPE: RNA
<213> ORGANISM: Artificial sequence
<220> FEATURE:
<223> OTHER INFORMATION: siRNA sense strand

<400> SEQUENCE: 22
aagcuguaca gcucggaac                                                    19

<210> SEQ ID NO 23
<211> LENGTH: 19
<212> TYPE: RNA
<213> ORGANISM: Artificial sequence
<220> FEATURE:
<223> OTHER INFORMATION: siRNA sense strand

<400> SEQUENCE: 23
ugcucauuga ggaguguug                                                    19

<210> SEQ ID NO 24
<211> LENGTH: 19
<212> TYPE: RNA
<213> ORGANISM: Artificial sequence
<220> FEATURE:
<223> OTHER INFORMATION: siRNA sense strand

<400> SEQUENCE: 24
ucaucaagaa gaagcugua                                                    19

<210> SEQ ID NO 25
<211> LENGTH: 19
<212> TYPE: RNA
<213> ORGANISM: Artificial sequence
<220> FEATURE:
<223> OTHER INFORMATION: siRNA sense strand
```

```
<400> SEQUENCE: 25
cguuuuagcu ccgccaacu                                                19

<210> SEQ ID NO 26
<211> LENGTH: 19
<212> TYPE: RNA
<213> ORGANISM: Artificial sequence
<220> FEATURE:
<223> OTHER INFORMATION: siRNA sense strand

<400> SEQUENCE: 26
augaacacuu gugugccaa                                                19

<210> SEQ ID NO 27
<211> LENGTH: 19
<212> TYPE: RNA
<213> ORGANISM: Artificial sequence
<220> FEATURE:
<223> OTHER INFORMATION: siRNA sense strand

<400> SEQUENCE: 27
acacuugugu gccaaccug                                                19

<210> SEQ ID NO 28
<211> LENGTH: 19
<212> TYPE: RNA
<213> ORGANISM: Artificial sequence
<220> FEATURE:
<223> OTHER INFORMATION: siRNA sense strand

<400> SEQUENCE: 28
gaggaugaac acuugugug                                                19

<210> SEQ ID NO 29
<211> LENGTH: 19
<212> TYPE: RNA
<213> ORGANISM: Artificial sequence
<220> FEATURE:
<223> OTHER INFORMATION: siRNA sense strand

<400> SEQUENCE: 29
aagacacggc uuaccugga                                                19

<210> SEQ ID NO 30
<211> LENGTH: 19
<212> TYPE: RNA
<213> ORGANISM: Artificial sequence
<220> FEATURE:
<223> OTHER INFORMATION: siRNA sense strand

<400> SEQUENCE: 30
uaagccaggu gggcaaaga                                                19

<210> SEQ ID NO 31
<211> LENGTH: 19
<212> TYPE: RNA
<213> ORGANISM: Artificial sequence
<220> FEATURE:
<223> OTHER INFORMATION: siRNA sense strand

<400> SEQUENCE: 31 ucguccuca ccaugccua                                                 19

<210> SEQ ID NO 32
<211> LENGTH: 19
```

```
<212> TYPE: RNA
<213> ORGANISM: Artificial sequence
<220> FEATURE:
<223> OTHER INFORMATION: siRNA sense strand

<400> SEQUENCE: 32
ucaagaagaa gcuguacag                                                    19

<210> SEQ ID NO 33
<211> LENGTH: 19
<212> TYPE: RNA
<213> ORGANISM: Artificial sequence
<220> FEATURE:
<223> OTHER INFORMATION: siRNA sense strand

<400> SEQUENCE: 33
gcugcucauu gaggagugu                                                    19

<210> SEQ ID NO 34
<211> LENGTH: 19
<212> TYPE: RNA
<213> ORGANISM: Artificial sequence
<220> FEATURE:
<223> OTHER INFORMATION: siRNA sense strand

<400> SEQUENCE: 34
aagaagaagc uguacagcu                                                    19

<210> SEQ ID NO 35
<211> LENGTH: 19
<212> TYPE: RNA
<213> ORGANISM: Artificial sequence
<220> FEATURE:
<223> OTHER INFORMATION: siRNA sense strand

<400> SEQUENCE: 35
gaagcuguac agcucggaa                                                    19

<210> SEQ ID NO 36
<211> LENGTH: 19
<212> TYPE: RNA
<213> ORGANISM: Artificial sequence
<220> FEATURE:
<223> OTHER INFORMATION: siRNA sense strand

<400> SEQUENCE: 36
aagaagcugu acagcucgg                                                    19

<210> SEQ ID NO 37
<211> LENGTH: 19
<212> TYPE: RNA
<213> ORGANISM: Artificial sequence
<220> FEATURE:
<223> OTHER INFORMATION: siRNA antisense strand

<400> SEQUENCE: 37
uucuucuuga ugacucgga                                                    19

<210> SEQ ID NO 38
<211> LENGTH: 19
<212> TYPE: RNA
<213> ORGANISM: Artificial sequence
<220> FEATURE:
<223> OTHER INFORMATION: siRNA antisense strand

<400> SEQUENCE: 38
```
agcuucuucu ugaugacuc                                             19

<210> SEQ ID NO 39
<211> LENGTH: 19
<212> TYPE: RNA
<213> ORGANISM: Artificial sequence
<220> FEATURE:
<223> OTHER INFORMATION: siRNA antisense strand

<400> SEQUENCE: 39
cuugaugacu cggaagcca                                             19

<210> SEQ ID NO 40
<211> LENGTH: 19
<212> TYPE: RNA
<213> ORGANISM: Artificial sequence
<220> FEATURE:
<223> OTHER INFORMATION: siRNA antisense strand

<400> SEQUENCE: 40
acagcuucuu cuugaugac                                             19

<210> SEQ ID NO 41
<211> LENGTH: 19
<212> TYPE: RNA
<213> ORGANISM: Artificial sequence
<220> FEATURE:
<223> OTHER INFORMATION: siRNA antisense strand

<400> SEQUENCE: 41
auccagguaa gccgugucu                                             19

<210> SEQ ID NO 42
<211> LENGTH: 19
<212> TYPE: RNA
<213> ORGANISM: Artificial sequence
<220> FEATURE:
<223> OTHER INFORMATION: siRNA antisense strand

<400> SEQUENCE: 42
uguacagcuu cuucuugau                                             19

<210> SEQ ID NO 43
<211> LENGTH: 19
<212> TYPE: RNA
<213> ORGANISM: Artificial sequence
<220> FEATURE:
<223> OTHER INFORMATION: siRNA antisense strand

<400> SEQUENCE: 43
acuccucaau gagcagcug                                             19

<210> SEQ ID NO 44
<211> LENGTH: 19
<212> TYPE: RNA
<213> ORGANISM: Artificial sequence
<220> FEATURE:
<223> OTHER INFORMATION: siRNA antisense strand

<400> SEQUENCE: 44
gcuucuucuu gaugacucg                                             19

<210> SEQ ID NO 45
<211> LENGTH: 19
<212> TYPE: RNA
<213> ORGANISM: Artificial sequence

```
<220> FEATURE:
<223> OTHER INFORMATION: siRNA antisense strand

<400> SEQUENCE: 45
ucuugaugac ucggaagcc                                              19

<210> SEQ ID NO 46
<211> LENGTH: 19
<212> TYPE: RNA
<213> ORGANISM: Artificial sequence
<220> FEATURE:
<223> OTHER INFORMATION: siRNA antisense strand

<400> SEQUENCE: 46
aggcgcagua guucuuugc                                              19

<210> SEQ ID NO 47
<211> LENGTH: 19
<212> TYPE: RNA
<213> ORGANISM: Artificial sequence
<220> FEATURE:
<223> OTHER INFORMATION: siRNA antisense strand

<400> SEQUENCE: 47
uggcacacaa guguucauc                                              19

<210> SEQ ID NO 48
<211> LENGTH: 19
<212> TYPE: RNA
<213> ORGANISM: Artificial sequence
<220> FEATURE:
<223> OTHER INFORMATION: siRNA antisense strand

<400> SEQUENCE: 48
caaguguuca uccucaggg                                              19

<210> SEQ ID NO 49
<211> LENGTH: 19
<212> TYPE: RNA
<213> ORGANISM: Artificial sequence
<220> FEATURE:
<223> OTHER INFORMATION: siRNA antisense strand

<400> SEQUENCE: 49
agguaagccg ugucuuccu                                              19

<210> SEQ ID NO 50
<211> LENGTH: 19
<212> TYPE: RNA
<213> ORGANISM: Artificial sequence
<220> FEATURE:
<223> OTHER INFORMATION: siRNA antisense strand

<400> SEQUENCE: 50
ucauccucag ggucacuga                                              19

<210> SEQ ID NO 51
<211> LENGTH: 19
<212> TYPE: RNA
<213> ORGANISM: Artificial sequence
<220> FEATURE:
<223> OTHER INFORMATION: siRNA antisense strand

<400> SEQUENCE: 51
uucauccuca gggucacug                                              19
```

<210> SEQ ID NO 52
<211> LENGTH: 19
<212> TYPE: RNA
<213> ORGANISM: Artificial sequence
<220> FEATURE:
<223> OTHER INFORMATION: siRNA antisense strand

<400> SEQUENCE: 52
uccucaauga gcagcuguu                                              19

<210> SEQ ID NO 53
<211> LENGTH: 19
<212> TYPE: RNA
<213> ORGANISM: Artificial sequence
<220> FEATURE:
<223> OTHER INFORMATION: siRNA antisense strand

<400> SEQUENCE: 53
ccucaaugag cagcuguuc                                              19

<210> SEQ ID NO 54
<211> LENGTH: 19
<212> TYPE: RNA
<213> ORGANISM: Artificial sequence
<220> FEATURE:
<223> OTHER INFORMATION: siRNA antisense strand

<400> SEQUENCE: 54
caaugagcag cguuccga                                               19

<210> SEQ ID NO 55
<211> LENGTH: 19
<212> TYPE: RNA
<213> ORGANISM: Artificial sequence
<220> FEATURE:
<223> OTHER INFORMATION: siRNA antisense strand

<400> SEQUENCE: 55
cacuccucaa ugagcagcu                                              19

<210> SEQ ID NO 56
<211> LENGTH: 19
<212> TYPE: RNA
<213> ORGANISM: Artificial sequence
<220> FEATURE:
<223> OTHER INFORMATION: siRNA antisense strand

<400> SEQUENCE: 56
guuccgagcu guacagcuu                                              19

<210> SEQ ID NO 57
<211> LENGTH: 19
<212> TYPE: RNA
<213> ORGANISM: Artificial sequence
<220> FEATURE:
<223> OTHER INFORMATION: siRNA antisense strand

<400> SEQUENCE: 57
caacacuccu caaugagca                                              19

<210> SEQ ID NO 58
<211> LENGTH: 19
<212> TYPE: RNA
<213> ORGANISM: Artificial sequence
<220> FEATURE:
<223> OTHER INFORMATION: siRNA antisense strand

```
<400> SEQUENCE: 58
uacagcuucu ucuugauga                                              19

<210> SEQ ID NO 59
<211> LENGTH: 19
<212> TYPE: RNA
<213> ORGANISM: Artificial sequence
<220> FEATURE:
<223> OTHER INFORMATION: siRNA antisense strand

<400> SEQUENCE: 59
aguuggcgga gcuaaacag                                              19

<210> SEQ ID NO 60
<211> LENGTH: 19
<212> TYPE: RNA
<213> ORGANISM: Artificial sequence
<220> FEATURE:
<223> OTHER INFORMATION: siRNA antisense strand

<400> SEQUENCE: 60
uuggcacaca aguguucau                                              19

<210> SEQ ID NO 61
<211> LENGTH: 19
<212> TYPE: RNA
<213> ORGANISM: Artificial sequence
<220> FEATURE:
<223> OTHER INFORMATION: siRNA antisense strand

<400> SEQUENCE: 61
cagguuggca cacaagugu                                              19

<210> SEQ ID NO 62
<211> LENGTH: 19
<212> TYPE: RNA
<213> ORGANISM: Artificial sequence
<220> FEATURE:
<223> OTHER INFORMATION: siRNA antisense strand

<400> SEQUENCE: 62
cacacaagug uucauccuc                                              19

<210> SEQ ID NO 63
<211> LENGTH: 19
<212> TYPE: RNA
<213> ORGANISM: Artificial sequence
<220> FEATURE:
<223> OTHER INFORMATION: siRNA antisense strand

<400> SEQUENCE: 63
uccagguaag ccgugucuu                                              19

<210> SEQ ID NO 64
<211> LENGTH: 19
<212> TYPE: RNA
<213> ORGANISM: Artificial sequence
<220> FEATURE:
<223> OTHER INFORMATION: siRNA antisense strand

<400> SEQUENCE: 64
ucuuugccca ccuggcuua                                              19

<210> SEQ ID NO 65
```

```
<210> SEQ ID NO 65
<211> LENGTH: 19
<212> TYPE: RNA
<213> ORGANISM: Artificial sequence
<220> FEATURE:
<223> OTHER INFORMATION: siRNA antisense strand

<400> SEQUENCE: 65
uaggcauggu gaggacaga                                              19

<210> SEQ ID NO 66
<211> LENGTH: 19
<212> TYPE: RNA
<213> ORGANISM: Artificial sequence
<220> FEATURE:
<223> OTHER INFORMATION: siRNA antisense strand

<400> SEQUENCE: 66
cuguacagcu ucuucuuga                                              19

<210> SEQ ID NO 67
<211> LENGTH: 19
<212> TYPE: RNA
<213> ORGANISM: Artificial sequence
<220> FEATURE:
<223> OTHER INFORMATION: siRNA antisense strand

<400> SEQUENCE: 67
acacuccuca augagcagc                                              19

<210> SEQ ID NO 68
<211> LENGTH: 19
<212> TYPE: RNA
<213> ORGANISM: Artificial sequence
<220> FEATURE:
<223> OTHER INFORMATION: siRNA antisense strand

<400> SEQUENCE: 68
agcuguacag cuucuucuu                                              19

<210> SEQ ID NO 69
<211> LENGTH: 19
<212> TYPE: RNA
<213> ORGANISM: Artificial sequence
<220> FEATURE:
<223> OTHER INFORMATION: siRNA antisense strand

<400> SEQUENCE: 69
uuccgagcug uacagcuuc                                              19

<210> SEQ ID NO 70
<211> LENGTH: 19
<212> TYPE: RNA
<213> ORGANISM: Artificial sequence
<220> FEATURE:
<223> OTHER INFORMATION: siRNA antisense strand

<400> SEQUENCE: 70
ccgagcugua cagcuucuu                                              19
```